US009138475B2

(12) United States Patent
Vistica et al.

(10) Patent No.: US 9,138,475 B2
(45) Date of Patent: Sep. 22, 2015

(54) HUMAN MONOCLONAL ANTIBODIES TO FUCOSYL-GM1 AND METHODS FOR USING ANTI-FUCOSYL-GM1 ANTIBODIES

(71) Applicant: E. R. Squibb & Sons, L.L.C., Princeton, NJ (US)

(72) Inventors: Cynthia A. Vistica, Dublin, CA (US); Eric H. Holmes, Bothell, WA (US); Peter Brams, Sacramento, CA (US); Alison Witte, Rogue River, OR (US); Josephine M. Cardarelli, San Carlos, CA (US)

(73) Assignee: E. R. Squibb & Sons, L.L.C., Princeton, NJ (US)

( * ) Notice: Subject to any disclaimer, the term of this patent is extended or adjusted under 35 U.S.C. 154(b) by 0 days.

(21) Appl. No.: 13/746,762

(22) Filed: Jan. 22, 2013

(65) Prior Publication Data

US 2013/0142789 A1 Jun. 6, 2013

Related U.S. Application Data

(62) Division of application No. 12/095,557, filed as application No. PCT/US2006/061817 on Dec. 8, 2006, now Pat. No. 8,383,118.

(60) Provisional application No. 60/748,915, filed on Dec. 8, 2005.

(51) Int. Cl.

| | |
|---|---|
| ***A61K 39/40*** | (2006.01) |
| ***A61K 39/395*** | (2006.01) |
| ***C07K 16/30*** | (2006.01) |
| ***A61K 45/06*** | (2006.01) |
| *A61K 39/00* | (2006.01) |

(52) U.S. Cl.

CPC ........... *A61K 39/39558* (2013.01); *A61K 45/06* (2013.01); *C07K 16/3084* (2013.01); *A61K 2039/505* (2013.01); *C07K 2317/21* (2013.01); *C07K 2317/732* (2013.01); *C07K 2317/734* (2013.01); *C07K 2317/77* (2013.01)

(58) Field of Classification Search

None

See application file for complete search history.

(56) References Cited

U.S. PATENT DOCUMENTS

| | | | |
|---|---|---|---|
| 4,867,973 | A | 9/1989 | Goers et al. |
| 7,687,607 | B2 | 3/2010 | Gelber |
| 8,383,118 | B2 | 2/2013 | Vistica et al. |

FOREIGN PATENT DOCUMENTS

| | | |
|---|---|---|
| WO | WO 96/33735 | 10/1996 |
| WO | WO 99/15201 | 4/1999 |
| WO | WO 01/09187 | 2/2001 |
| WO | WO 01/14395 | 3/2001 |
| WO | WO 2004/011476 | 2/2004 |
| WO | WO 2004/050708 | 6/2004 |
| WO | WO 2004/091507 | 10/2004 |
| WO | WO 2005/056572 | 6/2005 |
| WO | WO 2007/044620 | 4/2007 |

OTHER PUBLICATIONS

Owens et al J of Immunol Method , 1994, V.168, pp. 149-165).*

Brezicka, F.T. et al., "Tumor-Cell Killing by MABS Against Fucosyl GM1, a Ganglioside Antigen Associated With Small-Cell Lung Carcinoma", International Journal of Cancer, New York, NY, US; XP009063400, vol. 49, pp. 911-918, ISSN: 0020-7136, 1991.

Brezicka, Thomas et al., "Supra-Additive Cytotoxic Effects of a Combination of Cytostatic Drugs and Antibody-Induced Complement Activation on Tumor Cells in Vitro", Tumor Biology, XP008082925, vol. 22, No. 2, pp. 97-103, ISSN: 1010-4283, Mar. 2001.

Brezicka, F.T. et al., "Immunohistological Detection of Fucosyl-G-M-1 Ganglioside in Human Lung Cancer and Normal Tissue With Monoclonal Antibodies", Cancer Research, XP002449385, vol. 49, No. 5, pp. 1300-1305, ISSN: 0008-5472, 1989.

Vangsted, A.J. et al, "Monoclonal Antibodies for Diagnosis and Potential Therapy of Small Cell Lungcancer—the Ganglioside Antigen Fucosyl-GM1" Acta Oncologica, Informa Healthcare, London, GB, XP008082926, vol. 32, No. 7-8, pp. 845-851, ISSN: 0284-186X, 1993.

Yoshino, H. et al., "Fucosyl-GM1 in Human Sensory Nervous Tissue Is a Target Antigen in Patients With Autoimmune Neuropathies", Journal of Neurochemistry, New York, NY, US, XP008082960, pp. 658-663, ISSN: 0022-3042, 1993.

Carson el al., "Human Lymphocyte Hybridomas and Monoclonal Antibodies", *Advances in Immunology*, 38:275-311, 1986.

Nilsson el al., "Detection of a Ganglioside Antigen Associated with Small Cell Lung Carcinomas Using Monoclonal Antibodies Directed against Fucosyl-GM1", *Cancer Research*, 46:1403-1407, 1998.

Sikora, "Human Monoclonal Antibodies", *British Medical Bulletin*. 40(3):209-212, 1984.

Tomizuka et al., "Development of Human Antibody Therapeutics Using Trans-Chromo (TC) Mouse", *Bio Industry*. 20(7):43-51, 2003. (Reference is in Japanese language only).

Yuki et al., "Antibodies to Fucogangliosides in Neurological Diseases", *Journal of Neurological Sciences*, 150:81-84, 1997.

Zhang et al., "Selection of Tumor Antigens as Targets for Immune Attack Using Immunohistochemistry: I. Focus on Gangliosides", *Int. J. Cancer*, 73:42-49, 1997.

Lerner Nature 1982: 299:592-596.

Kusunoki et al., BBA, 1994, v.1214, pp. 27-31.

Laurence et al (Nature Immunol, 2007, v.9, pp. 903-905.

Mestas et al ( J. of Immunology, 2004, 172, pp. 2731-2738.

Feldman et al .Transplant. Proc. 1998. 30, 4126-4127.

* cited by examiner

*Primary Examiner* — Michail Belyavskyi

(74) *Attorney, Agent, or Firm* — Gregory R. Bellomy; Z. Angela Guo

(57) ABSTRACT

The present disclosure provides isolated monoclonal antibodies, particularly human monoclonal antibodies that specifically bind to Fucosyl-GM1 with high affinity. Nucleic acid molecules encoding the antibodies of this disclosure, expression vectors, host cells and methods for expressing the antibodies of this disclosure are also provided. Immunoconjugates, bispecific molecules and pharmaceutical compositions comprising the antibodies of this disclosure are also provided. This disclosure also provides methods for detecting Fucosyl-GM1, as well as methods for treating various diseases, including cancer, using anti-Fucosyl-GM1 antibodies.

16 Claims, 31 Drawing Sheets

Anti-Fucosyl GM1 5B1 VH

V-segment: VH 3-48
D-segment: D1-1
J-segment: JH6b

```
        E   V   Q   L   V   E   S   G   G   G   L   V   Q   P   G   E   S   L
1      GAG GTG CAG CTG GTG GAG TCT GGG GGA GGC TTG GTG CAG CCT GGG GAG TCC CTG

                                                            CDR 1
                                                        ~~~~~~~~~~~~~~~~~~~~
        R   L   S   C   V   A   S   G   F   T   F   S   R   Y   K   M   N   W
55     AGA CTC TCC TGT GTA GCC TCT GGA TTT ACT TTC AGT AGA TAT AAG ATG AAC TGG

                                                                CDR 2
                                                            ~~~~~~~~~~~~~~~~
        V   R   Q   A   P   G   K   G   L   E   W   V   S   Y   I   S   R   S
109    GTT CGC CAG GCT CCA GGG AAG GGA CTG GAA TGG GTT TCA TAC ATC AGT CGT AGT

                    CDR 2
       ~~~~~~~~~~~~~~~~~~~~~~~~~~~~~~~~~~~~~~~~~~~~~~
        G   R   D   I   Y   Y   A   D   S   V   K   G   R   F   T   I   S   R
163    GGC CGT GAC ATT TAC TAC GCA GAC TCT GTG AAG GGC CGA TTC ACC ATC TCC AGA

        D   N   A   K   N   S   L   Y   L   Q   M   N   S   L   R   D   E   D
217    GAT AAT GCC AAG AAC TCA CTG TAT CTG CAA ATG AAC AGC CTG AGA GAC GAG GAC

                                                  CDR 3
                                       ~~~~~~~~~~~~~~~~~~~~~~~~~~~~~~~~~~~~~~
        T   A   V   Y   Y   C   A   G   T   V   T   T   Y   Y   Y   Y   F   G
271    ACG GCT GTA TAT TAC TGT GCG GGA ACT GTA ACG ACA TAC TAC TAC TAC TTC GGT
                                         D1-1                JH6b

         CDR 3
       ~~~~~~~~~~~
        M   D   V   W   G   H   G   T   T   V   T   V   S   S
325    ATG GAC GTC TGG GGC CAC GGG ACC ACG GTC ACC GTC TCC TCA
```

*Figure 1A*

```
Anti-Fucosyl GM1 5B1 VK

       V-segment:  L15
       J-segment:  JK4

        D   I   Q   M   T   Q   S   P   S   S   L   S   A   S   V   G   D   R
  1    GAC ATC CAG ATG ACC CAG TCT CCA TCC TCA CTG TCT GCA TCT GTA GGA GAC AGA

                                               CDR 1
                                ~~~~~~~~~~~~~~~~~~~~~~~~~~~~~~~~~~~~~~~~~~~
        V   T   I   T   C   R   A   S   Q   G   I   S   S   W   L   A   W   Y
 55    GTC ACC ATC ACT TGT CGG GCG AGT CAG GGT ATT AGC AGC TGG TTA GCC TGG TAT

                                                                CDR 2
                                                            ~~~~~~~~~~~~~~~~~~~
        Q   Q   K   P   E   K   A   P   K   S   L   I   Y   A   A   S   S   L
109    CAG CAG AAA CCA GAG AAA GCC CCT AAG TCC CTG ATC TAT GCT GCA TCC AGT TTG

       CDR 2
       ~~~~~~~~
        Q   S   G   V   P   S   R   F   S   G   S   G   S   G   T   D   F   T
163    CAA AGT GGG GTC CCA TCA AGG TTC AGC GGC AGT GGA TCT GGG ACA GAT TTC ACT

                                                                       CDR 3
                                                                    ~~~~~~~
        L   T   I   S   S   L   Q   P   E   D   F   A   T   Y   Y   C   Q   Q
217    CTC ACC ATC AGC AGC CTG CAG CCT GAA GAT TTT GCA ACT TAT TAC TGC CAA CAG

             CDR 3
       ~~~~~~~~~~~~~~~~~~~~~~~~~~~~
        Y   N   S   Y   P   P   T   F   G   G   G   T   K   V   E   I   K
271    TAT AAT AGT TAC CCT CCC ACT TTC GGC GGA GGG ACC AAG GTG GAG ATC AAA
                               └─► JK4
```

*Figure 1B*

Anti-FucosylGM 5B1a VH

V-segment: VH 3-48
D-segment: D1-1
J-segment: JH6b

```
         E   V   Q   L   V   E   S   G   G   G   L   V   Q   P   G   E   S   L
  1     GAG GTG CAG CTG GTG GAG TCT GGG GGA GGC TTG GTG CAG CCT GGG GAG TCC CTG

                                                             CDR 1
                                                         ~~~~~~~~~~~~~~~~~~~~
         R   L   S   C   V   A   S   G   F   T   F   S   R   Y   K   M   N   W
 55     AGA CTC TCC TGT GTA GCC TCT GGA TTT ACT TTC AGT AGA TAT AAG ATG AAC TGG

                                                                 CDR 2
                                                             ~~~~~~~~~~~~~~~~~~
         V   R   Q   A   P   G   K   G   L   E   W   V   S   Y   I   S   R   S
109     GTT CGC CAG GCT CCA GGG AAG GGA CTG GAA TGG GTT TCA TAC ATC AGT CGT AGT

                     CDR 2
        ~~~~~~~~~~~~~~~~~~~~~~~~~~~~~~~~~~~~~~~~~~~~~~
         G   R   D   I   Y   Y   A   D   S   V   K   G   R   F   T   I   S   R
163     GGC CGT GAC ATT TAC TAC GCA GAC TCT GTG AAG GGC CGA TTC ACC ATC TCC AGA

         D   N   A   K   N   S   L   Y   L   Q   M   N   S   L   R   D   E   D
217     GAT AAT GCC AAG AAC TCA CTG TAT CTG CAA ATG AAC AGC CTG AGA GAC GAG GAC

                                                      CDR 3
                                        ~~~~~~~~~~~~~~~~~~~~~~~~~~~~~~~~~~~~~~~~
         T   A   V   Y   Y   C   A   G   T   V   T   T   Y   Y   Y   F   G   M
271     ACG GCT GTA TAT TAC TGT GCG GGA ACT GTA ACG ACA TAC TAC TAC TTC GGT ATG
                                       |     D1-1      |  |->
                                                              JH6b
        CDR 3
        ~~~~~~~~
         D   V   W   G   H   G   T   T   V   T   V   S   S
325     GAC GTC TGG GGC CAC GGG ACC ACG GTC ACC GTC TCC TCA
```

*Figure 2A*

Anti-Fucosyl GM1 5B1a VK

V-segment: L15
J-segment: JK4

```
          D   I   Q   M   T   Q   S   P   S   S   L   S   A   S   V   G   D   R
  2      GAC ATC CAG ATG ACC CAG TCT CCA TCC TCA CTG TCT GCA TCT GTA GGA GAC AGA

                                      CDR 1
                              ~~~~~~~~~~~~~~~~~~~~~~~~~~~~~~~~~~~~~~~~~~~~
          V   T   I   T   C   R   A   S   Q   G   I   S   S   W   L   A   W   Y
 56      GTC ACC ATC ACT TGT CGG GCG AGT CAG GGT ATT AGC AGC TGG TTA GCC TGG TAT

                                                                 CDR 2
                                                          ~~~~~~~~~~~~~~~~~~
          Q   Q   K   P   E   K   A   P   K   S   L   I   Y   A   A   S   S   L
110      CAG CAG AAA CCA GAG AAA GCC CCT AAG TCC CTG ATC TAT GCT GCA TCC AGT TTG

         CDR 2
         ~~~~~~~~
          Q   S   G   V   P   S   R   F   S   G   S   G   S   G   T   D   F   T
164      CAA AGT GGG GTC CCA TCA AGG TTC AGC GGC AGT GGA TCT GGG ACA GAT TTC ACT

                                                                     CDR 3
                                                                   ~~~~~~~
          L   T   I   S   S   L   Q   P   E   D   F   A   T   Y   Y   C   Q   Q
218      CTC ACC ATC AGC AGC CTG CAG CCT GAA GAT TTT GCA ACT TAT TAC TGC CAA CAG

                 CDR 3
         ~~~~~~~~~~~~~~~~~~~~~~~~~~~~
          Y   N   S   Y   P   P   T   F   G   G   G   T   K   V   E   I   K
272      TAT AAT AGT TAC CCT CCC ACT TTC GGC GGA GGG ACC AAG GTG GAG ATC AAA
                                 |
                                 └→ JK4
```

*Figure 2B*

Anti-Fucosyl GM1 7D4 VH

V-segment: VH 3-48
D-segment: D1-1
J-segment: JH6b

```
        E   V   Q   L   V   E   S   G   G   G   L   V   Q   P   G   E   S   L
  1    GAG GTG CAG CTG GTG GAG TCT GGG GGA GGC TTG GTA CAG CCT GGG GAG TCC CTG

                                                               CDR1
                                                        ~~~~~~~~~~~~~~~~~~~~
        R   L   S   C   V   V   S   G   F   T   F   S   R   Y   K   M   N   W
 55    AGA CTC TCC TGT GTA GTC TCT GGA TTC ACC TTC AGT AGG TAT AAG ATG AAC TGG

                                                                   CDR2
                                                            ~~~~~~~~~~~~~~~~~~~
        V   R   Q   A   P   G   K   G   L   E   W   I   S   Y   I   S   R   S
109    GTC CGC CAG GCT CCA GGG AAG GGA CTG GAA TGG ATT TCA TAC ATT AGT CGT AGT

                   CDR2
       ~~~~~~~~~~~~~~~~~~~~~~~~~~~~~~~~~~~~~~~~~~~~~~~~~
        G   R   D   I   Y   Y   A   D   S   V   K   G   R   F   T   I   S   R
163    GGT CGT GAC ATA TAC TAC GCA GAC TCT GTG AAG GGC CGA TTC ACC ATC TCC AGA

        D   N   A   K   N   S   L   Y   L   Q   M   S   S   L   R   D   E   D
217    GAC AAT GCC AAG AAC TCA CTG TAT CTG CAA ATG AGC AGC CTG AGA GAC GAG GAC

                                                        CDR3
                                        ~~~~~~~~~~~~~~~~~~~~~~~~~~~~~~~~~~~~~~~
        T   A   V   Y   Y   C   A   G   T   V   T   T   Y   Y   Y   Y   F   G
271    ACG GCT GTG TAT TAC TGT GCG GGA ACT GTA ACG ACA TAT TAT TAT TAC TTC GGT
                                       |               |                  |
         CDR3                          |     D1-1      |                  |__>
       JH6b                            |_______________|
       ~~~~~~~~~~
        M   D   V   W   G   L   G   T   T   V   T   V   S   S
325    ATG GAC GTC TGG GGC CTA GGG ACC ACG GTC ACC GTC TCC TCA
```

*Figure 3A*

Anti-Fucosyl GM1 7D4 VK

V-segment: L15
    J-segment: JK4

```
          D   I   Q   M   T   Q   S   P   S   S   L   S   A   S   V   G   D   R
  1      GAC ATC CAG ATG ACC CAG TCT CCA TCC TCA CTG TCT GCA TCT GTA GGA GAC AGA
                                              CDR1
                                    ~~~~~~~~~~~~~~~~~~~~~~~~~~~~~~~~~~~~~~~~~~~
          V   T   I   T   C   R   A   S   Q   G   I   S   S   W   L   A   W   Y
 55      GTC ACC ATC ACT TGT CGG GCG AGT CAG GGT ATT AGC AGC TGG TTA GCC TGG TAT
                                                                      CDR2
                                                              ~~~~~~~~~~~~~~~~~~
          Q   Q   K   P   E   K   A   P   K   S   L   I   Y   A   A   S   S   L
109      CAG CAG AAA CCA GAG AAA GCC CCT AAG TCC CTG ATC TAT GCT GCA TCC AGT TTG
          CDR2
         ~~~~~~~~~
          Q   S   G   V   P   S   R   F   S   G   S   G   S   G   T   D   F   T
163      CAA AGT GGG GTC CCA TCA AGG TTC AGC GGC AGT GGA TCT GGG ACA GAT TTC ACT
                                                                          CDR3
                                                                      ~~~~~~~~~
          L   T   I   S   C   L   Q   P   E   D   F   A   T   Y   Y   C   Q   Q
217      CTC ACC ATC AGC TGC CTG CAG CCT GAA GAT TTT GCG ACT TAT TAC TGC CAA CAG
             CDR3
         ~~~~~~~~~~~~~~~~~~~~~~~~~~
          Y   N   S   Y   P   P   T   F   G   G   G   T   K   V   E   I   K
271      TAT AAT AGT TAC CCT CCC ACT TTC GGC GGA GGG ACC AAG GTG GAG ATC AAA
                          ↳ JK4
```

*Figure 3B*

Anti-Fucosyl GM1 7E4 VH

V-segment: VH3-48
D-segment: D1-1
J-segment: JH6b

```
         E   V   Q   L   V   E   S   G   G   G   S   V   Q   P   G   E   S   L
  1     GAA GTG CAG CTG GTG GAG TCT GGG GGA GGC TCG GTA CAG CCT GGG GAG TCC CTG

                                                              CDR 1
                                                         ~~~~~~~~~~~~~~~~~~~~
         R   L   S   C   V   A   S   G   F   T   F   S   R   Y   K   M   N   W
 55     AGA CTC TCC TGT GTA GCC TCT GGA TTC ACC TTC AGT AGG TAC AAG ATG AAC TGG

                                                                  CDR 2
                                                             ~~~~~~~~~~~~~~~~~~
         V   R   Q   A   P   G   K   G   L   E   W   V   S   Y   I   S   R   S
109     GTC CGC CAG GCT CCA GGG AAG GGA CTG GAA TGG GTT TCA TAC ATT AGT CGT AGT

                    CDR 2
        ~~~~~~~~~~~~~~~~~~~~~~~~~~~~~~~~~~~~~~~~~~~~~~~
         G   R   D   I   Y   Y   A   D   S   V   K   G   R   F   T   I   S   R
163     GGT CGT GAC ATA TAC TAC GCA GAC TCT GTG AAG GGC CGA TTC ACC ATC TCC AGA

         D   N   A   K   N   S   L   Y   L   Q   M   N   S   L   R   D   E   D
217     GAC AAT GCC AAG AAC TCA CTG TAT CTG CAA ATG AAC AGC CTG AGA GAC GAG GAC

                                                    CDR 3
                                        ~~~~~~~~~~~~~~~~~~~~~~~~~~~~~~~~~~~~~~~
         T   A   V   Y   Y   C   A   G   T   V   T   T   Y   Y   Y   D   F   G
271     ACG GCT GTG TAT TAC TGT GCG GGA ACT GTA ACG ACA TAC TAC TAC GAC TTC GGT
                                        |     D1-1     |  -> JH6b
         CDR 3
        ~~~~~~~~~~~~
         M   D   V   W   G   Q   G   T   T   V   T   V   S   S
325     ATG GAC GTC TGG GGC CAA GGG ACC ACG GTC ACC GTC TCC TCA
```

*Figure 4A*

```
Anti-Fucosyl GM1 7E4 VK

          V-segment:  L15
          J-segment:  JK4

          D   I   Q   M   T   Q   S   P   S   S   L   S   A   S   V   G   D   R
  3      GAC ATC CAG ATG ACC CAG TCT CCA TCC TCA CTG TCT GCA TCT GTA GGA GAC AGA

                                        CDR 1
                            ~~~~~~~~~~~~~~~~~~~~~~~~~~~~~~~~~~~~~~~~~~~~~
          V   T   I   T   C   R   A   S   Q   G   I   S   S   W   L   A   W   Y
 57      GTC ACC ATC ACT TGT CGG GCG AGT CAG GGT ATT AGC AGC TGG TTA GCC TGG TAT

                                                                  CDR 2
                                                          ~~~~~~~~~~~~~~~~~~~
          Q   Q   K   P   E   K   A   P   K   S   L   I   Y   A   A   S   S   L
111      CAG CAG AAA CCA GAG AAA GCC CCT AAG TCC CTG ATC TAT GCT GCA TCC AGT TTG

         CDR 2
         ~~~~~~~~
          Q   S   G   V   P   S   R   F   S   G   S   G   S   G   T   D   F   T
165      CAA AGT GGG GTC CCA TCA AGG TTC AGC GGC AGT GGA TCT GGG ACA GAT TTC ACT

                                                                      CDR 3
                                                                      ~~~~~~~
          L   T   I   S   S   L   Q   P   E   D   F   A   T   Y   Y   C   Q   Q
219      CTC ACC ATC AGC AGC CTG CAG CCT GAA GAT TTT GCA ACT TAT TAC TGC CAA CAG

                 CDR 3
         ~~~~~~~~~~~~~~~~~~~~~~~~~~~~~
          Y   N   S   Y   P   P   T   F   G   G   G   T   K   V   E   I   K
273      TAT AAT AGT TAC CCT CCC ACT TTC GGC GGA GGG ACC AAG GTG GAG ATC AAA
                                  JK4
```

*Figure 4B*

Anti-Fucosyl GM1 13B8 VH

V-segment: VH3-48
D-segment: D1-1
J-segment: JH6b

```
          E   V   Q   L   V   E   S   G   G   G   L   V   Q   P   G   E   S   L
  1      GAG GTG CAG CTG GTG GAG TCT GGG GGA GGC TTG GTA CAG CCT GGG GAG TCC CTG

                                                                 CDR1
                                                         ~~~~~~~~~~~~~~~~~~~~
          R   L   S   C   V   A   S   G   F   T   L   S   R   Y   K   M   N   W
 55      AGA CTC TCG TGT GTA GCC TCT GGA TTC ACC CTC AGT AGG TAT AAG ATG AAC TGG

                                                                     CDR2
                                                             ~~~~~~~~~~~~~~~~~~~
          V   R   Q   A   P   G   K   G   L   E   W   I   S   Y   I   S   R   S
109      GTC CGC CAG GCT CCA GGG AAG GGA CTG GAA TGG ATT TCA TAC ATC AGT CGT AGT

                         CDR2
         ~~~~~~~~~~~~~~~~~~~~~~~~~~~~~~~~~~~~~~~~~~~~~~~~
          G   R   D   I   Y   Y   A   D   S   V   K   G   R   F   T   I   S   R
163      GGT CGT GAC ATA TAC TAC GCA GAC TCT GTG AAG GGC CGA TTC ACC ATC TCC AGA

          D   N   A   K   N   S   L   Y   L   Q   M   N   S   L   R   D   E   D
217      GAC AAT GCC AAG AAC TCA CTG TAT CTG CAA ATG AAC AGC CTG CGA GAC GAG GAC

                                                      CDR3
                                         ~~~~~~~~~~~~~~~~~~~~~~~~~~~~~~~~~~~~~~~~
          S   A   V   Y   Y   C   A   G   T   V   T   T   Y   Y   Y   Y   F   G
271      TCG GCT GTG TAT TAC TGT GCG GGA ACT GTA ACG ACA TAC TAC TAC TAC TTC GGT
                                          |___ D1-1 ____|  |->
            CDR3                                                JH6b
         ~~~~~~~~~~~~
          M   D   V   W   G   Q   G   T   T   V   T   V   S   S
325      ATG GAC GTC TGG GGC CAA GGG ACC ACG GTC ACC GTC TCC TCA
```

*Figure 5A*

```
Anti-Fucosyl GM1 13B8 VK

          V-segment:  L15
          J-segment:  JK4


      D   I   Q   M   T   Q   S   P   S   S   L   S   A   S   V   G   D   R
  1  GAC ATC CAG ATG ACC CAG TCT CCA TCC TCA CTG TCT GCA TCT GTA GGA GAC AGA

                                      CDR1
                          ~~~~~~~~~~~~~~~~~~~~~~~~~~~~~~~~~~~~~~~~~~~~
      V   T   I   T   C   R   A   S   Q   G   I   S   S   W   L   A   W   Y
 55  GTC ACC ATC ACT TGT CGG GCG AGT CAG GGT ATT AGC AGC TGG TTA GCC TGG TAT

                                                            CDR2
                                                      ~~~~~~~~~~~~~~~~~~~
      Q   Q   K   P   E   K   A   P   K   S   L   I   Y   A   A   S   S   L
109  CAG CAG AAA CCA GAG AAA GCC CCT AAG TCC CTG ATC TAT GCT GCA TCC AGT TTG

      CDR2
     ~~~~~~~~
      Q   S   G   V   P   S   R   F   S   G   S   G   S   G   T   D   F   T
163  CAA AGT GGG GTC CCA TCA AGG TTC AGC GGC AGT GGA TCT GGG ACA GAT TTC ACT

                                                                    CDR3
                                                                  ~~~~~~~
      L   T   I   S   S   L   Q   P   E   D   F   A   T   Y   Y   C   Q   Q
217  CTC ACC ATC AGC AGC CTG CAG CCT GAA GAT TTT GCA ACT TAT TAC TGC CAA CAG

             CDR3
     ~~~~~~~~~~~~~~~~~~~~~~~~~~~~
      Y   N   S   Y   P   P   T   F   G   G   G   T   K   V   E   I   K
271  TAT AAT AGT TAC CCT CCC ACT TTC GGC GGA GGG ACC AAG GTG GAG ATC AAA
                         └→  JK4
```

*Figure 5B*

Anti-Fucosyl GM1 3C4 VH

V-segment: VH3-48
D-segment: D1-1
J-segment: JH6b

E V Q L V E S G G G L V Q P G E S L
1 GAG GTG CAG CTG GTG GAG TCT GGG GGA GGC TTG GTA CAG CCT GGG GAG TCC CTG

CDR1
R L S C V A S G F T F S R Y K M N W
55 AGA CTC TCC TGT GTA GCC TCT GGA TTC ACC TTC AGT AGG TAT AAG ATG AAC TGG

CDR2
V R Q A P G K G L E W I S Y I S R S
109 GTC CGC CAG GCT CCA GGG AAG GGA CTG GAA TGG ATT TCA TAC ATT AGT CGT AGT

CDR2
G R D I Y Y A D S V K G R F T I S R
163 GGT CGT GAC ATA TAC TAC GCA GAC TCT GTG AAG GGC CGA TTC ACC ATC TCC AGA

D N A K N S L Y L Q M S S L R D E D
217 GAC AAT GCC AAG AAC TCA CTG TAT CTG CAA ATG AGC AGC CTG AGA GAC GAG GAC

CDR3
T A V Y Y C A G T V T T Y Y Y Y F G
271 ACG GCT GTG TAT TAC TGT GCG GGA ACT GTC ACG ACA TAT TAT TAT TAC TTC GGT
D1-1
JH6b

CDR3
M D V W G L G T T V T V S S
325 ATG GAC GTC TGG GGC CTA GGG ACC ACG GTC ACC GTC TCC TCA

*Figure 6A*

Anti-Fucosyl GM1 3C4 VK

V-segment: L15
J-segment: JK4

```
          D   I   Q   M   T   Q   S   P   S   S   L   S   A   S   V   G   D   R
  1      GAC ATC CAG ATG ACC CAG TCT CCA TCC TCA CTG TCT GCA TCT GTA GGA GAC AGA

                                         CDR1
                             ~~~~~~~~~~~~~~~~~~~~~~~~~~~~~~~~~~~~~~~~~~~~
          V   T   I   T   C   R   A   S   Q   G   I   S   S   W   L   A   W   Y
 55      GTC ACC ATC ACT TGT CGG GCG AGT CAG GGT ATT AGC AGC TGG TTA GCC TGG TAT

                                                             CDR2
                                                         ~~~~~~~~~~~~~~~~~~~
          Q   Q   K   P   E   K   A   P   K   S   L   I   Y   A   A   S   S   L
109      CAG CAG AAA CCA GAG AAA GCC CCT AAG TCC CTG ATC TAT GCT GCA TCC AGT TTG

          CDR2
         ~~~~~~~~
          Q   S   G   V   P   S   R   F   S   G   S   G   S   G   T   D   F   T
163      CAA AGT GGG GTC CCA TCA AGG TTC AGC GGC AGT GGA TCT GGG ACA GAT TTC ACT

                                                                         CDR3
                                                                     ~~~~~~~
          L   T   I   S   C   L   Q   P   E   D   F   A   T   Y   Y   C   Q   Q
217      CTC ACC ATC AGC TGC CTG CAG CCT GAA GAT TTT GCG ACT TAT TAC TGC CAA CAG

                 CDR3
         ~~~~~~~~~~~~~~~~~~~~~~~~~~~~
          Y   N   S   Y   P   P   T   F   G   G   G   T   K   V   E   I   K
271      TAT AAT AGT TAC CCT CCC ACT TTC GGC GGA GGG ACC AAG GTG GAG ATC AAA
                              |
                              └→ JK4
```

*Figure 6B*

Anti-Fucosyl GM1 13B8, 18D5, 5B1, 7D4, 7E4 VH regions

```
3-48 germline   E V Q L V E S G G G L V Q P G G S L R L S C A A S G F T F S
13B8 VH         - - - - - - - - - - - - - - - E - - - - - - V - - - - - L -
18D5 VH         - - - - - - - - - - - - - - - E - - - - - - V - - - - - - -
5B1 VH          - - - - - - - - - - - - - - - E - - - - - - V - - - - - - -
5B1a VH         - - - - - - - - - - - - - - - E - - - - - - V - - - - - - -
7D4 VH          - - - - - - - - - - - - - - - E - - - - - - V V - - - - - -
7E4 VH          - - - - - - - - - - S - - - - E - - - - - - V - - - - - - -
                 __CDR1___                            _________CDR2__________
3-48 germline   S Y S M N W V R Q A P G K G L E W V S Y I S S S S S T I Y Y
13B8 VH         R - K - - - - - - - - - - - - - - I - - - - R - G R D - - -
18D5 VH         R - K - - - - - - - - - - - - - - I - - - - R - G R D - - -
5B1 VH          R - K - - - - - - - - - - - - - - - - - - - R - G R D - - -
5B1a VH         R - K - - - - - - - - - - - - - - - - - - - R - G R D - - -
7D4 VH          R - K - - - - - - - - - - - - - - I - - - - R - G R D - - -
7E4 VH          R - K - - - - - - - - - - - - - - - - - - - R - G R D - - -
                 __CDR2___
3-48 germline   A D S V K G R F T I S R D N A K N S L Y L Q M N S L R D E D
13B8 VH         - - - - - - - - - - - - - - - - - - - - - - - - - - - - - -
18D5 VH         - - - - - - - - - - - - - - - - - - - - - - - S - - - - - -
5B1 VH          - - - - - - - - - - - - - - - - - - - - - - - - - - - - - -
5B1a VH         - - - - - - - - - - - - - - - - - - - - - - - - - - - - - -
7D4 VH          - - - - - - - - - - - - - - - - - - - - - - - S - - - - - -
7E4 VH          - - - - - - - - - - - - - - - - - - - - - - - - - - - - - -
                               ________CDR3_________
3-48 germline   T A V Y Y C A R
13B8 VH         S - - - - - - G T V T T Y Y Y Y F G M D V W G Q G T T V T V
18D5 VH         - - - - - - - G T V T T Y Y Y Y F G M D V W G L G T T V T V
5B1 VH          - - - - - - - G T V T T Y Y Y Y F G M D V W G H G T T V T V
5B1a VH         - - - - - - - G T V T T * Y Y Y F G M D V W G H G T T V T V
7D4 VH          - - - - - - - G T V T T Y Y Y Y F G M D V W G L G T T V T V
7E4 VH          - - - - - - - G T V T T Y Y Y D F G M D V W G Q G T T V T V

13B8 VH         S S
18D5 VH         S S
5B1 VH          S S
5B1a VH         S S
7D4 VH          S S
7E4 VH          S S
```

*Fig. 7*

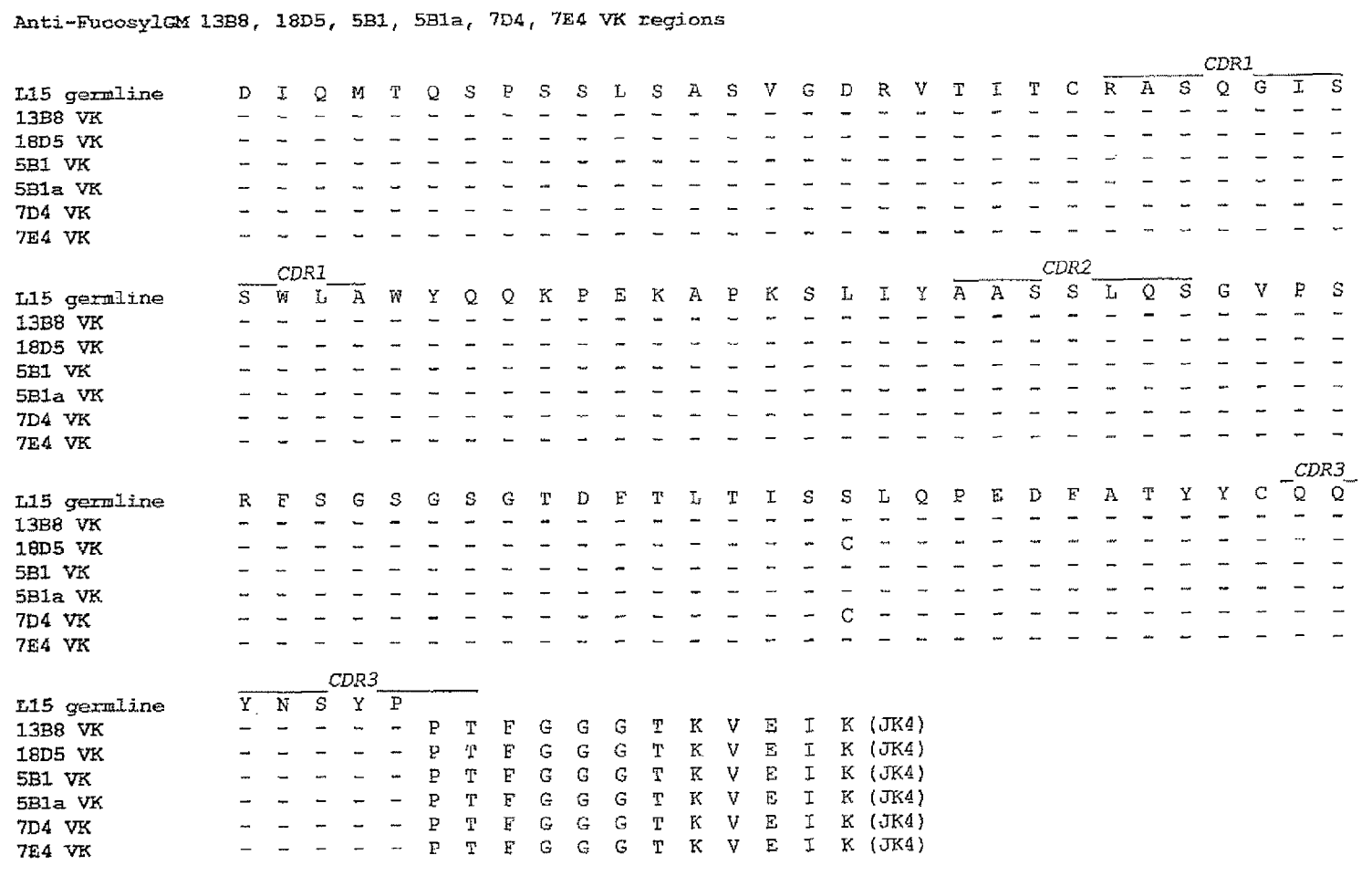

Anti-FucosylGM 13B8, 18D5, 5B1, 5B1a, 7D4, 7E4 VK regions

```
                                                                                    CDR1
                                                                              ___________________
L15 germline  D I Q M T Q S P S S L S A S V G D R V T I T C R A S Q G I S
13B8 VK       - - - - - - - - - - - - - - - - - - - - - - - - - - - - -
18D5 VK       - - - - - - - - - - - - - - - - - - - - - - - - - - - - -
5B1 VK        - - - - - - - - - - - - - - - - - - - - - - - - - - - - -
5B1a VK       - - - - - - - - - - - - - - - - - - - - - - - - - - - - -
7D4 VK        - - - - - - - - - - - - - - - - - - - - - - - - - - - - -
7E4 VK        - - - - - - - - - - - - - - - - - - - - - - - - - - - - -

               CDR1                                       CDR2
              _______                               _____________
L15 germline  S W L A W Y Q Q K P E K A P K S L I Y A A S S L Q S G V P S
13B8 VK       - - - - - - - - - - - - - - - - - - - - - - - - - - - - - -
18D5 VK       - - - - - - - - - - - - - - - - - - - - - - - - - - - - - -
5B1 VK        - - - - - - - - - - - - - - - - - - - - - - - - - - - - - -
5B1a VK       - - - - - - - - - - - - - - - - - - - - - - - - - - - - - -
7D4 VK        - - - - - - - - - - - - - - - - - - - - - - - - - - - - - -
7E4 VK        - - - - - - - - - - - - - - - - - - - - - - - - - - - - - -

                                                                CDR3
                                                                ___
L15 germline  R F S G S G S G T D F T L T I S S L Q P E D F A T Y Y C Q Q
13B8 VK       - - - - - - - - - - - - - - - - - - - - - - - - - - - - - -
18D5 VK       - - - - - - - - - - - - - - - - C - - - - - - - - - - - - -
5B1 VK        - - - - - - - - - - - - - - - - - - - - - - - - - - - - - -
5B1a VK       - - - - - - - - - - - - - - - - - - - - - - - - - - - - - -
7D4 VK        - - - - - - - - - - - - - - - - C - - - - - - - - - - - - -
7E4 VK        - - - - - - - - - - - - - - - - - - - - - - - - - - - - - -

                  CDR3
              ___________
L15 germline  Y N S Y P
13B8 VK       - - - - - P T F G G G T K V E I K (JK4)
18D5 VK       - - - - - P T F G G G T K V E I K (JK4)
5B1 VK        - - - - - P T F G G G T K V E I K (JK4)
5B1a VK       - - - - - P T F G G G T K V E I K (JK4)
7D4 VK        - - - - - P T F G G G T K V E I K (JK4)
7E4 VK        - - - - - P T F G G G T K V E I K (JK4)
```

*Fig. 8*

A.
Internalization Assay
H4-II-E Cells
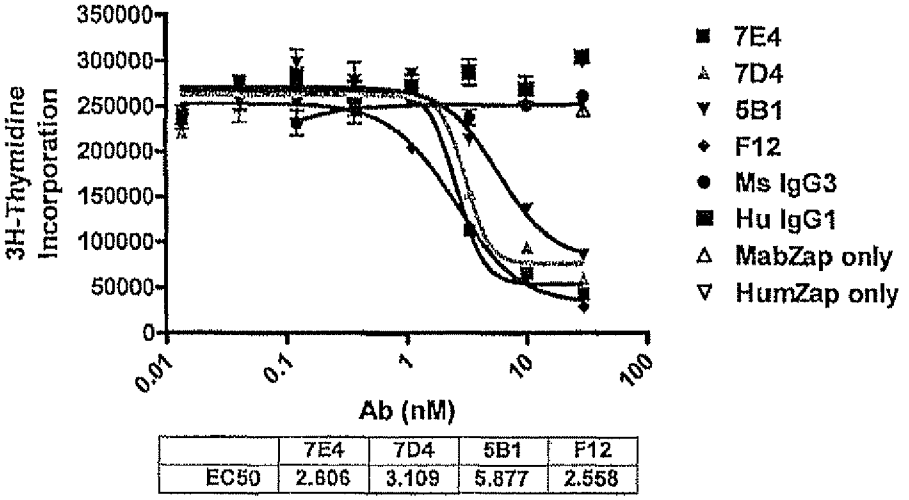
| | 7E4 | 7D4 | 5B1 | F12 |
|---|---|---|---|---|
| EC50 | 2.606 | 3.109 | 5.877 | 2.558 |
B.
Internalization Assay
DMS79 Cells
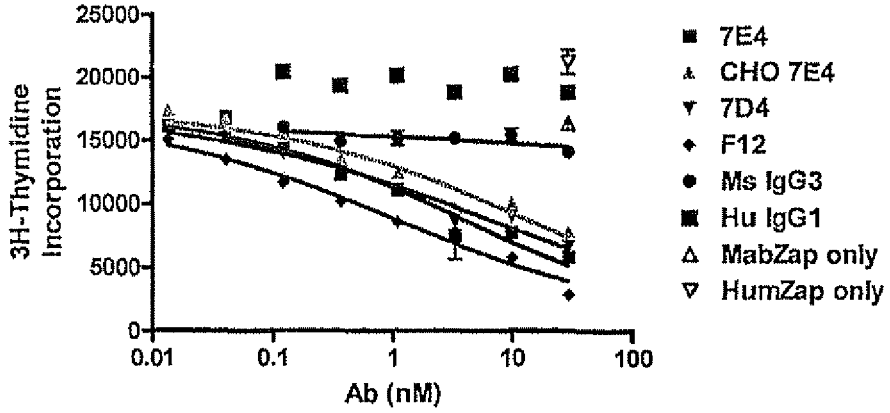
| | 7E4 | CHO 7E4 | 7D4 | F12 |
|---|---|---|---|---|
| EC50 | 4.049 | 13.80 | 6.692 | 1.105 |
*Fig. 12*

A.
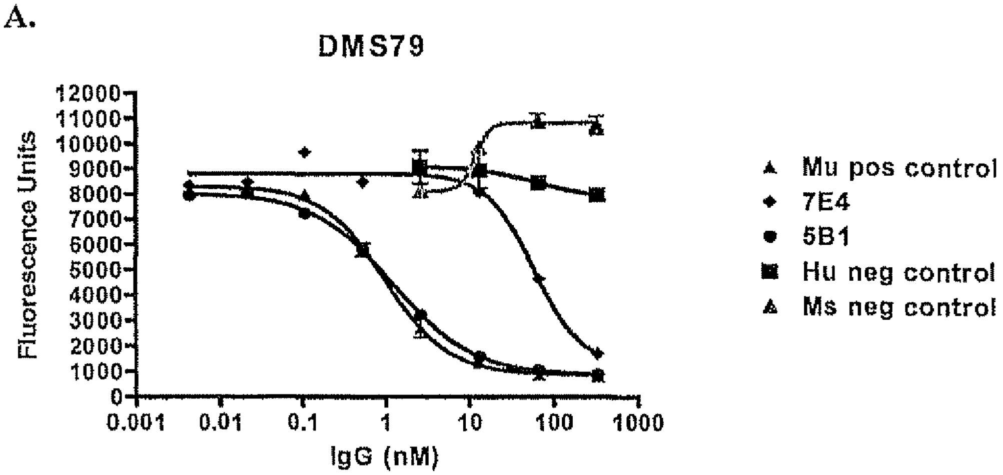
| | F12 | 7E4 | 5B1 |
|---|---|---|---|
| EC50 | 0.9833 | 58.88 | 1.231 |
B.
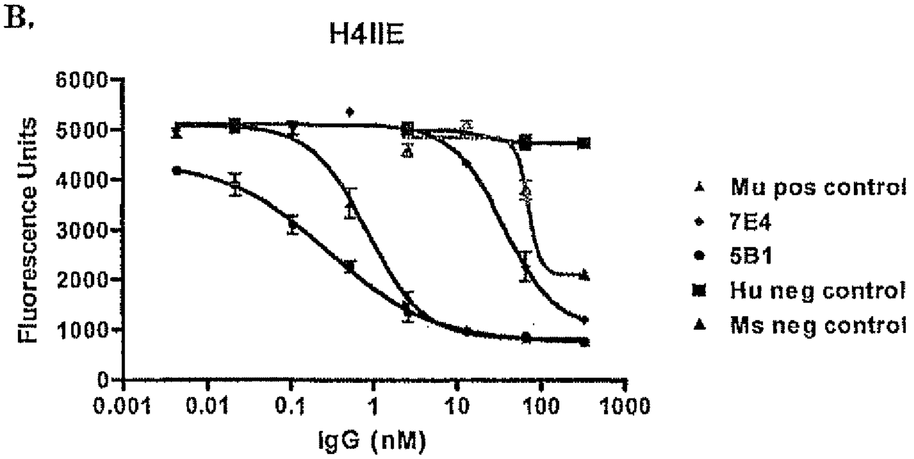
| | F12 | 7E4 | 5B1 |
|---|---|---|---|
| EC50 | 0.8727 | 36.73 | 0.2960 |
*Fig. 13*

A.
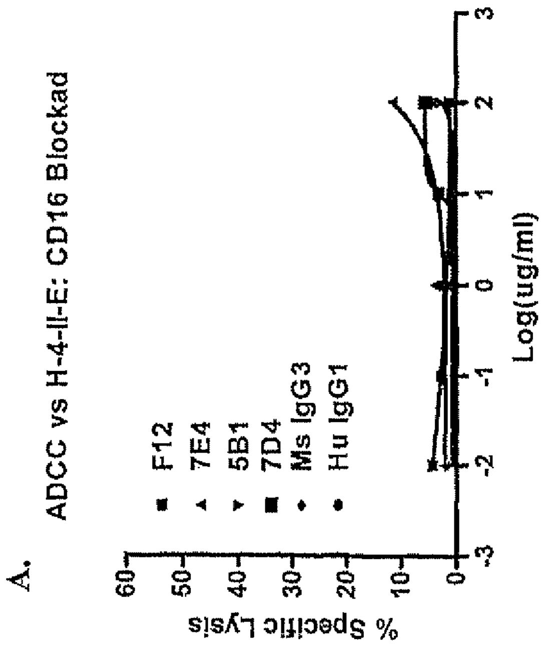
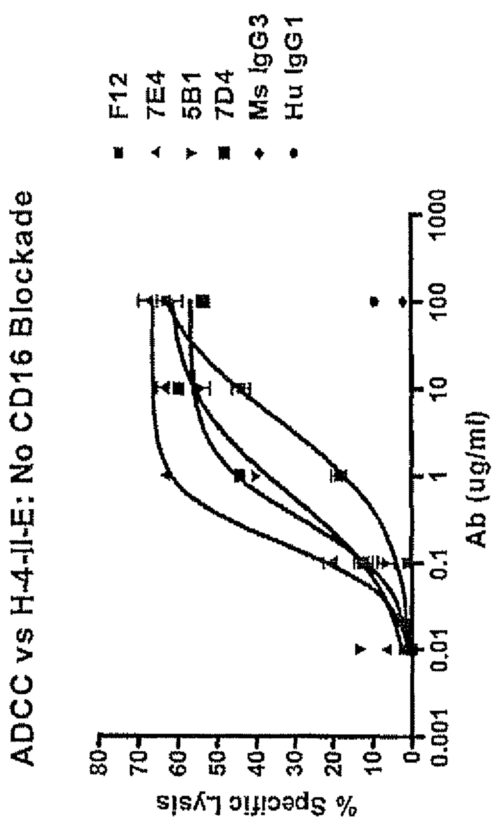
| | F12 | 7E4 | 5B1 | 7D4 |
|---|---|---|---|---|
| TOP | 69.01 | 66.38 | 62.58 | 56.84 |
| EC50 | 4.488 | 0.1667 | 0.6174 | 0.3205 |
*Fig. 14*

HUMAN MONOCLONAL ANTIBODIES TO FUCOSYL-GM1 AND METHODS FOR USING ANTI-FUCOSYL-GM1 ANTIBODIES

CROSS-REFERENCE TO RELATED APPLICATIONS

This application is a Divisional of U.S. 371 application Ser. No. 12/095,557, filed Jul. 22, 2010, now U.S. Pat. No. 8,383,118, issued Feb. 26, 2013, which is a national stage of International Application Serial No. PCT/US2006/061817, filed Dec. 8, 2006, which claims priority of U.S. Provisional Application Ser. No. 60/748,915, filed on Dec. 8, 2005, each of which is herein incorporated by reference in its entirety herein.

SEQUENCE LISTING

The specification further incorporates by reference the Sequence Listing submitted via EFS on Dec. 2, 2011 in U.S. application Ser. No. 12/095,557. Pursuant to 37 C.F.R. §1.52 (e)(5), the Sequence Listing text file, identified as "Medarex_ST25revised.txt," is 32,768 bytes and was created on Oct. 4, 2011. The Sequence Listing does not extend beyond the scope of the specification and thus does not contain new matter.

BACKGROUND

Fucosyl-GM1 is a sphingolipid monosialoganglioside composed of a ceramide lipid component, which anchors the molecule in the cell membrane, and a carbohydrate component tha is exposed at the cell surface. Carbohydrate antigens are the most abundantly expressed antigens on the cell surface of cancers (Feizi T. (1985) *Nature* 314:53-7). In some tumor types, such as small cell lung cancer (SCLC), initial responses to chemotherapy are impressive, but chemo-refractory relapses rapidly follows. Intervention with novel immunotherapeutics may succeed in overcoming drug resistant relapse (Johnson D H. (1995) *Lung Cancer* 12 Suppl 3:S71-5). Several carbohydrate antigens, such as gangliosides GD3 and GD2, have been shown to function as effective targets for passive immunotherapy with MAbs (Irie R F and Morton D L. (1986) *PNAS* 83:8694-8698; Houghton A N et al. (1985) PNAS 82:1242-1246). Ganglioside antigens have also been demonstrated to be effective targets for active immunotherapy with vaccines in clinical trials (Krug L M et al. (2004) *Clinical Cancer Research* 10:6094-6100; Dickler M N et al. (1999) *Clinical Cancer Research* 5:2773-2779; Livingston P O et al. (1994) *J Clin Oncol.* 12:1036-44). Indeed, serum derived from SCLC patients who developed antibody titers to Fucosyl-GM1 following vaccination with KLH conjugated antigen, demonstrated specific binding to tumor cells and tumor specific complement dependant cytotoxicity (CDC). Anti-Fucosyl-GM1 titer associated toxicities were mild and transient and three patients with limited-stage SCLC were relapse-free at 18, 24, and 30 months (Krug et al., supra; Dickler et al., supra).

Fucosyl-GM1 expression has been shown in a high percentage of SCLC cases and unlike other ganglioside antigens, Fucosyl-GM1 has little or no expression in normal tissues (Nilsson et al. (1984) *Glycoconjugate J* 1:43-9; Krug et al., supra; Brezicka et al. (1989) *Cancer Res* 49:1300-5; Zhangyi et al. (1997) *Int J Cancer* 73:42-49; Brezicka et al. (2000) *Lung Cancer* 28:29-36; Fredman et al. (1986) *Biochim Biophys Acta* 875: 316-23; Brezicka et al. (1991) *APMIS* 99:797-802; Nilsson et al. (1986) *Cancer Res* 46:1403-7). The presence of Fucosyl-GM1 has been demonstrated in culture media from SCLC cell lines, in tumor extracts and serum of nude mouse xenografts and in the serum of SCLC patients with extensive-stage disease (Vangsted et al. (1991) *Cancer Res* 51:2879-84; Vangsted et al. (1994) *Cancer Detect Prev* 18:221-9). These reports provide convincing evidence for Fucosyl-GM1 as a highly specific tumor antigen, which may be targeted by an immunotherapeutic.

Accordingly, agents that recognize Fucosyl-GM1, and methods of using such agents, are desired.

SUMMARY

The present disclosure provides isolated monoclonal antibodies, in particular human monoclonal antibodies, that bind to Fucosyl-GM1 and that exhibit numerous desirable properties. These properties include high affinity binding to Fucosyl-GM1 and binding to the human small cell lung cancer cell line DMS-79 (Human SCLC ATCC #CRL-2049). Also provided are methods for treating a variety of Fucosyl-GM1 mediated diseases using the antibodies and compositions of this disclosure.

In one aspect, this disclosure pertains to an isolated monoclonal antibody, or an antigen-binding portion thereof, wherein the antibody (a) specifically binds to Fucosyl-GM1; and (b) binds to the human small cell lung cancer cell line DMS-79 (Human SCLC ATCC #CRL-2049).

Preferably the antibody is a human antibody, although in alternative embodiments the antibody can be a murine antibody, a chimeric antibody or humanized antibody.

In another embodiment, this disclosure provides an isolated monoclonal antibody, or antigen binding portion thereof, wherein the antibody cross-competes for binding to Fucosyl-GM1 with a reference antibody, wherein the reference antibody (a) specifically binds to Fucosyl-GM1; and (b) binds to the human small cell lung cancer cell line DMS-79 (Human SCLC ATCC #CRL-2049). In certain embodiments, the reference antibody comprises: (a) a heavy chain variable region comprising the amino acid sequence of SEQ ID NO:1; and (b) a light chain variable region comprising the amino acid sequence of SEQ ID NO:7. In further embodiments, the reference antibody comprises: (a) a heavy chain variable region comprising the amino acid sequence of SEQ ID NO:2; and (b) a light chain variable region comprising the amino acid sequence of SEQ ID NO:8. In other embodiments, the reference antibody comprises: (a) a heavy chain variable region comprising the amino acid sequence of SEQ ID NO:3; and (b) a light chain variable region comprising the amino acid sequence of SEQ ID NO:9. In still further embodiments, the reference antibody comprises: (a) a heavy chain variable region comprising the amino acid sequence of SEQ ID NO:4; and (b) a light chain variable region comprising the amino acid sequence of SEQ ID NO:10. In yet further embodiments, the reference antibody comprises: (a) a heavy chain variable region comprising the amino acid sequence of SEQ ID NO:5; and (b) a light chain variable region comprising the amino acid sequence of SEQ ID NO:11. In even further embodiments, the reference antibody comprises: (a) a heavy chain variable region comprising the amino acid sequence of SEQ ID NO:6; and (b) a light chain variable region comprising the amino acid sequence of SEQ ID NO:12.

In one aspect, this disclosure pertains to an isolated monoclonal antibody, or an antigen-binding portion thereof, comprising a heavy chain variable region that is the product of or derived from a human $V_H$ 3-48 gene, wherein the antibody specifically binds Fucosyl-GM1. This disclosure further provides an isolated monoclonal antibody, or an antigen-binding portion thereof, comprising a light chain variable region that is the product of or derived from a human $V_K$ L15 gene, wherein the antibody specifically binds Fucosyl-GM1.

A preferred combination comprises:

(a) a heavy chain variable region CDR1 comprising SEQ ID NO:13;
(b) a heavy chain variable region CDR2 comprising SEQ ID NO:19;
(c) a heavy chain variable region CDR3 comprising SEQ ID NO:25;
(d) a light chain variable region CDR1 comprising SEQ ID NO:31;
(e) a light chain variable region CDR2 comprising SEQ ID NO:37; and
(f) a light chain variable region CDR3 comprising SEQ ID NO:43.

Another preferred combination comprises:

(a) a heavy chain variable region CDR1 comprising SEQ ID NO:14;
(b) a heavy chain variable region CDR2 comprising SEQ ID NO:20;
(c) a heavy chain variable region CDR3 comprising SEQ ID NO:26;
(d) a light chain variable region CDR1 comprising SEQ ID NO:32;
(e) a light chain variable region CDR2 comprising SEQ ID NO:38; and
(f) a light chain variable region CDR3 comprising SEQ ID NO:44.

Another preferred combination comprises:

(a) a heavy chain variable region CDR1 comprising SEQ ID NO:15;
(b) a heavy chain variable region CDR2 comprising SEQ ID NO:21;
(c) a heavy chain variable region CDR3 comprising SEQ ID NO:27;
(d) a light chain variable region CDR1 comprising SEQ ID NO:33;
(e) a light chain variable region CDR2 comprising SEQ ID NO:39; and
(f) a light chain variable region CDR3 comprising SEQ ID NO:45.

Another preferred combination comprises:

(a) a heavy chain variable region CDR1 comprising SEQ ID NO:16;
(b) a heavy chain variable region CDR2 comprising SEQ ID NO:22;
(c) a heavy chain variable region CDR3 comprising SEQ ID NO:28;
(d) a light chain variable region CDR1 comprising SEQ ID NO:34;
(e) a light chain variable region CDR2 comprising SEQ ID NO:40; and
(f) a light chain variable region CDR3 comprising SEQ ID NO:46.

Another preferred combination comprises:

(a) a heavy chain variable region CDR1 comprising SEQ ID NO:17;
(b) a heavy chain variable region CDR2 comprising SEQ ID NO:23;
(c) a heavy chain variable region CDR3 comprising SEQ ID NO:29;
(d) a light chain variable region CDR1 comprising SEQ ID NO:35;
(e) a light chain variable region CDR2 comprising SEQ ID NO:41; and
(f) a light chain variable region CDR3 comprising SEQ ID NO:47.

Another preferred combination comprises:

(a) a heavy chain variable region CDR1 comprising SEQ ID NO:18;
(b) a heavy chain variable region CDR2 comprising SEQ ID NO:24;
(c) a heavy chain variable region CDR3 comprising SEQ ID NO:30;
(d) a light chain variable region CDR1 comprising SEQ ID NO:36;
(e) a light chain variable region CDR2 comprising SEQ ID NO:42; and
(f) a light chain variable region CDR3 comprising SEQ ID NO:48.

Other preferred antibodies of this disclosure, or antigen binding portions thereof comprise:

(a) a heavy chain variable region comprising the amino acid sequence of SEQ ID NO:1; and
(b) a light chain variable region comprising the amino acid sequence of SEQ ID NO:7.

Another preferred combination comprises:

(a) a heavy chain variable region comprising the amino acid sequence of SEQ ID NO:2; and
(b) a light chain variable region comprising the amino acid sequence of SEQ ID NO:8.

Another preferred combination comprises:

(a) a heavy chain variable region comprising the amino acid sequence of SEQ ID NO:3; and
(b) a light chain variable region comprising the amino acid sequence of SEQ ID NO:9.

Another preferred combination comprises:

(a) a heavy chain variable region comprising the amino acid sequence of SEQ ID NO:4; and
(b) a light chain variable region comprising the amino acid sequence of SEQ ID NO:10.

Another preferred combination comprises:

(a) a heavy chain variable region comprising the amino acid sequence of SEQ ID NO:5; and
(b) a light chain variable region comprising the amino acid sequence of SEQ ID NO:11.

Another preferred combination comprises:

(a) a heavy chain variable region comprising the amino acid sequence of SEQ ID NO:6; and
(b) a light chain variable region comprising the amino acid sequence of SEQ ID NO:12.

The antibodies of this disclosure can be, for example, full-length antibodies, for example of an IgG1 or IgG4 isotype. Alternatively, the antibodies can be antibody fragments, such as Fab or Fab'2 fragments, or single chain antibodies.

This disclosure also provides an immunoconjugate comprising an antibody of this disclosure, or antigen-binding portion thereof, linked to a therapeutic agent, such as a cytotoxin or a radioactive isotope. This disclosure also provides a bispecific molecule comprising an antibody, or antigen-binding portion thereof, of this disclosure, linked to a second functional moiety having a different binding specificity than said antibody, or antigen binding portion thereof.

Compositions comprising an antibody, or antigen-binding portion thereof, or immunoconjugate or bispecific molecule of this disclosure and a pharmaceutically acceptable carrier are also provided.

Nucleic acid molecules encoding the antibodies, or antigen-binding portions thereof, of this disclosure are also encompassed by this disclosure, as well as expression vectors comprising such nucleic acids and host cells comprising such expression vectors. Moreover, this disclosure provides a transgenic mouse comprising human immunoglobulin heavy and light chain transgenes, wherein the mouse expresses an antibody of this disclosure, as well as hybridomas prepared from such a mouse, wherein the hybridoma produces the antibody of this disclosure.

In yet another aspect, this disclosure provides a method of treating or preventing a disease characterized by growth of tumor cells expressing Fucosyl-GM1, comprising administering to the subject the antibody, or antigen-binding portion thereof, of this disclosure in an amount effective to treat or prevent the disease. The disease can be, for example, cancer, e.g., lung cancer (including small cell lung cancer).

In a preferred embodiment, this disclosure provides a method of treating cancer in vivo using an anti-Fucosyl-GM1 antibody. The anti-Fucosyl-GM1 antibody may be a murine, chimeric, humanized or human antibody. Examples of other cancers that may be treated using the methods of this disclosure include lung cancer, including small cell lung cancer and non-small cell lung cancer, renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Other features and advantages of the instant disclosure will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:49) and amino acid sequence (SEQ ID NO:1) of the heavy chain variable region of the 5B1 human monoclonal antibody. The CDR1 (SEQ ID NO:13), CDR2 (SEQ ID NO:19) and CDR3 (SEQ ID NO:25) regions are delineated and the V, D and J germline derivations are indicated.

FIG. 1B shows the nucleotide sequence (SEQ ID NO:55) and amino acid sequence (SEQ ID NO:7) of the light chain variable region of the 5B1 human monoclonal antibody. The CDR1 (SEQ ID NO:31), CDR2 (SEQ ID NO:37) and CDR3 (SEQ ID NO:43) regions are delineated and the V and J germline derivations are indicated.

FIG. 2A shows the nucleotide sequence (SEQ ID NO:50) and amino acid sequence (SEQ ID NO:2) of the heavy chain variable region of the 5B1a human monoclonal antibody. The CDR1 (SEQ ID NO:14), CDR2 (SEQ ID NO:20) and CDR3 (SEQ ID NO:26) regions are delineated and the V, D and J germline derivations are indicated.

FIG. 2B shows the nucleotide sequence (SEQ ID NO:56) and amino acid sequence (SEQ ID NO:8) of the light chain variable region of the 5B1a human monoclonal antibody. The CDR1 (SEQ ID NO:32), CDR2 (SEQ ID NO:38) and CDR3 (SEQ ID NO:44) regions are delineated and the V and J germline derivations are indicated.

FIG. 3A shows the nucleotide sequence (SEQ ID NO:51) and amino acid sequence (SEQ ID NO:3) of the heavy chain variable region of the 7D4 human monoclonal antibody. The CDR1 (SEQ ID NO:15), CDR2 (SEQ ID NO:21) and CDR3 (SEQ ID NO:27) regions are delineated and the V, D and J germline derivations are indicated.

FIG. 3B shows the nucleotide sequence (SEQ ID NO:57) and amino acid sequence (SEQ ID NO:9) of the light chain variable region of the 7D4 human monoclonal antibody. The CDR1 (SEQ ID NO:33), CDR2 (SEQ ID NO:39) and CDR3 (SEQ ID NO:45) regions are delineated and the V and J germline derivations are indicated.

FIG. 4A shows the nucleotide sequence (SEQ ID NO:52) and amino acid sequence (SEQ ID NO:4) of the heavy chain variable region of the 7E4 human monoclonal antibody. The CDR1 (SEQ ID NO:16), CDR2 (SEQ ID NO:22) and CDR3 (SEQ ID NO:28) regions are delineated and the V, D and J germline derivations are indicated.

FIG. 4B shows the nucleotide sequence (SEQ ID NO:58) and amino acid sequence (SEQ ID NO:10) of the light chain variable region of the 7E4 human monoclonal antibody. The CDR1 (SEQ ID NO:34), CDR2 (SEQ ID NO:40) and CDR3 (SEQ ID NO:46) regions are delineated and the V and J germline derivations are indicated.

FIG. 5A shows the nucleotide sequence (SEQ ID NO:53) and amino acid sequence (SEQ ID NO:5) of the heavy chain variable region of the 13B8 human monoclonal antibody. The CDR1 (SEQ ID NO:17), CDR2 (SEQ ID NO:23) and CDR3 (SEQ ID NO:29) regions are delineated and the V, D and J germline derivations are indicated.

FIG. 5B shows the nucleotide sequence (SEQ ID NO:59) and amino acid sequence (SEQ ID NO:11) of the light chain variable region of the 13B8 human monoclonal antibody. The CDR1 (SEQ ID NO:35), CDR2 (SEQ ID NO:41) and CDR3 (SEQ ID NO:47) regions are delineated and the V and J germline derivations are indicated.

FIG. 6A shows the nucleotide sequences (SEQ ID NO:54) and amino acid sequence (SEQ ID NO:63) of the heavy chain variable region of the 3C4 human monoclonal antibody. The CDR1 (SEQ ID NO:65), CDR2 (SEQ ID NO:66) and CDR3 (SEQ ID NO:67) regions are delineated and the V, D and J germline derivations are indicated.

FIG. 6B shows the nucleotide sequence (SEQ ID NO:60) and amino acid sequence (SEQ ID NO:64) of the light chain variable region of the 3C4 human monoclonal antibody. The CDR1 (SEQ ID NO:68), CDR2 (SEQ ID NO:69) and CDR3

(SEQ ID NO:70) regions are delineated and the V and J germline derivations are indicated.

FIG. 7 shows the alignment of the amino acid sequences of the heavy chain variable regions of 5B1, 5B1a, 7D4, 7E4, 13B8 and 18D5 with the human germline $V_H$3-48 amino acid sequence (SEQ ID NO:61).

FIG. 8 shows the alignment of the amino acid sequences of the light chain variable regions of 5B1, 5B1a, 7D4, 7E4, 13B8 and 18D5 with the human germline $V_k$ L15 amino acid sequence (SEQ ID NO:62).

Figure 9A:
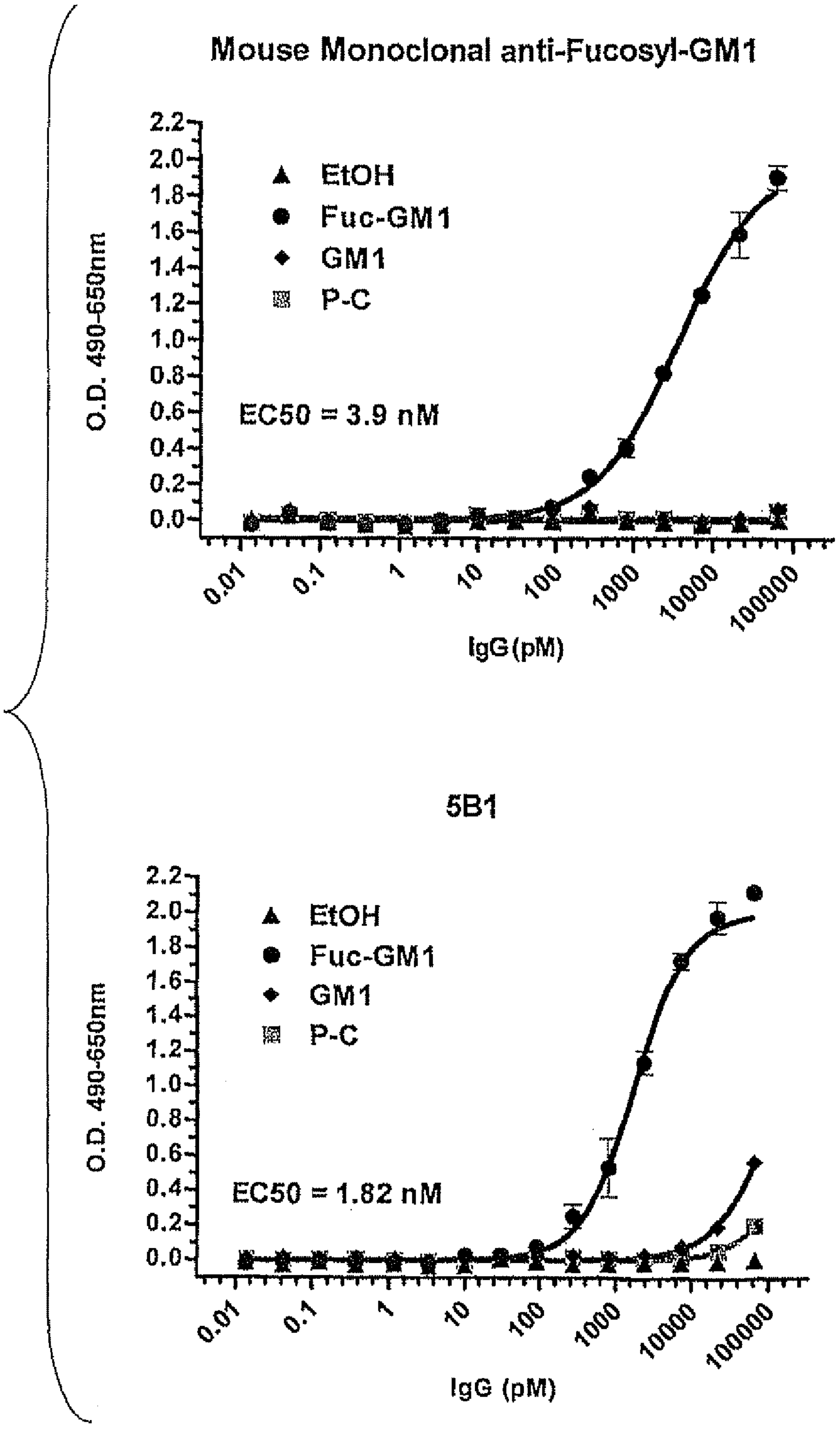
Figure 9B:
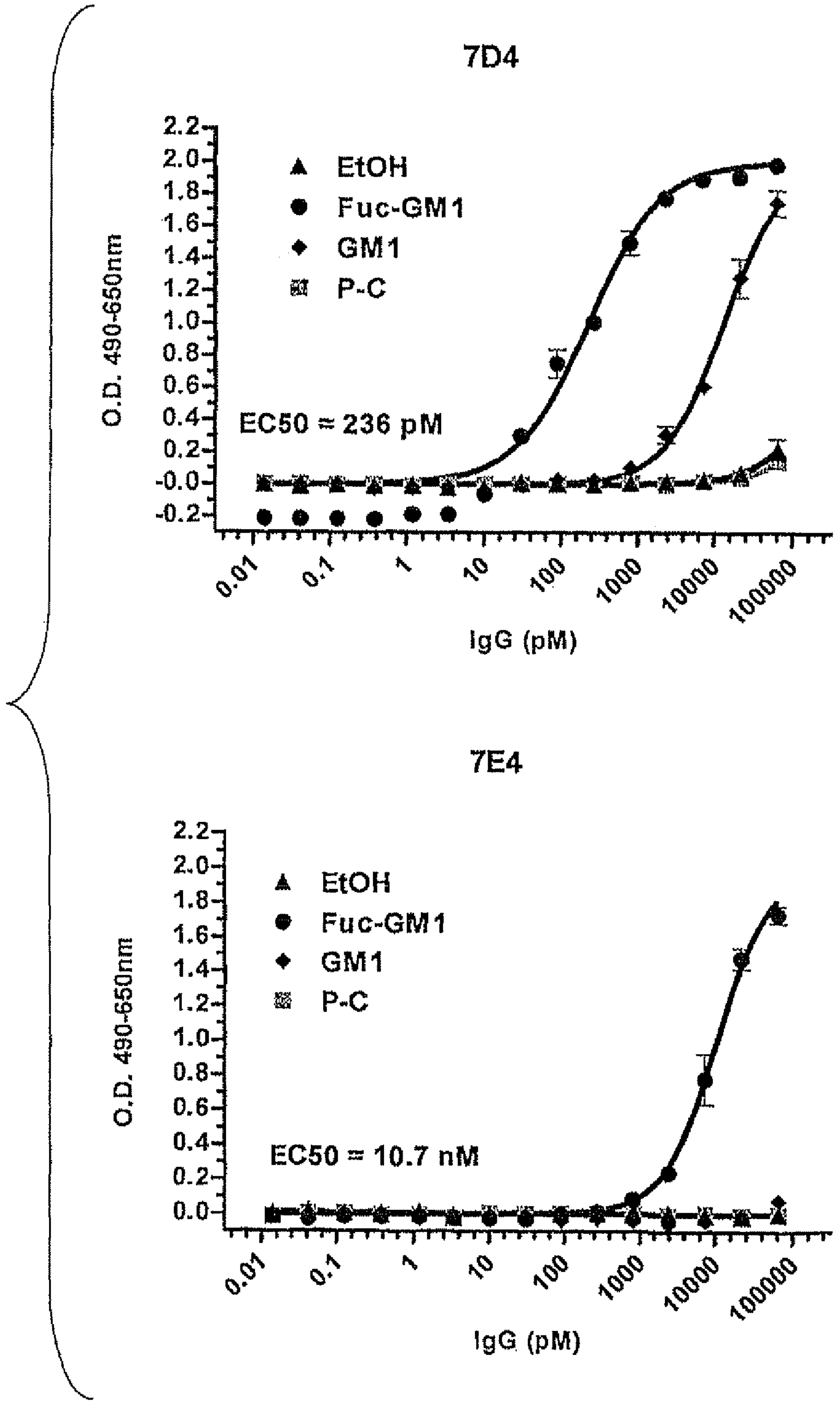
Figure 9C:
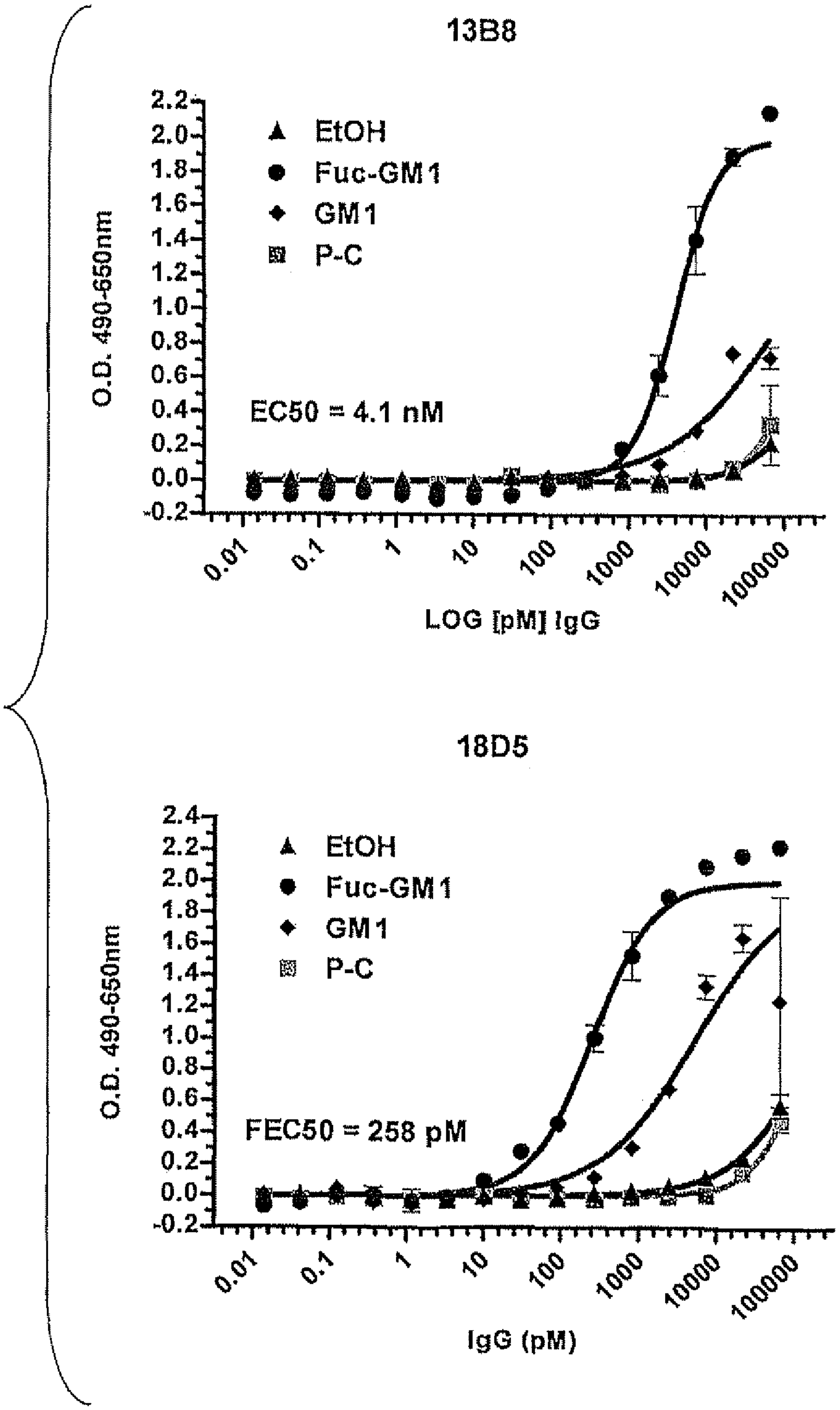

FIGS. 9A-C show the results of ELISA experiments demonstrating that human monoclonal antibodies against Fucosyl-GM1 specifically bind to Fucosyl-GM1.

Figure 10A:
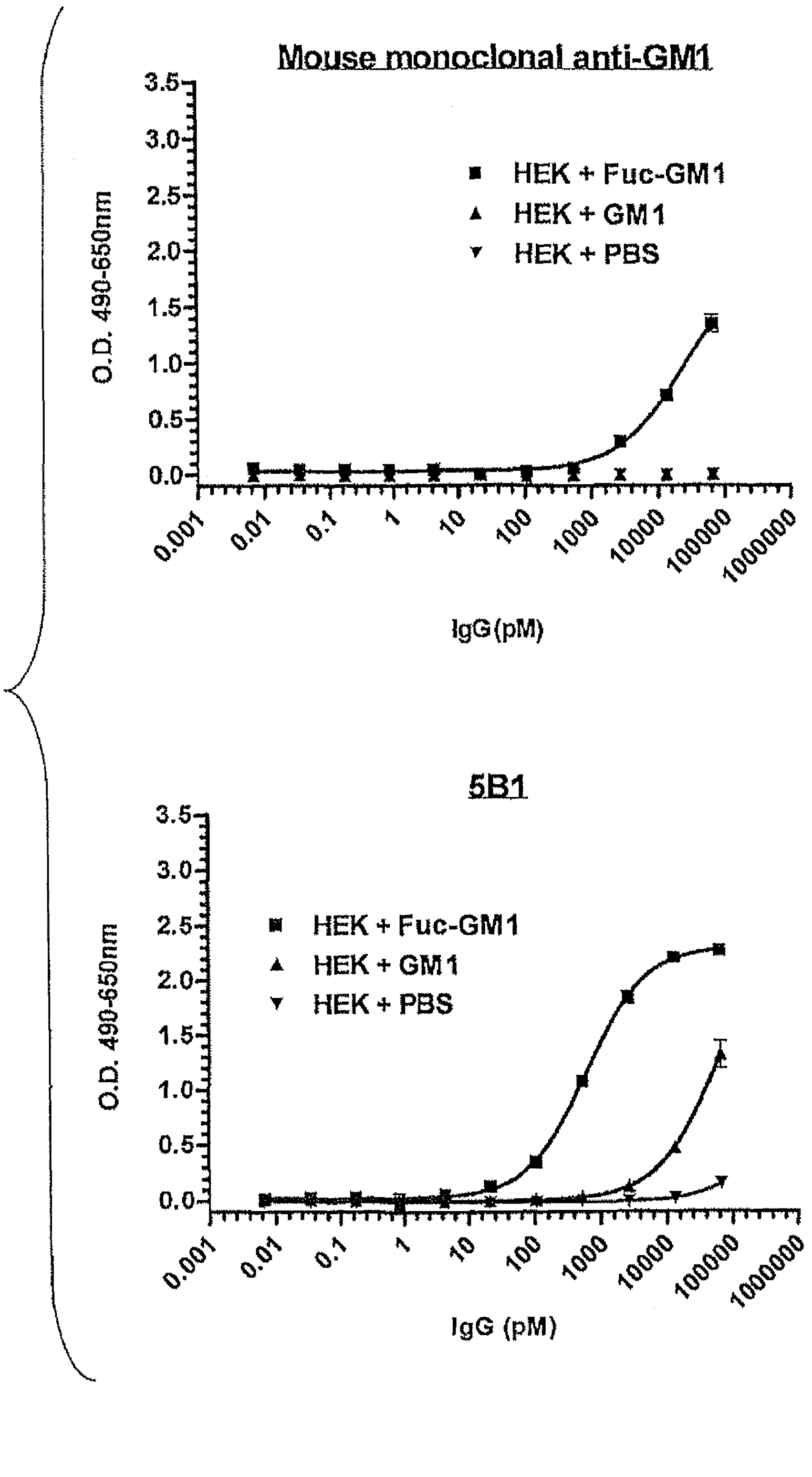
Figure 10B:
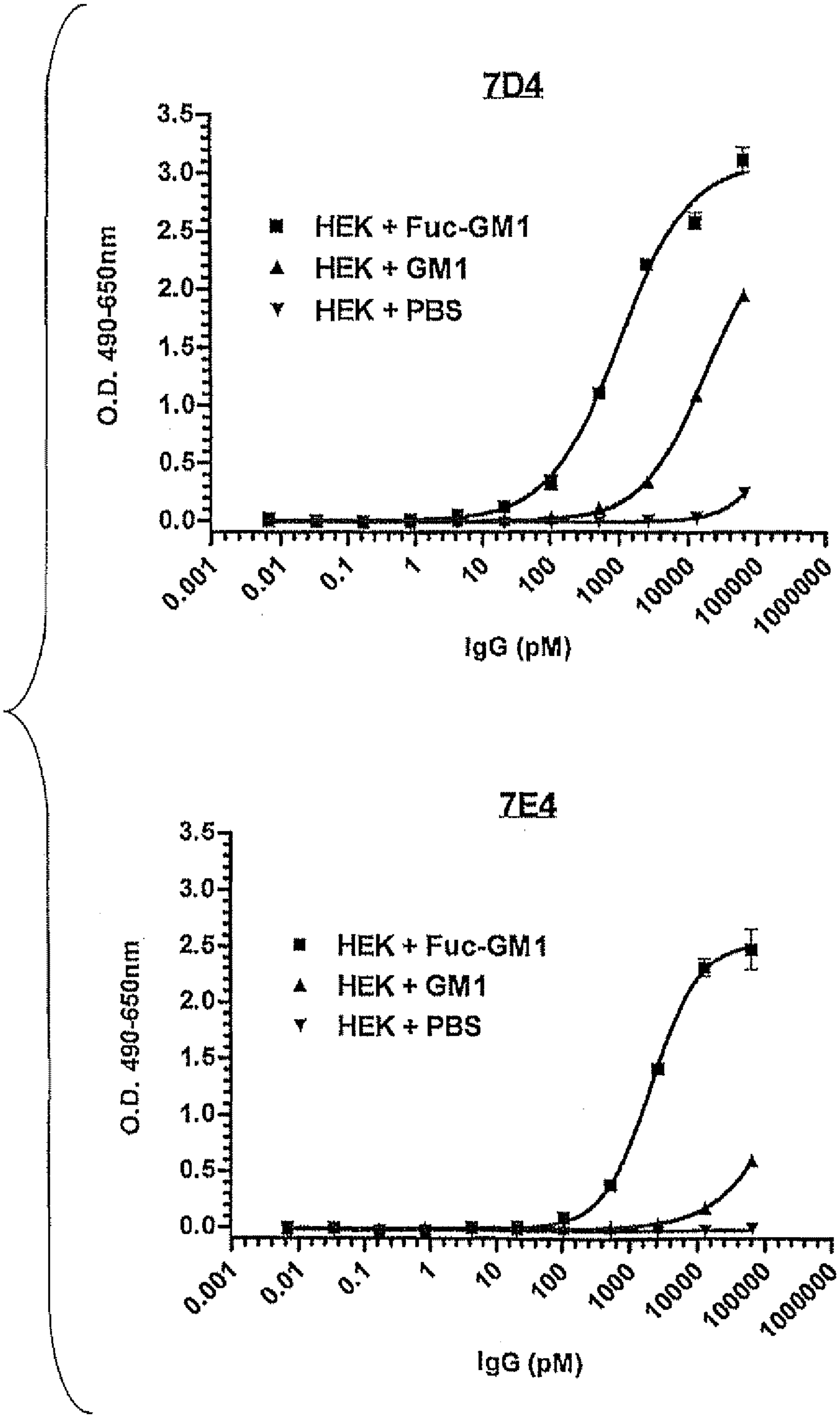
Figure 10C:
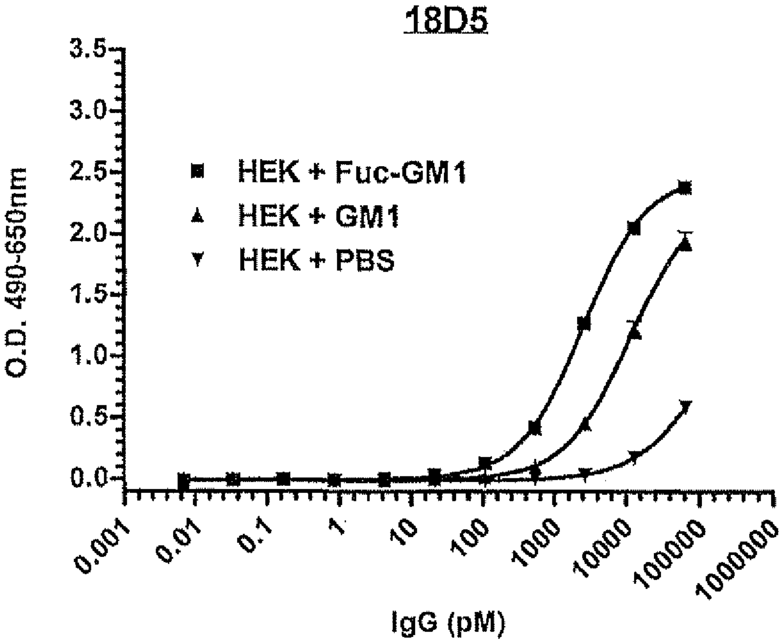

FIGS. 10A-C show the results of whole-cell ELISA experiments demonstrating that human monoclonal antibodies against Fucosyl-GM1 specifically bind to cells expressing Fucosyl-GM1.

Figure 11A:
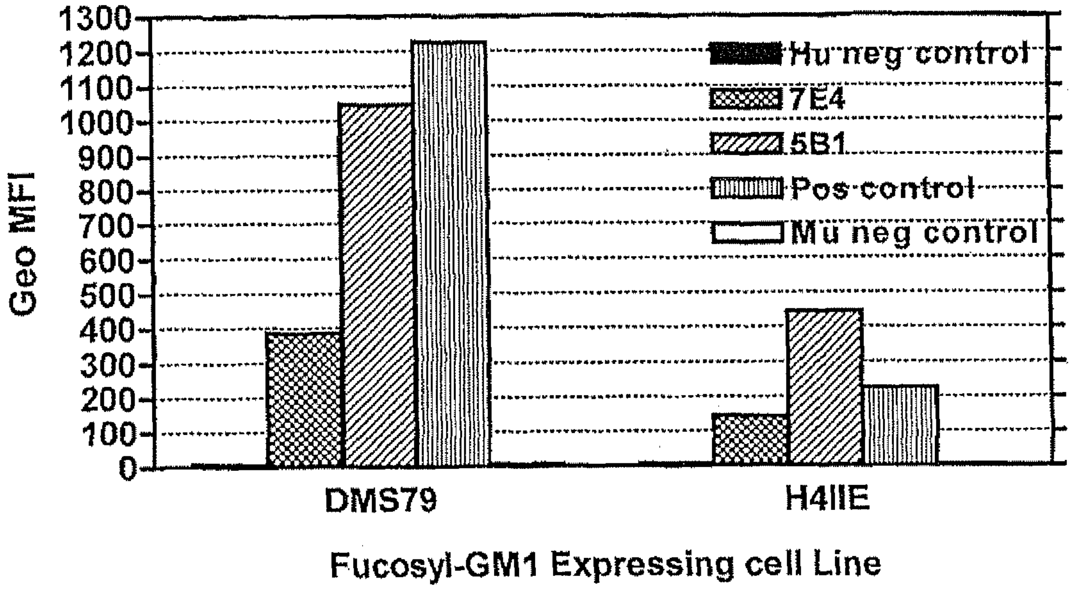
Figure 11B:
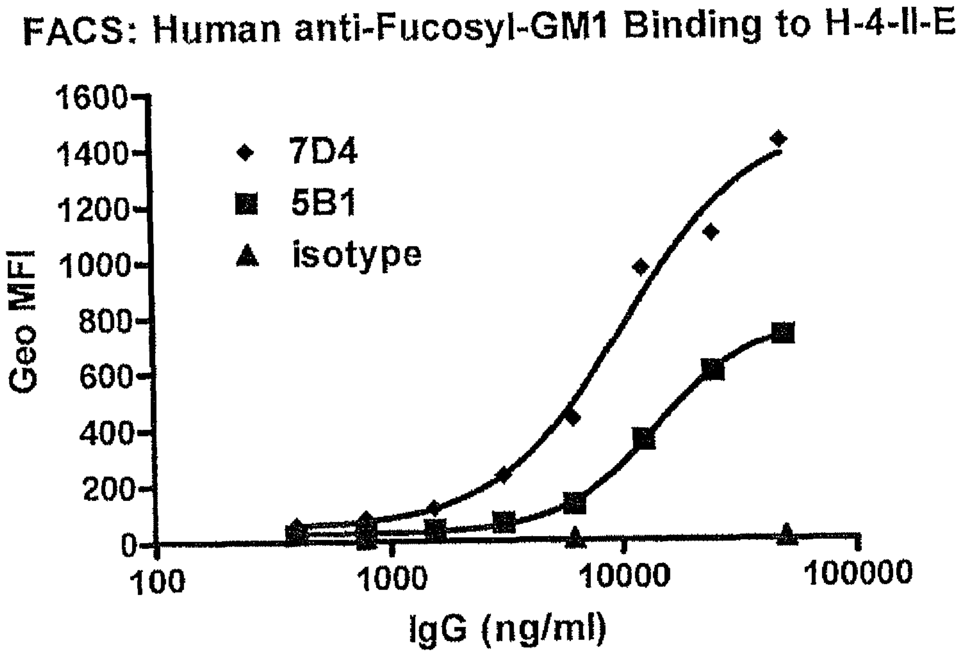
Figure 11C:
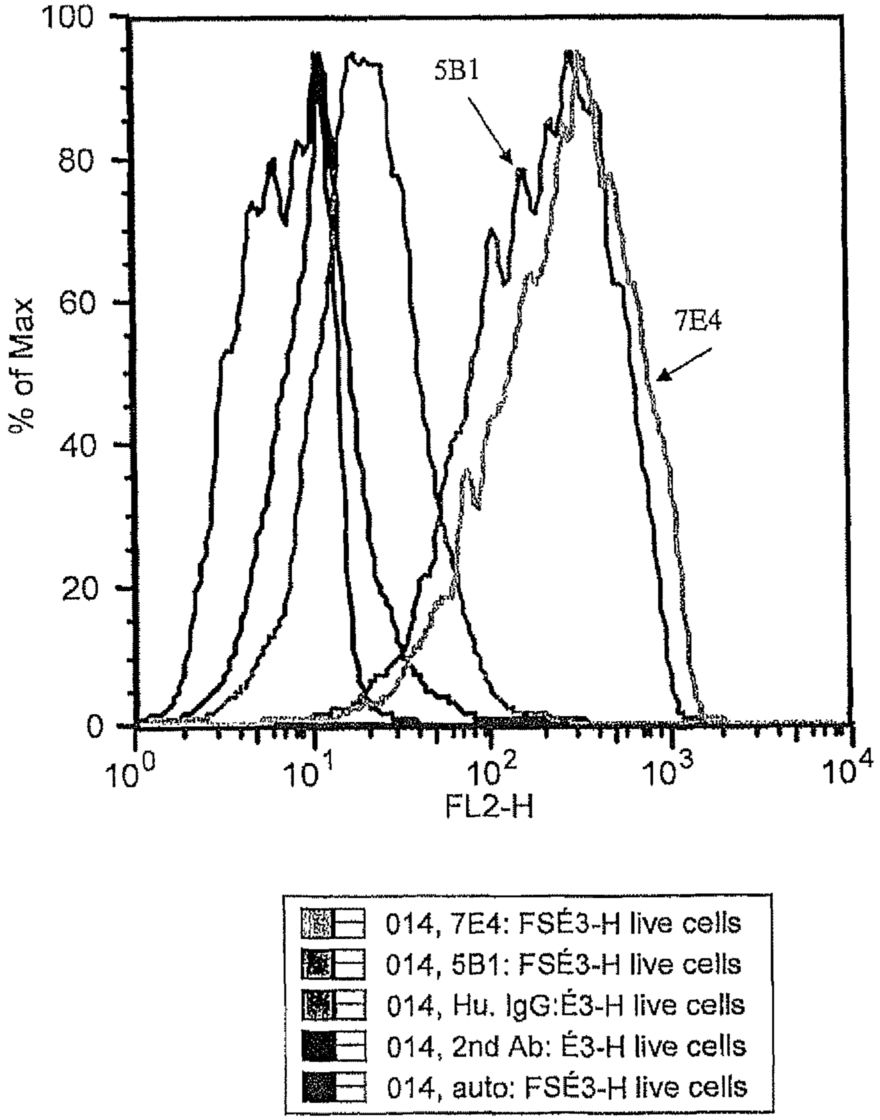

FIGS. 11A-C show the results of flow cytometry experiments demonstrating that (A and B) the human monoclonal antibodies against Fucosyl-GM1 bind the cell surface of cell lines DMS79 and H-4-II-E expressing Fucosyl-GM1, and that (C) the DMS79 cells were found to continue expressing Fucosyl-GM1 in vivo (i.e., after implantation in a mouse).

FIGS. 12A and B show the results of Hum-Zap internalization experiments demonstrating that human monoclonal antibodies against Fucosyl-GM1 can internalize into Fucosyl-GM1+ cells.

FIGS. 13A and B show the results of a complement dependent cytotoxicity (CDC) cell proliferation assay demonstrating that human monoclonal anti-Fucosyl-GM1 antibodies kill cell lines (A) DMS79 and (B) H-4-II-E that express Fucosyl-GM1.

FIGS. 14A and B show the results of an antibody dependent cell cytotoxicity (ADCC) cell proliferation assay demonstrating that human monoclonal anti-Fucosyl-GM1 antibodies kill cell lines expressing Fucosyl-GM1 in the absence of CD16 blockade.

Figure 15A:
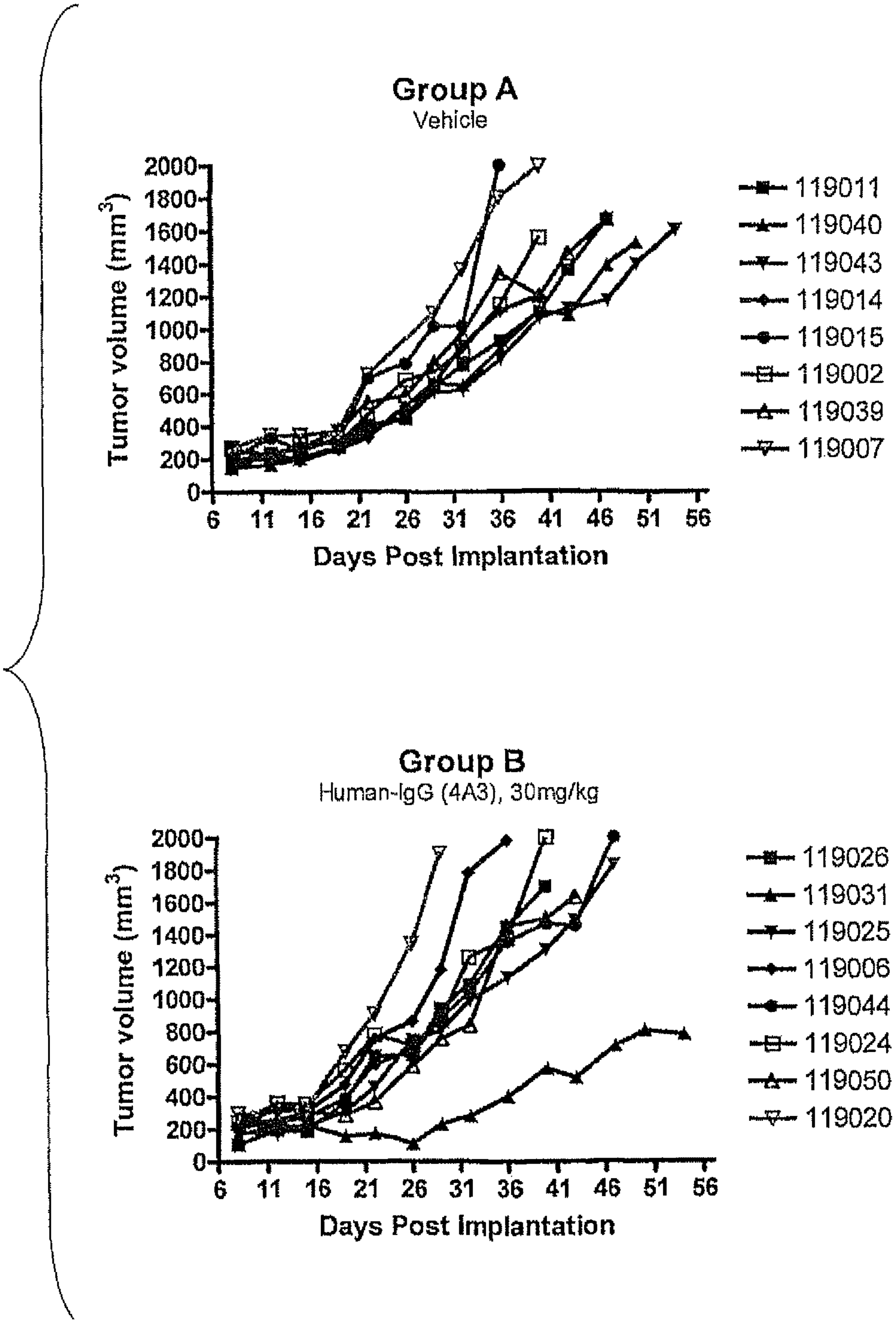
Figure 15B:
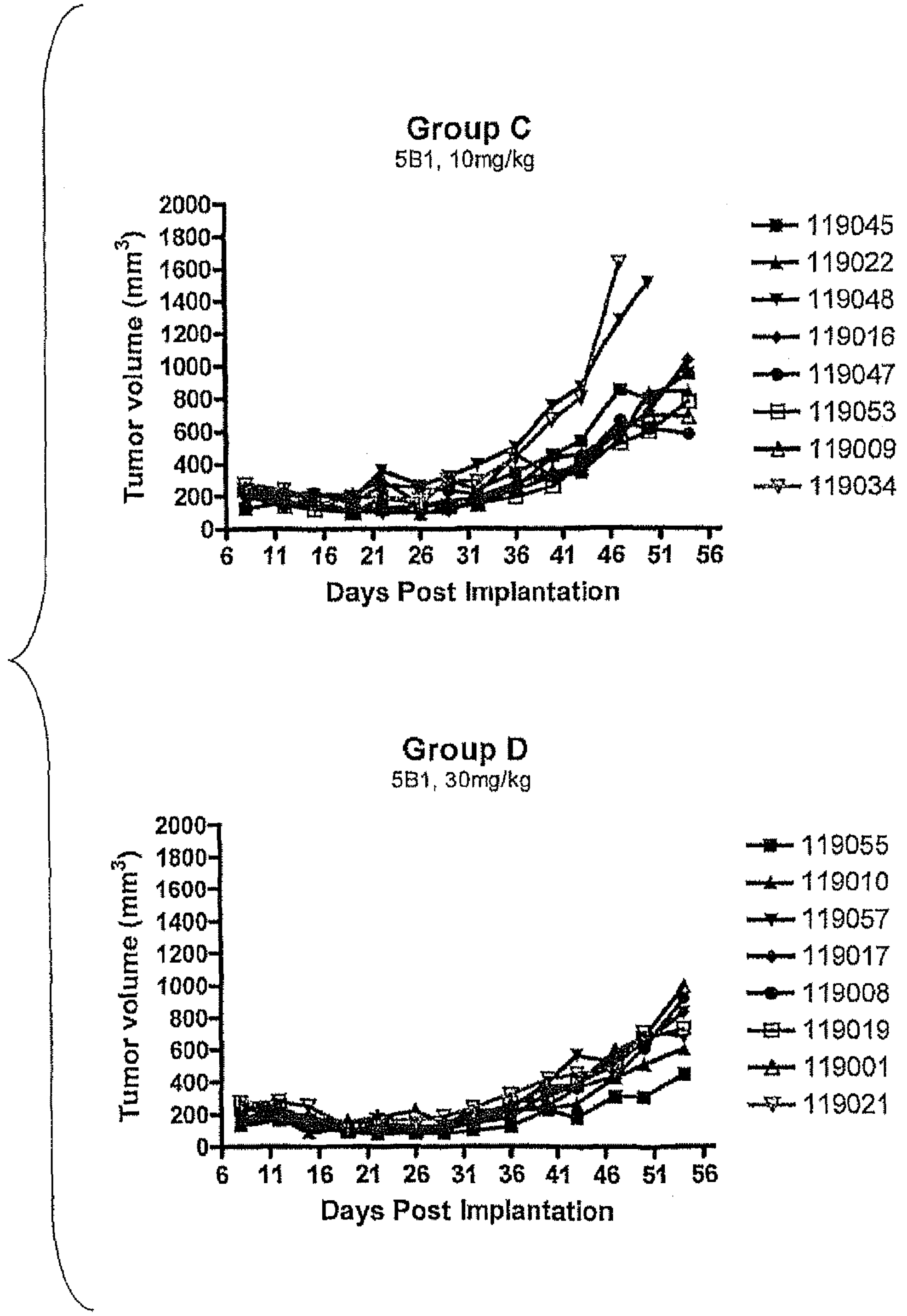
Figure 15C:
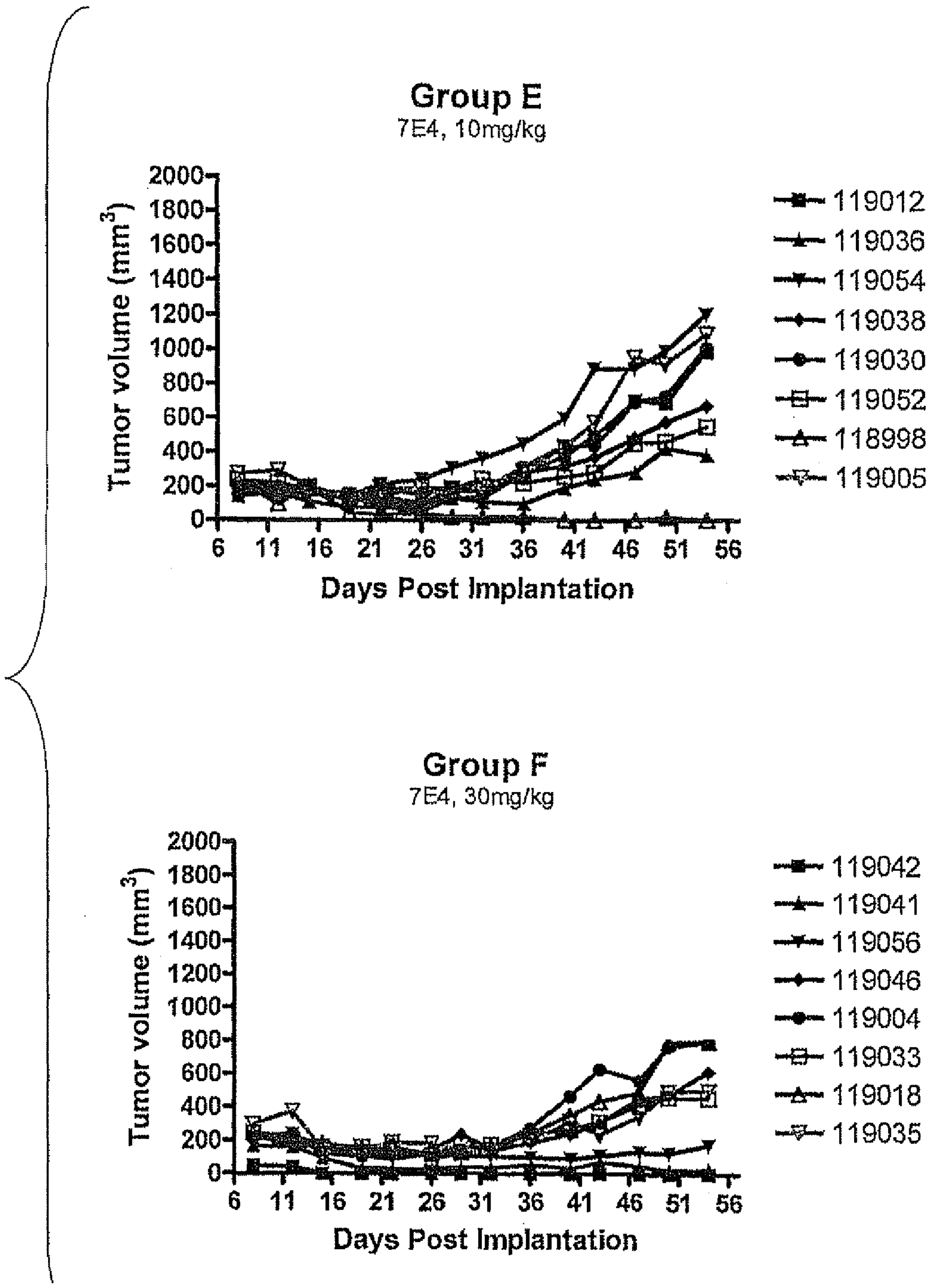

FIGS. 15A-C show the tumor volume over time in individual SCID mice that were implanted with DMS79 small cell lung cancer tumor cells (Fucosyl-GM1$^+$). After a tumor was established, the mice were treated five times with one of the following therapies: (A) PBS (vehicle control); (B) human IgG1 (isotype control) at 30 mg/kg per mouse; (C) anti-Fucosyl-GM1 monoclonal antibody 5B1 at 10 mg/kg per mouse; (D) anti-Fucosyl-GM1 monoclonal antibody 5B1 at 30 mg/kg per mouse; (E) anti-Fucosyl-GM1 monoclonal antibody 7E4 at 10 mg/kg per mouse; or (F) anti-Fucosyl-GM1 monoclonal antibody 7E4 at mg/kg per mouse. The tumor volume on the first day of treatment was about 200 $mm^3$.

FIGS. 16A and B show the mean and median tumor volume, respectively, of the mice shown in FIG. 15.

Figure 17:
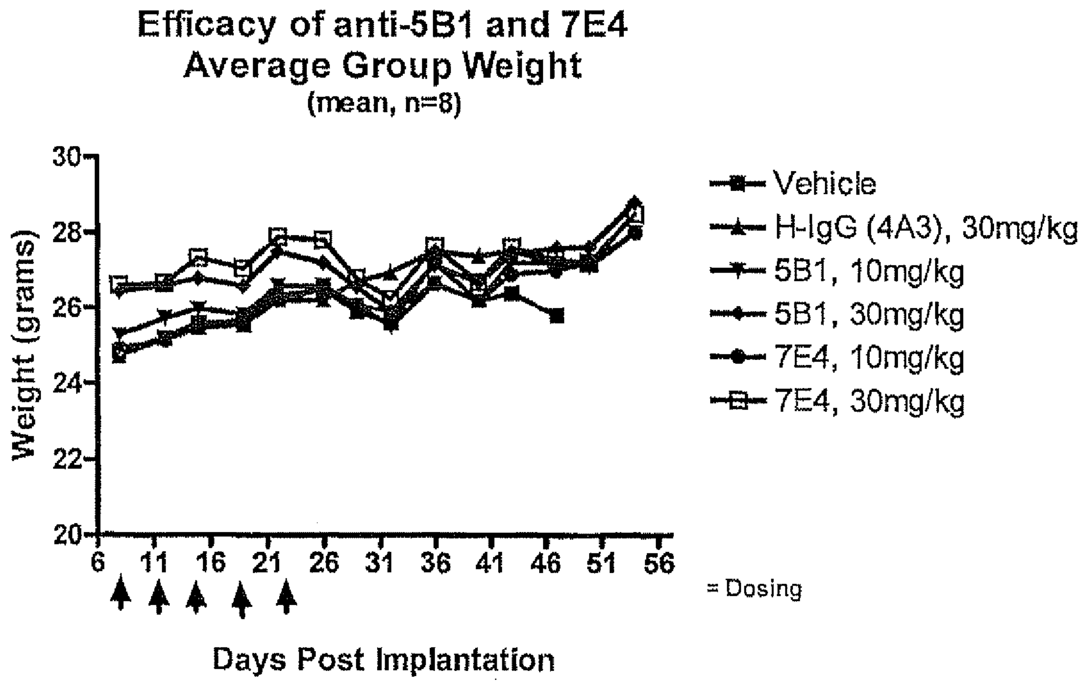

FIG. 17 shows the mean group weight of the mice shown in FIG. 15.

DETAILED DESCRIPTION

In one aspect, the present disclosure relates generally to isolated monoclonal antibodies, particularly human monoclonal antibodies that bind specifically to Fucosyl-GM1. In certain embodiments, the antibodies of this disclosure exhibit one or more desirable functional properties, such as high affinity binding to Fucosyl-GM1 and/or the ability to inhibit growth of tumor cells in vitro or in vivo. In certain embodiments, the antibodies of this disclosure are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunconjugates or bispecific molecules of this disclosure. This disclosure also relates to methods of using the antibodies, such as to treat diseases such as cancer.

In order that the present disclosure may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the Fucosyl-GM1 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., Fucosyl-GM1). It has been shown that the antigen-binding function of an antibody can be performed by fragments of a full-length antibody.

Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds Fucosyl-GM1 is substantially free of antibodies that specifically bind antigens other than Fucosyl-GM1). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of this disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to Fucosyl-GM1" is intended to refer to an antibody that binds to Fucosyl-GM1 with a $K_D$ of $1\times10^{-7}$ M or less, more preferably $5\times10^{-8}$ M or less, more preferably $1\times10^{-8}$ M or less, more preferably $5\times10^{-9}$ M or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less, even more preferably $10^{-9}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of this disclosure are described in further detail in the following subsections.

Anti-Fucosyl-GM1 Antibodies

The antibodies of this disclosure are characterized by particular functional features or properties of the antibodies. For example, the antibodies bind specifically to Fucosyl-GM1, preferably Fucosyl-GM1. Preferably, an antibody of this disclosure binds to Fucosyl-GM1 with high affinity, for example with a $K_D$ of $1\times10^{-7}$ M or less. The anti-Fucosyl-GM1 antibodies of this disclosure preferably exhibit one or more of the following characteristics:

(a) specifically binds to Fucosyl-GM1; and (b) binds to the human small cell lung cancer cell line DMS-79 (Human SCLC ATCC #CRL-2049).

Preferrably, the antibody binds to Fucosyl-GM1 with a $K_D$ of $5\times10^{-8}$ M or less, binds to Fucosyl-GM1 with a $K_D$ of $1\times10^{-8}$ M or less, binds to Fucosyl-GM1 with a $K_D$ of $5\times10^{-9}$ M or less, or binds to Fucosyl-GM1 with a $K_D$ of between $1\times10^{-}$M and $1\times10^{-10}$ M or less. Standard assays to evaluate the binding ability of the antibodies toward Fucosyl-GM1 are known in the art, including for example, ELISAs, Western blots and RIAs. The binding kinetics (e.g., binding affinity) of the antibodies also can be assessed by standard assays known in the art, such as by ELISA, Scatchard and Biacore analysis.

Monoclonal Antibodies 5B1, 5B1a, 7D4, 7E4, 13B8 and 18D5

Preferred antibodies of this disclosure are the human monoclonal antibodies 5B1, 5B1a, 7D4, 7E4, 13B8 and 18D5, isolated and structurally characterized as described in Examples 1 and 2. The $V_H$ amino acid sequences of 5B1, 5B1a, 7D4, 7E4, 13B8 and 18D5 are shown in SEQ ID NOs:1, 2, 3, 4, 5 and 6, respectively. The $V_L$ amino acid sequences of 5B1, 5B1a, 7D4, 7E4, 13B8 and 18D5 are shown in SEQ ID NOs:7, 8, 9, 10, 11 and 12, respectively.

Given that each of these antibodies can bind to Fucosyl-GM1, the $V_H$ and $V_L$ sequences can be "mixed and matched" to create other anti-Fucosyl-GM1 binding molecules of this disclosure. Fucosyl-GM1 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NOs: 1, 2, 3, 4, 5 and 6; and (b) a light chain variable region comprising an amino acid sequence selected from the group consisting of SEQ ID NOs: 7, 8, 9, 10, 11 and 12;

wherein the antibody specifically binds Fucosyl-GM1, preferably Fucosyl-GM1. Preferred heavy and light chain combinations include:

(a) a heavy chain variable region comprising the amino acid sequence of SEQ ID NO:1; and (b) a light chain variable region comprising the amino acid sequence of SEQ ID NO:7; or (a) a heavy chain variable region comprising the amino acid sequence of SEQ ID NO:2; and (b) a light chain variable region comprising the amino acid sequence of SEQ ID NO:8; or (a) a heavy chain variable region comprising the amino acid sequence of SEQ ID NO:3; and (b) a light chain variable region comprising the amino acid sequence of SEQ ID NO:9; or (a) a heavy chain variable region comprising the amino acid sequence of SEQ ID NO:4; and (b) a light chain variable region comprising the amino acid sequence of SEQ ID NO:10; or (a) a heavy chain variable region comprising the amino acid sequence of SEQ ID NO:5; and (b) a light chain variable region comprising the amino acid sequence of SEQ ID NO:11; or (a) a heavy chain variable region comprising the amino acid sequence of SEQ ID NO:6; and (b) a light chain variable region comprising the amino acid sequence of SEQ ID NO:12.

In another aspect, this disclosure provides antibodies that comprise the heavy chain and light chain CDR1s, CDR2s and CDR3s of 5B1, 5B1a, 7D4, 7E4, 13B8 and 18D5, or combinations thereof. The amino acid sequences of the $V_H$ CDR1s of 5B1, 5B1a, 7D4, 7E4, 13B8 and 18D5 are shown in SEQ ID NOs:13, 14, 15, 16, 17 and 18, respectively. The amino acid sequences of the $V_H$ CDR2s of 5B1, 5B1a, 7D4, 7E4, 13B8 and 18D5 are shown in SEQ ID NOs: 19, 20, 21, 22, 23 and 24, respectively. The amino acid sequences of the $V_H$ CDR3s of 5B1, 5B1a, 7D4, 7E4, 13B8 and 18D5 are shown in SEQ ID NOs:25, 26, 27, 28, 29 and 30, respectively. The amino acid sequences of the $V_k$ CDR1s of 5B1, 5B1a, 7D4, 7E4, 13B8 and 18D5 are shown in SEQ ID NOs:31, 32, 33, 34, 35 and 36, respectively. The amino acid sequences of the $V_k$ CDR2s of 5B1, 5B1a, 7D4, 7E4, 13B8 and 18D5 are shown in SEQ ID NOs:37, 38, 39, 40, 41 and 42, respectively. The amino acid sequences of the $V_k$ CDR3s of 5B1, 5B1a, 7D4, 7E4, 13B8 and 18D5 are shown in SEQ ID NOs:43, 44, 45, 46, 47 and 48, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to Fucosyl-GM1 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-Fucosyl-GM1 binding molecules of this disclosure. Fucosyl-GM1 binding of such "mixed and matched" antibodies can be tested using the binding assays described above and in the Examples (e.g., ELISAs, Biacore analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 5B1, 5B1a, 7D4, 7E4, 13B8 and 18D5.

Accordingly, in another aspect, this disclosure provides an isolated monoclonal antibody, or antigen binding portion thereof comprising:

(a) a heavy chain variable region CDR1 comprising an amino acid sequence selected from the group consisting of SEQ ID NOs:13, 14, 15, 16, 17 and 18;

(b) a heavy chain variable region CDR2 comprising an amino acid sequence selected from the group consisting of SEQ ID NOs:19, 20, 21, 22, 23 and 24;

(c) a heavy chain variable region CDR3 comprising an amino acid sequence selected from the group consisting of SEQ ID NOs:25, 26, 27, 28, 29 and 30;

(d) a light chain variable region CDR1 comprising an amino acid sequence selected from the group consisting of SEQ ID NOs:31, 32, 33, 34, 35 and 36;

(e) a light chain variable region CDR2 comprising an amino acid sequence selected from the group consisting of SEQ ID NOs:37, 38, 39, 40, 41 and 42; and (f) a light chain variable region CDR3 comprising an amino acid sequence selected from the group consisting of SEQ ID NOs:43, 44, 45, 46, 47 and 48;

wherein the antibody specifically binds Fucosyl-GM1, preferably Fucosyl-GM1.

In a preferred embodiment, the antibody comprises:

(a) a heavy chain variable region CDR1 comprising SEQ ID NO:13;

(b) a heavy chain variable region CDR2 comprising SEQ ID NO:19;

(c) a heavy chain variable region CDR3 comprising SEQ ID NO:25;

(d) a light chain variable region CDR1 comprising SEQ ID NO:31;

(e) a light chain variable region CDR2 comprising SEQ ID NO:37; and (f) a light chain variable region CDR3 comprising SEQ ID NO:43.

In another preferred embodiment, the antibody comprises:

(a) a heavy chain variable region CDR1 comprising SEQ ID NO:14;

(b) a heavy chain variable region CDR2 comprising SEQ ID NO:20;

(c) a heavy chain variable region CDR3 comprising SEQ ID NO:26;

(d) a light chain variable region CDR1 comprising SEQ ID NO:32;

(e) a light chain variable region CDR2 comprising SEQ ID NO:38; and (f) a light chain variable region CDR3 comprising SEQ ID NO:44.

In another preferred embodiment, the antibody comprises:

(a) a heavy chain variable region CDR1 comprising SEQ ID NO:15;

(b) a heavy chain variable region CDR2 comprising SEQ ID NO:21;

(c) a heavy chain variable region CDR3 comprising SEQ ID NO:27;

(d) a light chain variable region CDR1 comprising SEQ ID NO:33;

(e) a light chain variable region CDR2 comprising SEQ ID NO:39; and (f) a light chain variable region CDR3 comprising SEQ ID NO:45.

In another preferred embodiment, the antibody comprises:

(a) a heavy chain variable region CDR1 comprising SEQ ID NO:16;

(b) a heavy chain variable region CDR2 comprising SEQ ID NO:22;

(c) a heavy chain variable region CDR3 comprising SEQ ID NO:28;

(d) a light chain variable region CDR1 comprising SEQ ID NO:34;

(e) a light chain variable region CDR2 comprising SEQ ID NO:40; and (f) a light chain variable region CDR3 comprising SEQ ID NO:46.

In another preferred embodiment, the antibody comprises:

(a) a heavy chain variable region CDR1 comprising SEQ ID NO:17;

(b) a heavy chain variable region CDR2 comprising SEQ ID NO:23;

(c) a heavy chain variable region CDR3 comprising SEQ ID NO:29;

(d) a light chain variable region CDR1 comprising SEQ ID NO:35;

(e) a light chain variable region CDR2 comprising SEQ ID NO:41; and (f) a light chain variable region CDR3 comprising SEQ ID NO:47.

In another preferred embodiment, the antibody comprises:

(a) a heavy chain variable region CDR1 comprising SEQ ID NO:18;

(b) a heavy chain variable region CDR2 comprising SEQ ID NO:24;

(c) a heavy chain variable region CDR3 comprising SEQ ID NO:30;

(d) a light chain variable region CDR1 comprising SEQ ID NO:36;

(e) a light chain variable region CDR2 comprising SEQ ID NO:42; and (f) a light chain variable region CDR3 comprising SEQ ID NO:48.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to Fucosyl-GM1. Within some embodiments, such antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to Fucosyl-GM1 and wherein the CDR3 domain from the first human antibody replaces a CDR3 domain in a human antibody that is lacking binding specificity for Fucosyl-GM1 to generate a second human antibody that is capable of specifically binding to Fucosyl-GM1. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody, or an antigen-binding portion thereof, comprising a heavy chain variable region that is the product of or derived from a human $V_H$ 3-48 gene, wherein the antibody specifically binds Fucosyl-GM1, preferably Fucosyl-GM1. In another preferred embodiment, this disclosure provides an isolated monoclonal antibody, or an antigen-binding portion thereof, comprising a light chain variable region that is the product of or derived from a human $V_K$ L15 gene, wherein the antibody specifically binds Fucosyl-GM1, preferably Fucosyl-GM1. In yet another preferred embodiment, this disclosure provides an isolated monoclonal antibody, or antigen-binding portion thereof, wherein the antibody:

(a) comprises a heavy chain variable region that is the product of or derived from a human $V_H$ 3-48 gene (which gene encodes the amino acid sequence set forth in SEQ ID NO: 61);

(b) comprises a light chain variable region that is the product of or derived from a human $V_K$ L15 gene (which gene encodes the amino acid sequence set forth in SEQ ID NO:62); and (c) specifically binds to Fucosyl-GM1.

Examples of antibodies having $V_H$ and $V_K$ of $V_H$ 3-48 and $V_K$ L15, respectively, are 5B1, 5B1a, 7D4, 7E4, 13B8 and 18D5.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein, and wherein the antibodies retain the desired functional properties of the anti-Fucosyl-GM1 antibodies of this disclosure.

For example, this disclosure provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs:1, 2, 3, 4, 5 and 6;

(b) the light chain variable region comprises an amino acid sequence that is at least 80% homologous to an amino acid sequence selected from the group consisting of SEQ ID NOs:7, 8, 9, 10, 11 and 12; and the antibody exhibits one or more of the following properties:

(c) the antibody binds to Fucosyl-GM1 with a $K_D$ of $1\times10^{-7}$ M or less;

(d) the antibody binds to the human small cell lung cancer cell line DMS-79 (Human SCLC ATCC #CRL-2049).

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs:49, 50, 51, 52, 53, 54, 55, 56, 57, 58, 59 and 60, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.,* 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. (See www.ncbi.nlm.nih.gov).

Antibodies with Conservative Modifications

In certain embodiments, an antibody of this disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 5B1, 5B1a, 7D4, 7E4, 13B8 or 18D5), or conservative modifications thereof, and wherein the antibodies retain the desired functional properties of the anti-Fucosyl-GM1 antibodies of this disclosure. Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs:25, 26, 27, 28, 29 and 30, and conservative modifications thereof;

(b) the light chain variable region CDR3 sequence comprises an amino acid sequence selected from the group consisting of amino acid sequence of SEQ ID NOs:43, 44, 45, 46, 47 and 48, and conservative modifications thereof; and the antibody exhibits one or more of the following properties:

(c) specifically binds to Fucosyl-GM1; and (d) the antibody binds to the human small cell lung cancer cell line DMS-79 (Human SCLC ATCC #CRL-2049).

In a preferred embodiment, the heavy chain variable region CDR2 sequence comprises an amino acid sequence selected from the group consisting of amino acid sequences of SEQ ID NOs:19, 20, 21, 22, 23 and 24, and conservative modifications thereof; and the light chain variable region CDR2 sequence comprises an amino acid sequence selected from the group consisting of amino acid sequences of SEQ ID NOs:37, 38, 39, 40, 41 and 42, and conservative modifications thereof. In another preferred embodiment, the heavy chain variable region CDR1 sequence comprises an amino acid sequence selected from the group consisting of amino acid sequences of SEQ ID NOs:13, 14, 15, 16, 17 and 18, and conservative modifications thereof; and the light chain variable region CDR1 sequence comprises an amino acid sequence selected from the group consisting of amino acid sequences of SEQ ID NOs:31, 32, 33, 34, 35 and 36, and conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function (i.e., the functions set forth in (c) and (d) above) using the functional assays described herein.

Antibodies that Bind to the Same Epitope as Anti-Fucosyl-GM1 Antibodies of this Disclosure In another embodiment, this disclosure provides antibodies that bind to the same epitope on Fucosyl-GM1 as any of the Fucosyl-GM1 monoclonal antibodies of this disclosure (i.e., antibodies that have the ability to cross-compete for binding to Fucosyl-GM1 with any of the monoclonal antibodies of this disclosure). In preferred embodiments, the reference antibody for cross-competition studies can be the monoclonal antibody 5B1 (having $V_H$ and $V_L$ sequences as shown in SEQ ID NOs:1 and 7, respectively), or the monoclonal antibody 5B1a (having $V_H$ and $V_L$ sequences as shown in SEQ ID NOs:2 and 8, respectively), or the monoclonal antibody 7D4 (having $V_H$ and $V_L$ sequences as shown in SEQ ID NOs:3 and 9, respectively), or the monoclonal antibody 7E4 (having $V_H$ and $V_L$ sequences as shown in SEQ ID NOs:4 and 10, respectively), or the monoclonal antibody 13B8 (having $V_H$ and $V_L$ sequences as shown in SEQ ID NOs:5 and 11, respectively), or the monoclonal antibody 18D5 (having $V_H$ and $V_L$ sequences as shown in SEQ ID NOs:6 and 12, respectively). Such cross-competing antibodies can be identified based on their ability to cross-compete with 5B1, 5B1a, 7D4, 7E4, 13B8 or 18D5 in standard Fucosyl-GM1 binding assays. For example, BIAcore analysis, ELISA assays or flow cytometry may be used to demonstrate cross-competition with the antibodies of the current disclosure. The ability of a test antibody to inhibit the binding of, for example, 5B1, 5B1a, 7D4, 7E4, 13B8 or 18D5, to Fucosyl-GM1 demonstrates that the test antibody can compete with 5B1, 5B1a, 7D4, 7E4, 13B8 or 18D5 for binding to Fucosyl-GM1 and thus binds to the same epitope on Fucosyl-GM1 as 5B1, 5B1a, 7D4, 7E4, 13B8 or 18D5. In a preferred embodiment, the antibody that binds to the same epitope on Fucosyl-GM1 as 5B1, 5B1a, 7D4, 7E4, 13B8 or 18D5 is a human monoclonal antibody. Such human monoclonal antibodies can be prepared and isolated as described in the Examples.

Engineered and Modified Antibodies

An antibody of this disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of this disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs:13, 14, 15, 16, 17 and 18, SEQ ID NOs: 19, 20, 21, 22, 23 and 24 and SEQ ID NOs:25, 26, 27, 28, 29 and 30, respectively, and a light chain variable region comprising CDR1, CDR2, and CDR3 sequences comprising an amino acid sequence selected from the group consisting of SEQ ID NOs:31, 32, 33, 34, 35 and 36, SEQ ID NOs:37, 38, 39, 40, 41 and 42 and SEQ ID NOs:43, 44, 45, 46, 47 and 48, respectively. Thus, such antibodies contain the $V_H$ and $V_L$ CDR sequences of monoclonal antibodies 5B1, 5B1a, 7D4, 7E4, 13B8 or 18D5 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCol2 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (?) and 3-23 (AJ406678).

Preferred framework sequences for use in the antibodies of this disclosure are those that are structurally similar to the framework sequences used by selected antibodies of this disclosure, e.g., similar to the $V_H$ 3-48 framework sequences (SEQ ID NO:61) and/or the $V_K$ L15 framework sequences (SEQ ID NO:62) used by preferred monoclonal antibodies of this disclosure. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, this disclosure provides isolated anti-Fucosyl-GM1 monoclonal antibodies, or antigen binding portions thereof, comprising a heavy chain variable region comprising: (a) a $V_H$ CDR1 region comprising an amino acid sequence selected from the group consisting of SEQ ID NOs:13, 14, 15, 16, 17 and 18, or an amino acid sequence having one, two, three, four or five amino acid substitutions, deletions or additions as compared to SEQ ID NOs:13, 14, 15, 16, 17 and 18; (b) a $V_H$ CDR2 region comprising an amino acid sequence selected from the group consisting of SEQ ID NOs: 19, 20, 21, 22, 23 and 24, or an amino acid sequence having one, two, three, four or five amino acid substitutions, deletions or additions as compared to SEQ ID NOs:19, 20, 21, 22, 23 and 24; (c) a $V_H$ CDR3 region comprising an amino acid sequence selected from the group consisting of SEQ ID NOs:25, 26, 27, 28, 29 and 30, or an amino acid sequence having one, two, three, four or five amino acid substitutions, deletions or additions as compared to SEQ ID NOs:25, 26, 27, 28, 29 and 30; (d) a $V_K$ CDR1 region comprising an amino acid sequence selected from the group consisting of SEQ ID NOs:31, 32, 33, 34, 35 and 36, or an amino acid sequence having one, two, three, four or five amino acid substitutions, deletions or additions as compared to SEQ ID NOs:31, 32, 33, 34, 35 and 36; (e) a $V_K$ CDR2 region comprising an amino acid sequence selected from the group consisting of SEQ ID NOs:37, 38, 39, 40, 41 and 42, or an amino acid sequence having one, two, three, four or five amino acid substitutions, deletions or additions as compared to SEQ ID NOs:37, 38, 39, 40, 41 and 42; and (f) a $V_K$ CDR3 region comprising an amino acid sequence selected from the group consisting of SEQ ID NOs:43, 44, 45, 46, 47 and 48, or an amino acid sequence having one, two, three, four or five amino acid substitutions, deletions or additions as compared to SEQ ID NOs:43, 44, 45, 46, 47 and 48.

Engineered antibodies of this disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for 7E4, amino acid residue #11 (within FR1) of $V_H$ is a serine whereas this residue in the corresponding $V_H$ 3-48 germline sequence is a leucine. To return the framework region sequences to their germline configuration, the somatic mutations can be "backmutated" to the germline sequence by, for example, site-directed mutagenesis or PCR-mediated mutagenesis (e.g., residue #11 of FR1 of the $V_H$ of 7E4 can be "backmutated" from serine to leucine).

As another example, for 5B1, 5B1a, 7D4, 7E4, 13B8 and 18D5, amino acid residue #16 (within FR1) of $V_H$ is a glutamic acid whereas this residue in the corresponding $V_H$ 3-48 germline sequence is a glycine. To return the framework region sequences to their germline configuration, for example, residue #16 of the $V_H$ of 5B1, 5B1a, 7D4, 7E4, 13B8 and 18D5 can be "backmutated" from glutamic acid to glycine. Such "backmutated" antibodies are also intended to be encompassed by this disclosure.

As another example, for 5B1, 5B1a, 7D4, 7E4, 13B8 and 18D5, amino acid residue #23 (within FR1) of $V_H$ is a valine whereas this residue in the corresponding $V_H$ 3-48 germline sequence is an alanine. To return the framework region sequences to their germline configuration, for example, residue #23 of the $V_H$ of 5B1, 5B1a, 7D4, 7E4, 13B8 and 18D5 can be "backmutated" from valine to alanine. Such "backmutated" antibodies are also intended to be encompassed by this disclosure.

As another example, for 7D4, amino acid residue #24 (within FR1) of $V_H$ is a valine whereas this residue in the corresponding $V_H$ 3-48 germline sequence is an alanine. To return the framework region sequences to their germline configuration, for example, residue #24 of the $V_H$ of 7D4 can be "backmutated" from valine to alanine. Such "backmutated" antibodies are also intended to be encompassed by this disclosure.

As another example, for 13B8, amino acid residue #29 (within FR1) of $V_H$ is a leucine whereas this residue in the corresponding $V_H$ 3-48 germline sequence is an phenylalanine. To return the framework region sequences to their germline configuration, for example, residue #29 of the $V_H$ of 13B8 can be "backmutated" from leucine to phenylalanine. Such "backmutated" antibodies are also intended to be encompassed by this disclosure.

As another example, for 7D4, 13B8 and 18D5, amino acid residue #48 (within FR2) of $V_H$ is an isoleucine whereas this residue in the corresponding $V_H$ 3-48 germline sequence is a valine. To return the framework region sequences to their germline configuration, for example, residue #48 (residue #13 within FR2) of the $V_H$ of 7D4, 13B8 and 18D5 can be "backmutated" from isoleucine to valine. Such "backmutated" antibodies are also intended to be encompassed by this disclosure.

As another example, for 7D4 and 18D5, amino acid residue #84 (within FR3) of $V_H$ is a serine whereas this residue in the corresponding $V_H$ 3-48 germline sequence is an asparagine. To return the framework region sequences to their germline configuration, for example, residue #84 (residue #18 within FR3) of the $V_H$ of 7D4 and 18D5 can be "backmutated" from serine to asparagine. Such "backmutated" antibodies are also intended to be encompassed by this disclosure.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 $FUT8^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of this disclosure. See for example, EP 0 154 316 by Nishimura et al. and EP 0 401 384 by Ishikawa et al.

Methods of Engineering Antibodies

As discussed above, the anti-Fucosyl-GM1 antibodies having $V_H$ and $V_K$ sequences disclosed herein can be used to create new anti-Fucosyl-GM1 antibodies by modifying the VH and/or $V_K$ sequences, or the constant region(s) attached thereto. Thus, in another aspect of this disclosure, the structural features of an anti-Fucosyl-GM1 antibody of this disclosure, e.g. 5B1, 5B1a, 7D4, 7E4, 13B8 or 18D5, are used to create structurally related anti-Fucosyl-GM1 antibodies that retain at least one functional property of the antibodies of this disclosure, such as binding to Fucosyl-GM1. For example, one or more CDR regions of 5B1, 5B1a, 7D4, 7E4, 13B8 or 18D5, or mutations thereof, can be combined recombinantly with known framework regions and/or other CDRs to create additional, recombinantly-engineered, anti-Fucosyl-GM1 antibodies of this disclosure, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-Fucosyl-GM1 antibody comprising:

(a) providing: (i) a heavy chain variable region antibody sequence comprising a CDR1 sequence selected from the group consisting of SEQ ID NOs:13, 14, 15, 16, 17 and 18, a CDR2 sequence selected from the group consisting of SEQ ID NOs: 19, 20, 21, 22, 23 and 24, and/or a CDR3 sequence selected from the group consisting of SEQ ID NOs:25, 26, 27, 28, 29 and 30; and/or (ii) a light chain variable region antibody sequence comprising a CDR1 sequence selected from the group consisting of SEQ ID NOs:31, 32, 33, 34, 35 and 36, a CDR2 sequence selected from the group consisting of SEQ ID NOs:37, 38, 39, 40, 41 and 42, and/or a CDR3 sequence selected from the group consisting of SEQ ID NOs:43, 44, 45, 46, 47 and 48;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-Fucosyl-GM1 antibodies described herein, which functional properties include, but are not limited to:

(a) the antibody binds to Fucosyl-GM1 with a $K_D$ of $1\times10^{-7}$ M or less;

(b) binds to the human small cell lung cancer cell line DMS-79 (Human SCLC ATCC #CRL-2049).

The functional properties of the altered antibodies can be assessed using standard assays available in the art and/or described herein, such as those set forth in the Examples (e.g., flow cytometry, binding assays).

In certain embodiments of the methods of engineering antibodies of this disclosure, mutations can be introduced randomly or selectively along all or part of an anti-Fucosyl-GM1 antibody coding sequence and the resulting modified anti-Fucosyl-GM1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of this Disclosure

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of this disclosure are those encoding the VH and VL sequences of the 5B1, 5B1a, 7D4, 7E4, 13B8 or 3C4 monoclonal antibodies. DNA sequences encoding the VH sequences of 5B1, 5B1a, 7D4, 7E4, 13B8 and 3C4 are shown in SEQ ID NOs: 49, 50, 51, 52, 53 and 54, respectively. DNA sequences encoding the VL sequences of 5B1, 5B1a, 7D4, 7E4, 13B8 and 3C4 are shown in SEQ ID NOs: 55, 56, 57, 58, 59 and 60, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of this Disclosure

Monoclonal antibodies (mAbs) of the present disclosure can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of this disclosure are human monoclonal antibodies. Such human monoclonal antibodies directed against Fucosyl-GM1 can be generated using transgenic or transchromosomic mice carrying parts of the human immune system rather than the mouse system. These transgenic and transchromosomic mice include mice referred to herein as HuMAb mice and KM mice™, respectively, and are collectively referred to herein as "human Ig mice."

The HuMAb mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) International Immunology 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. Such mice, referred to herein as "KM mice™", are described in detail in PCT Publication WO 02/43478 to Ishida et al.

Still further, alternative transgenic animal systems expressing human immunoglobulin genes are available in the art and can be used to raise anti-Fucosyl-GM1 antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-Fucosyl-GM1 antibodies of this disclosure. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-Fucosyl-GM1 antibodies of this disclosure.

Human monoclonal antibodies of this disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of this disclosure, such mice can be immunized with a purified or enriched preparation of Fucosyl-GM1 antigen and/or recombinant Fucosyl-GM1, or an Fucosyl-GM1 fusion protein, as described by Lonberg, N. et al. (1994) *Nature* 368 (6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of Fucosyl-GM1 antigen can be used to immunize the human Ig mice intraperitoneally.

Detailed procedures to generate fully human monoclonal antibodies to Fucosyl-GM1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-Fucosyl-GM1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM mouse™ strain can be used, as described in Example 1.

Generation of Hybridomas Producing Human Monoclonal Antibodies of this Disclosure To generate hybridomas producing human monoclonal antibodies of this disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspensions of splenic lymphocytes from immunized mice can be fused using an electric field based electrofusion method, using a Cyto Pulse large chamber cell fusion electroporator (Cyto Pulse Sciences, Inc., Glen Burnie, Md.). Cells are plated at approximately $2\times10^5$ in flat bottom microtiter plate, followed by a one week incubation in DMEM high glucose medium with L-glutamine and sodium pyruvate (Mediatech, Inc., Herndon, Va.) and further containing 20% fetal Bovine Serum (Hyclone, Logan, Utah), 18% P388DI conditional media, 5% Origen Hybridoma cloning factor (BioVeris, Gaithersburg, Va.), 4 mM L-glutamine, 5 mM HEPES, 0.055 mM β-mercaptoethanol, 50 units/ml penicillin, 50 mg/ml streptomycin and 1× Hypoxanthine-aminopterin-thymidine (HAT) media (Sigma; the HAT is added 24 hours after the fusion). After one week, cells cultured in medium in which HAT was used was replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies of this Disclosure

Antibodies of this disclosure also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRo promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of this disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of this disclosure can be tested for binding to Fucosyl-GM1 by, for example, standard ELISA. Briefly, microtiter plates are coated with purified Fucosyl-GM1 at 0.25 μg/ml in PBS, and then blocked with 5% bovine serum albumin in PBS. Dilutions of antibody (e.g., dilutions of plasma from Fucosyl-GM1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with Fucosyl-GM1 immunogen. Hybridomas that bind with high avidity to Fucosyl-GM1 are subcloned and further characterized. One clone from each hybridoma, which retains the reactivity of the parent cells (by ELISA), can be chosen for making a 5-10 vial cell bank stored at −140° C., and for antibody purification.

To purify anti-Fucosyl-GM1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-Fucosyl-GM1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using Fucosyl-GM1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-Fucosyl-GM1 human IgGs can be further tested for reactivity with Fucosyl-GM1 antigen by Western blotting. Briefly, Fucosyl-GM1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present disclosure features an anti-Fucosyl-GM1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of this disclosure include duocarmycins, calicheamicins, maytansines and auristatins, and derivatives thereof. An example of a calicheamicin antibody conjugate is commercially available (Mylotarg™; Wyeth-Ayerst). Examples of therapeutic cytotoxins may be found, for example, in U.S. Pat. Nos. 6,548,530 and 6,281,354 and US Patent application Nos: US 2003/0064984, US 2003/0073852 and US 2003/005033 1.

Cytotoxins can be conjugated to antibodies of this disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $iodine^{131}$, $indium^{111}$, $yttrium^{90}$ and $lutetium^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of this disclosure.

The antibody conjugates of this disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific molecules comprising an anti-Fucosyl-GM1 antibody, or a fragment thereof, of this disclosure. An antibody of this disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of this disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of this disclosure, an antibody of this disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for Fucosyl-GM1 and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)), and to target cells expressing Fucosyl-GM1. These bispecific molecules target Fucosyl-GM1 expressing cells to effector cell and trigger Fc receptor-mediated effector cell activities, such as phagocytosis of an Fucosyl-GM1 expressing cells, antibody dependent cell-mediated cytotoxicity (ADCC), cytokine release, or generation of superoxide anion.

In an embodiment of this disclosure in which the bispecific molecule is multispecific, the molecule can further include a third binding specificity, in addition to an anti-Fc binding specificity and an anti-Fucosyl-GM1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of this disclosure comprise as a binding specificity at least one antibody, or an antibody fragment thereof, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγR11(CD32), and FcγR111 (CD 16). In one preferred embodiment, the Fcγ receptor a human high affinity FcγRI. The human FcγRI is a 72 kDa molecule, which shows high affinity for monomeric IgG ($10^8$-$10^9$ $M^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J Immunol* 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (Fcα RI (CD89)), the binding of which is preferably not blocked by human immunoglobulin A (IgA). The term "IgA receptor" is intended to include the gene product of one α-gene (Fcα RI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity (≈$5\times10^7$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of this disclosure are murine, chimeric and humanized monoclonal antibodies.

The bispecific molecules of the present disclosure can be prepared by conjugating the constituent binding specificities, e.g., the anti-FcR and anti-Fucosyl-GM1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×$F(ab')_2$ or ligand x Fab fusion protein. A bispecific molecule of this disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a $\gamma$ counter or a scintillation counter or by autoradiography.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of this disclosure. For example, a pharmaceutical composition of this disclosure can comprise a combination of antibodies (or immunoconjugates or bispecifics) that bind to different epitopes on the target antigen or that have complementary activities.

Pharmaceutical compositions of this disclosure also can be administered in combination therapy, i.e., combined with other agents. For example, the combination therapy can include an anti-Fucosyl-GM1 antibody of the present disclosure combined with at least one other anti-inflammatory or immunosuppressant agent. Examples of therapeutic agents that can be used in combination therapy are described in greater detail below in the section on uses of the antibodies of this disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-Fucosyl-GM1 antibody of this disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Fucosyl-GM1 antibody of this disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of this Disclosure

The antibodies, antibody compositions and methods of the present disclosure have numerous in vitro and in vivo diagnostic and therapeutic utilities involving the diagnosis and treatment of Fucosyl-GM1 mediated disorders. In a preferred embodiment, the antibodies of the present disclosure are human antibodies. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles. Preferred subjects include human patients having disorders mediated by Fucosyl-GM1 activity or having disorders coincident with a Fucosyl-GM1 mediated activity. The methods are particularly suitable for treating human patients having a disorder associated with aberrant Fucosyl-GM1 expression or increased Fucosyl-GM1 presence. When antibodies to Fucosyl-GM1 are administered together with another agent, the two can be administered in either order or simultaneously.

Given the specific binding of the antibodies of this disclosure for Fucosyl-GM1, the antibodies of this disclosure can be used to specifically detect Fucosyl-GM1 expression on the surface of cells and, moreover, can be used to purify Fucosyl-GM1 via immunoaffinity purification.

This disclosure further provides methods for detecting the presence of Fucosyl-GM1 antigen in a sample, or measuring the amount of Fucosyl-GM1 antigen, comprising contacting the sample, and a control sample, with a human monoclonal antibody, or an antigen binding portion thereof, which specifically binds to Fucosyl-GM1, under conditions that allow for formation of a complex between the antibody or portion thereof and Fucosyl-GM1. The formation of a complex is then detected, wherein a difference complex formation between the sample compared to the control sample is indicative the presence of Fucosyl-GM1 antigen in the sample.

Fucosyl-GM1 is expressed in small cell lung cancer, but not detected in normal lung or other tissues (Nilsson et al. (1984) *Glycoconjugate J* 1:43-9; Krug et al. (2004) *Clin Cancer Res* 10:6094-100). An anti-Fucosyl-GM1 antibody may be used alone to inhibit the growth of cancerous tumors. Alternatively, an anti-Fucosyl-GM1 antibody may be used in conjunction with other immunogenic agents, standard cancer treatments or other antibodies, as described below.

Anti-fucosyl GM1 monoclonal antibodies have been demonstrated to mediate potent CDC directed against fucosyl GM1 positive cell lines (Livingston P O et al. (1994) *J Clin Oncol.* 12:1036-44; Brezicka et al. (2000) *Cancer Immunol Immunother* 49:235-42). Further, it has been reported that the complement activation, induced by monoclonal antibodies specific to fucosyl-GM1, in combination with cytostatic drugs result in synergistic cytotoxic effects on fucosyl-GM1 expressing cells lines (Brezicka and Einbeigi (2001) *Tumour Biol* 22:97-103). Finally, anti-fucosyl-GM1 monoclonal antibodies have also been reported to inhibit the engraftment of fucosyl-GM1 expressing tumor cells in nude mice (Brezicka et al. (1991) *Int J Cancer* 49:911-8). These data support the development of a fully human monoclonal antibody to fucosyl-GM1 as an immunotherapeutic for the treatment of SCLC either alone or in combination with chemotherapeutic agents.

Preferred cancers whose growth may be inhibited using the antibodies of this disclosure include cancers typically responsive to immunotherapy. Non-limiting examples of preferred cancers for treatment include lung cancer (including small cell lung cancer and non-small cell lung cancer). Examples of other cancers that may be treated using the methods of this disclosure include colon cancer (including small intestine cancer), lung cancer, breast cancer, pancreatic cancer, melanoma (e.g., metastatic malignant melanoma), acute myeloid leukemia, kidney cancer, bladder cancer, ovarian cancer and prostate cancer, renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Furthermore, given the expression of Fucosyl-GM1 on various tumor cells, the human antibodies, antibody compositions and methods of the present disclosure can be used to treat a subject with a tumorigenic disorder, e.g., a disorder characterized by the presence of tumor cells expressing Fucosyl-GM1 including, for example, lung cancer (including small cell lung cancer and non-small cell lung cancer), colon cancer (including small intestine cancer), melanoma (e.g., metastatic malignant melanoma), acute myeloid leukemia, lung cancer, breast cancer, bladder cancer, pancreatic cancer, ovarian cancer and prostate cancer. Examples of other subjects with a tumorigenic disorder include subjects having renal cancer (e.g., renal cell carcinoma), glioblastoma, brain tumors, chronic or acute leukemias including acute lymphocytic leukemia (ALL), adult T-cell leukemia (T-ALL), chronic myeloid leukemia, acute lymphoblastic leukemia, chronic lymphocytic leukemia, lymphomas (e.g., Hodgkin's and non-Hodgkin's lymphoma, lymphocytic lymphoma, primary CNS lymphoma, T-cell lymphoma, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), entroblastic/centrocytic (cb/cc) follicular lymphomas cancers, diffuse large cell lymphomas of B lineage, angioimmunoblastic lymphadenopathy (AILD)-like T cell lymphoma and HIV associated body cavity based lymphomas), embryonal carcinomas, undifferentiated carcinomas of the rhino-pharynx (e.g., Schmincke's tumor), Castleman's disease, Kaposi's Sarcoma, multiple myeloma, Waldenstrom's macroglobulinemia and other B-cell lymphomas, nasopharangeal carcinomas, bone cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), tumor angiogenesis, spinal axis tumor, brain stem glioma, pituitary adenoma, epidermoid cancer, squamous cell cancer, environmentally induced cancers including those induced by asbestos, e.g., mesothelioma and combinations of said cancers.

Accordingly, in one embodiment, this disclosure provides a method of inhibiting growth of tumor cells in a subject, comprising administering to the subject a therapeutically effective amount of an anti-Fucosyl-GM1 antibody or antigen-binding portion thereof. Preferably, the antibody is a human anti-Fucosyl-GM1 antibody (such as any of the human anti-Fucosyl-GM1 antibodies described herein). Additionally or alternatively, the antibody may be a chimeric or humanized anti-Fucosyl-GM1 antibody.

In one embodiment, the antibodies (e.g., human monoclonal antibodies, multispecific and bispecific molecules and compositions) of this disclosure can be used to detect levels of Fucosyl-GM1 or levels of cells which contain Fucosyl-GM1 on their membrane surface, which levels can then be linked to certain disease symptoms. Alternatively, the antibodies can be used to inhibit or block Fucosyl-GM1 function which, in turn, can be linked to the prevention or amelioration of certain disease symptoms, thereby implicating Fucosyl-GM1 as a mediator of the disease. This can be achieved by contacting an experimental sample and a control sample with the anti-Fucosyl-GM1 antibody under conditions that allow for the formation of a complex between the antibody and Fucosyl-GM1. Any complexes formed between the antibody and Fucosyl-GM1 are detected and compared in the experimental sample and the control.

In another embodiment, the antibodies (e.g., human antibodies, multispecific and bispecific molecules and compositions) of this disclosure can be initially tested for binding activity associated with therapeutic or diagnostic use in vitro. For example, compositions of this disclosure can be tested using the flow cytometric assays described in the Examples below.

The antibodies (e.g., human antibodies, multispecific and bispecific molecules, immunoconjugates and compositions)

of this disclosure have additional utility in therapy and diagnosis of Fucosyl-GM1-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing Fucosyl-GM1; to mediate phagocytosis or ADCC of a cell expressing Fucosyl-GM1 in the presence of human effector cells; or to block Fucosyl-GM1 ligand binding to Fucosyl-GM1.

In a particular embodiment, the antibodies (e.g., human antibodies, multispecific and bispecific molecules and compositions) are used in vivo to treat, prevent or diagnose a variety of Fucosyl-GM1-related diseases. Examples of Fucosyl-GM1-related diseases include, among others, lung cancer (including small cell lung cancer and non-small cell lung cancer).

Suitable routes of administering the antibody compositions (e.g., human monoclonal antibodies, multispecific and bispecific molecules and immunoconjugates) of this disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-Fucosyl-GM1 antibodies of this disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the human anti-Fucosyl-GM1 antibodies or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

In one embodiment, immunoconjugates of this disclosure can be used to target compounds (e.g., therapeutic agents, labels, cytotoxins, radiotoxoins immunosuppressants, etc.) to cells which have Fucosyl-GM1 cell surface receptors by linking such compounds to the antibody. For example, an anti-Fucosyl-GM1 antibody can be conjugated to any of the toxin compounds described in U.S. Pat. Nos. 6,281,354 and 6,548,530, US patent publication Nos. 20030050331, 20030064984, 20030073852 and 20040087497 or published in WO 03/022806, which are hereby incorporated by reference in their entireties. Thus, this disclosure also provides methods for localizing ex vivo or in vivo cells expressing Fucosyl-GM1 (e.g., with a detectable label, such as a radioisotope, a fluorescent compound, an enzyme or an enzyme co-factor). Alternatively, the immunoconjugates can be used to kill cells which have Fucosyl-GM1 cell surface receptors by targeting cytotoxins or radiotoxins to Fucosyl-GM1.

Target-specific effector cells, e.g., effector cells linked to compositions (e.g., human antibodies, multispecific and bispecific molecules) of this disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing Fucosyl-GM1 and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of this disclosure and/or effector cells armed with these compositions can be used in conjunction with chemotherapy. Additionally, combination immunotherapy may be used to direct two distinct cytotoxic effector populations toward tumor cell rejection. For example, anti-Fucosyl-GM1 antibodies linked to anti-Fc-gamma RI or anti-CD3 may be used in conjunction with IgG- or IgA-receptor specific binding agents.

Bispecific and multispecific molecules of this disclosure can also be used to modulate FcγR or FcγR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of this disclosure which have complement binding sites, such as portions from IgG1, -2 or -3 or IgM which bind complement, can also be used in the presence of complement. In one embodiment, ex vivo treatment of a population of cells comprising target cells with a binding agent of this disclosure and appropriate effector cells can be supplemented by the addition of complement or serum containing complement. Phagocytosis of target cells coated with a binding agent of this disclosure can be improved by binding of complement proteins. In another embodiment target cells coated with the compositions (e.g., human antibodies, multispecific and bispecific molecules) of this disclosure can also be lysed by complement. In yet another embodiment, the compositions of this disclosure do not activate complement.

The compositions (e.g., human antibodies, multispecific and bispecific molecules and immunoconjugates) of this disclosure can also be administered together with complement. Accordingly, within the scope of this disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of this disclosure and the complement or serum can be administered separately.

Accordingly, patients treated with antibody compositions of this disclosure can be additionally administered (prior to, simultaneously with or following administration of a human antibody of this disclosure) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ) and tumor necrosis factor (TNF).

The compositions (e.g., human antibodies, multispecific and bispecific molecules) of this disclosure can also be used to target cells expressing FcγR or Fucosyl-GM1, for example for labeling such cells. For such use, the binding agent can be linked to a molecule that can be detected. Thus, this disclosure provides methods for localizing ex vivo or in vitro cells expressing Fc receptors, such as FcγR or Fucosyl-GM1. The detectable label can be, e.g., a radioisotope, a fluorescent compound, an enzyme or an enzyme co-factor.

Also within the scope of the present disclosure are kits comprising the antibody compositions of this disclosure (e.g., human antibodies, bispecific or multispecific molecules, or immunoconjugates) and instructions for use. The kit can further contain one more more additional reagents, such as an immunosuppressive reagent, a cytotoxic agent or a radiotoxic agent or one or more additional human antibodies of this disclosure (e.g., a human antibody having a complementary activity which binds to an epitope in the Fucosyl-GM1 antigen distinct from the first human antibody). Kits typically include a label indicating the intended use of the contents of the kit. The term label includes any writing, or recorded material supplied on or with the kit, or which otherwise accompanies the kit.

The present disclosure is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against Fucosyl-GM1

Antigen

Immunization protocols utilized as antigen *Salmonella minnesota* adsorbed fucosyl-GM1 (Northwest Biotherapeutics, Inc.).

Transgenic HuMab and KM Mice™

Fully human monoclonal antibodies to Fucosyl-GM1 were prepared using the HCo7, HCo12, HCo7+HCo12 strains of HuMab transgenic mice and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,770,429; 5,545,806; 5,625,825; and 5,545,807. The HCo12 strain carries the HCo12 human heavy chain transgene as described in Example 2 of WO 01/09187 or example 2 WO 01/14424. The HCo7+HCo12 strain carries both the HCo7 and the HCo12 heavy chain transgenes. The KM strain contains the SC20 transchromosome as described in PCT Publication WO 02/43478. All of these strains are referred to herein as HuMAb mice.

HuMab and KM Immunizations:

To generate fully human monoclonal antibodies to Fucosyl-GM1, HuMab mice and KM mice™ were immunized with Fucosyl-GM1 adsorbed by lyophilization onto the surface of acid treated *Salmonella Minnesota* (Northwest Biotherapeutics, Inc.). General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen.

Transgenic mice were immunized intraperitonealy (IP) or subcutaneously (Sc) with antigen in complete Freund's adjuvant twice, followed by 2-4 weeks IP immunization (up to a total of 8 immunizations) with the antigen in incomplete Freund's adjuvant. The immune response was monitored by ELISA (described below) of sera obtained from retro-orbital bleeds. Mice with sufficient titers of anti-fucosyl-GM1 human immunogolobulin were used for fusions. Mice were boosted intravenously with antigen 3 and 2 days before sacrifice and removal of the spleen.

Selection of HuMab or KM Mice™ Producing Anti-Fucosyl-GM1 Antibodies:

To select HuMab or KM mice™ producing antibodies that bound Fucosyl-GM1, sera from immunized mice were tested by ELISA as described by Fishwild, D. et al. (1996). Briefly, natural fucosyl-GM1 purified from either fucosyl transferase transfectant cell lines (Northwest Biotherapeutics, Inc.) or from bovine brain (Matreya, Inc) was solubilized in methanol at 1 mg/ml and passively adsorbed onto polypropylene microtiter plates, 50 ul/well, by air-drying at room temperature for 1-2 hrs. Similarly, plates coated with related control antigens such as GM1 were prepared as a counter-screen for cross reactive antibodies. Assay plates were then blocked with 250 μl/well of 1% ovalbumin in PBS for 1 hr at room temperature. Dilutions of plasma from fucosyl-GM1 immunized mice were added to each well and incubated for 1-2 hours at ambient temperature. The plates were washed with PBS and then incubated for 1 hour at room temperature with either a goat-anti-human IgG Fc or with goat-anti-human IgM Fc polyclonal antibodies each conjugated to horseradish peroxidase (HRP). After washing, the plates were developed with TMB substrate and analyzed by spectrophotometer at OD 450 nm.

Mice that developed the highest titers of anti-fucosyl-GM1 antibodies were used for fusions. Fusions were performed as described below and hybridoma supernatants were tested for anti-fucosyl-GM1 activity by ELISA.

Generation of Hybridomas Producing Human Monoclonal Antibodies to Fucosyl-GM1:

Splenocytes were isolated from the HuMab® mice and KM-mice™ and were fused to a mouse myeloma cell line either using PEG based upon standard protocols or electric field based electrofusion using a Cyto Pulse large chamber cell fusion electroporator (Cyto Pulse Sciences, Inc., Glen Burnie, Md.). The resulting hybridomas were then screened for the production of antigen-specific antibodies.

Single cell suspensions of splenic lymphocytes from immunized mice were fused to one-fourth the number of P3X63-Ag8.653 non-secreting mouse myeloma cells (ATCC, CRL 1580) or SP2/0 non-secreting mouse myeloma cells (ATCC, CRL 1581) using 50% PEG (Sigma). Cells were plated at a density of about $1\times10^5$/well in flat bottom microtiter plates and incubated approximately 2 weeks in selective medium containing 10% fetal bovine serum, 10% P388DI (ATCC, CRL TIB-63) conditioned medium, 3-5% origen (IGEN) in DMEM (Mediatech, CRL 10013, with high glucose, L-glutamine and sodium pyruvate) plus mM HEPES, 0.055 mM 2-mercaptoethanol, 50 mg/ml gentamicin and 1×HAT (Sigma, CRL P-7185). After 1-2 weeks, cells were cultured in medium in which the HAT was replaced with HT. Individual wells were then screened by ELISA (described above) for human anti-fucosyl-GM1 IgG and IgM antibodies.

The hybridomas with specific binding activity in the ELISA assay screen were further tested by FACS (described below) for specific binding to fucosyl-GM1 adsorbed to mammalian cells. Hybridomas exhibiting the highest specific binding by ELISA and FACS were sub-cloned at least twice by limiting dilution. The resulting stable sub-clones were then cultured in vitro to generate small amounts of monoclonal antibody in tissue culture medium. The ELISA screen was repeated to confirm the activity of the sub-clones. The sub-clones with highest activity in the ELISA were scaled up to produce sufficient conditioned medium (typically 1 L) for purification of monoclonal anti-fucosyl-GM1 for further characterization.

Hybridoma clones 5B1, 5B1a, 7D4, 7E4, 13B8, 13B8a and 18D5 were selected for further analysis.

Example 2

Structural Characterization of Human Monoclonal Antibodies 5B1, 5B1a, 7D4, 7E4, 13B8 and 18D5

The cDNA sequences encoding the heavy and light chain variable regions of the 5B1, 5B1a, 7D4, 7E4, 13B8 and 18D5 monoclonal antibodies were obtained from the 5B1, 5B1a, 7D4, 7E4, 13B8 and 18D5 hybridomas, respectively, using standard PCR techniques and were sequenced using standard DNA sequencing techniques.

The nucleotide and amino acid sequences of the heavy chain variable region of 5B1 are shown in FIG. 1A and in SEQ ID NO:49 and 1, respectively.

The nucleotide and amino acid sequences of the light chain variable region of 5B1 are shown in FIG. 1B and in SEQ ID NO:55 and 7, respectively.

Comparison of the 5B1 heavy chain immunoglobulin sequence to the known human germline immunoglobulin heavy chain sequences demonstrated that the 5B1 heavy chain utilizes a VH segment from human germline VH 3-48, a D segment from the human germline 1-1, and a JH segment from human germline JH 6b. The alignment of the 5B1 VH sequence to the germline VH 3-48 sequence is shown in FIG. 7. Further analysis of the 5B1 VH sequence using the Kabat system of CDR region determination led to the delineation of the heavy chain CDR1, CDR2 and CD3 regions as shown in FIGS. 1A and 7, and in SEQ ID NOs: 13, 19 and 25, respectively.

Comparison of the 5B1 light chain immunoglobulin sequence to the known human germline immunoglobulin light chain sequences demonstrated that the 5B1 light chain utilizes a VL segment from human germline VK L15 and a JK segment from human germline JK 4. The alignment of the 5B1 VL sequence to the germline VK L15 sequence is shown in FIG. 8. Further analysis of the 5B1 VL sequence using the Kabat system of CDR region determination led to the delineation of the light chain CDR1, CDR2 and CD3 regions as shown in FIGS. 1B and 8, and in SEQ ID NOs:31, 37 and 43, respectively.

The nucleotide and amino acid sequences of the heavy chain variable region of 5B1a are shown in FIG. 2A and in SEQ ID NO:50 and 2, respectively.

The nucleotide and amino acid sequences of the light chain variable region of 5B1a are shown in FIG. 2B and in SEQ ID NO:56 and 8, respectively.

Comparison of the 5B 11a heavy chain immunoglobulin sequence to the known human germline immunoglobulin heavy chain sequences demonstrated that the 5B1a heavy chain utilizes a VH segment from human germline VH 3-48, a D segment from the human germline 1-1, and a JH segment from human germline JH 6b. The alignment of the 5B1a VH sequence to the germline VH 3-48 sequence is shown in FIG. 7. Further analysis of the 5B1a VH sequence using the Kabat system of CDR region determination led to the delineation of the heavy chain CDR1, CDR2 and CD3 regions as shown in FIGS. 2A and 7, and in SEQ ID NOs: 14, 20 and 26, respectively.

Comparison of the 5B 11a light chain immunoglobulin sequence to the known human germline immunoglobulin light chain sequences demonstrated that the 5B1a light chain utilizes a VL segment from human germline VK L15 and a JK segment from human germline JK 4. The alignment of the 5B1a VL sequence to the germline VK L15 sequence is shown in FIG. 8. Further analysis of the 5B1a VL sequence using the Kabat system of CDR region determination led to the delineation of the light chain CDR1, CDR2 and CD3 regions as shown in FIGS. 2B and 8, and in SEQ ID NOs:32, 38 and 44, respectively.

The nucleotide and amino acid sequences of the heavy chain variable region of 7D4 are shown in FIG. 3A and in SEQ ID NO:51 and 3, respectively.

The nucleotide and amino acid sequences of the light chain variable region of 7D4 are shown in FIG. 3B and in SEQ ID NO:57 and 9, respectively.

Comparison of the 7D4 heavy chain immunoglobulin sequence to the known human germline immunoglobulin heavy chain sequences demonstrated that the 7D4 heavy chain utilizes a VH segment from human germline VH 3-48, a D segment from the human germline 1-1, and a JH segment from human germline JH 6b. The alignment of the 7D4 VH sequence to the germline VH 3-48 sequence is shown in FIG. 7. Further analysis of the 7D4 VH sequence using the Kabat system of CDR region determination led to the delineation of the heavy chain CDR1, CDR2 and CD3 regions as shown in FIGS. 3A and 7, and in SEQ ID NOs:15, 21 and 27, respectively.

Comparison of the 7D4 light chain immunoglobulin sequence to the known human germline immunoglobulin light chain sequences demonstrated that the 7D4 light chain utilizes a VL segment from human germline VK L15 and a JK segment from human germline JK 4. The alignment of the 7D4 VL sequence to the germline VK L15 sequence is shown in FIG. 8. Further analysis of the 7D4 VL sequence using the Kabat system of CDR region determination led to the delineation of the light chain CDR1, CDR2 and CD3 regions as shown in FIGS. 3B and 8, and in SEQ ID NOs:33, 39 and 45, respectively.

The nucleotide and amino acid sequences of the heavy chain variable region of 7E4 are shown in FIG. 4A and in SEQ ID NO:52 and 4, respectively.

The nucleotide and amino acid sequences of the light chain variable region of 7E4 are shown in FIG. 4B and in SEQ ID NO:58 and 10, respectively.

Comparison of the 7E4 heavy chain immunoglobulin sequence to the known human germline immunoglobulin heavy chain sequences demonstrated that the 7E4 heavy chain utilizes a VH segment from human germline VH 3-48, a D segment from the human germline 1-1, and a JH segment from human germline JH 6b. The alignment of the 7E4 VH sequence to the germline VH 3-48 sequence is shown in FIG. 7. Further analysis of the 7E4 VH sequence using the Kabat system of CDR region determination led to the delineation of the heavy chain CDR1, CDR2 and CD3 regions as shown in FIGS. 4A and 7, and in SEQ ID NOs:16, 22 and 28, respectively.

Comparison of the 7E4 light chain immunoglobulin sequence to the known human germline immunoglobulin light chain sequences demonstrated that the 7E4 light chain utilizes a VL segment from human germline VK L15 and a JK segment from human germline JK 4. The alignment of the 7E4 VL sequence to the germline VK L15 sequence is shown in FIG. 8. Further analysis of the 7E4 VL sequence using the Kabat system of CDR region determination led to the delineation of the light chain CDR1, CDR2 and CD3 regions as shown in FIGS. 4B and 8, and in SEQ ID NOs:34, 40 and 46, respectively.

The nucleotide and amino acid sequences of the heavy chain variable region of 13B8 are shown in FIG. 5A and in SEQ ID NO:53 and 5, respectively.

The nucleotide and amino acid sequences of the light chain variable region of 13B8 are shown in FIG. 5B and in SEQ ID NO:59 and 11, respectively.

Comparison of the 13B8 heavy chain immunoglobulin sequence to the known human germline immunoglobulin heavy chain sequences demonstrated that the 13B8 heavy chain utilizes a VH segment from human germline VH 3-48, a D segment from the human germline 1-1, and a JH segment from human germline JH 6b. The alignment of the 13B8 VH sequence to the germline VH 3-48 sequence is shown in FIG. 7. Further analysis of the 13B8 VH sequence using the Kabat system of CDR region determination led to the delineation of the heavy chain CDR1, CDR2 and CD3 regions as shown in FIGS. 5A and 7, and in SEQ ID NOs:11, 17 and 23, respectively.

Comparison of the 13B8 light chain immunoglobulin sequence to the known human germline immunoglobulin light chain sequences demonstrated that the 13B8 light chain utilizes a VL segment from human germline VK L15 and a JK segment from human germline JK 4. The alignment of the 13B8 VL sequence to the germline VK L15 sequence is shown in FIG. 8. Further analysis of the 13B8 VL sequence using the Kabat system of CDR region determination led to the delineation of the light chain CDR1, CDR2 and CD3 regions as shown in FIGS. 5B and 8, and in SEQ ID NOs:35, 41 and 47, respectively.

The nucleotide and amino acid sequences of the heavy chain variable region of 3C4 are shown in FIG. 6A and in SEQ ID NO:54 and 63, respectively.

The nucleotide and amino acid sequences of the light chain variable region of 3C4 are shown in FIG. 6B and in SEQ ID NO:60 and 64, respectively.

Comparison of the 18D5 heavy chain immunoglobulin sequence to the known human germline immunoglobulin heavy chain sequences demonstrated that the 18D5 heavy chain utilizes a VH segment from human germline VH 3-48, a D segment from human germline 1-1, and a JH segment from human germline JH 6b. The alignment of the 18D5 VH sequence to the germline VH 3-48 sequence is shown in FIG. 7. Further analysis of the 18D5 VH sequence using the Kabat system of CDR region determination led to the delineation of the heavy chain CDR1, CDR2 and CD3 regions as shown in FIG. 7, and in SEQ ID NOs:18, 24 and 30, respectively.

Comparison of the 18D5 light chain immunoglobulin sequence to the known human germline immunoglobulin light chain sequences demonstrated that the 18D5 light chain utilizes a VL segment from human germline VK L15 and a JK segment from human germline JK 4. The alignment of the 18D5 VL sequence to the germline VK L15 sequence is shown in FIG. 8. Further analysis of the 18D5 VL sequence using the Kabat system of CDR region determination led to the delineation of the light chain CDR1, CDR2 and CD3 regions as shown in FIG. 8, and in SEQ ID NOs:36, 42 and 48, respectively.

Example 3

Preparation of Cells Doped with Fucosyl-GM1

Cells were prepared that contained fucosyl-GM1 embedded in the plasma membrane for use in binding assays. Purified fucosyl-GM1 was solubilized in a 1:1 mixture of chloroform:methanol in a glass tube and evaporated to dryness under nitrogen. PBS without Ca or Mg was added to the dry fucosyl-GM1 such that the concentration of antigen was 200 μg/ml; an emulsion was created by vortexing for 5 minutes followed by sonication for 5 minutes. A suspension of target cells, typically HEK 293 (human kidney, ATCC #CRL-1573) or Daudi (human Burkitt's lymphoma, ATCC #CCL-213) was prepared in PBS at $2\times10^6$ cells/ml. Equal volumes of fucosyl-GM1 emulsion and cell suspension were mixed to a final concentration of 100 μg antigen/$10^6$ cells/ml. Cells plus antigen were incubated to allow fucosyl-GM1 intercalation into the membrane for 15 minutes at 37° C., followed by 30 minutes at room temperature with occasional mixing throughout. Cells were centrifuged at 1000 rpm for 10 minutes. The supernate was discarded and the "doped" cells were resuspended at a density of $4\times10^6$ cells/ml in FACS buffer (PBS without Ca or Mg+1% human serum+2% FBS+2 mM EDTA). Similarly, control cells were prepared "doped" with a related antigen such as GM1 or with no antigen.

Example 4

Characterization of Binding Specificity and Binding Kinetics of Anti-Fucosyl-GM1 Human Monoclonal Antibodies Binding Specificity by ELISA Purified, monoclonal, human anti-Fucosyl-GM1 antibodies were tested for specific binding to purified fucosyl-GM1 by ELISA, by both recombinant antigen and doped cells. All procedures were performed on ice. Conditioned medium from ELISA positive hybridoma cultures were mixed with antigen or cells in "V" bottom plates and were incubated 1 hour. Cells were washed and bound antibody was detected with an HRP conjugated mouse anti-human IgG Fc secondary antibody. After washing, the plates were developed with a colorimetric substrate, pelleted by centrifugation and supernate was transferred to a flat-bottom microtiter assay plate for analysis by spectrophotometer. The results are shown in FIGS. 9 (antigen ELISA) and 10 (whole cell ELISA). The anti-fucosyl-GM1 antibodies were shown to bind specifically to fucosyl-GM1.

Binding Specificity by Flow Cytometry

Naturally expressing fucosy-GM1 positive cells lines such as H-4-II-E (Rat hepatoma ATCC#CRL-1548) or DMS-79 (Human SCLC ATCC #CRL-2049) were used to determine the specificity of Fucosyl-GM1 human monoclonal antibodies by flow cytometry. All staining procedures were performed on ice. Binding of an anti-Fucosyl-GM1 human monoclonal antibody was assessed by incubating the transfected cells with the anti-Fucosyl-GM1 human monoclonal antibody at a concentration of 10 μg/ml. The cells were washed and binding was detected with a FITC-labeled anti-human IgG Ab. Flow cytometric analyses were performed using a FACScan flow cytometry (Becton Dickinson, San Jose, Calif.). The results are depicted in FIG. 11. The anti-Fucosyl-GM1 human monoclonal antibody bound to the H-4-II-E and DMS-79 cell lines. This data demonstrates the specificity of anti-Fucosyl-GM1 human monoclonal antibodies for Fucosyl-GM1.

Example 5

Internalization of Anti-Fucosyl-GM1 Monoclonal Antibody

Anti-Fucosyl-GM1 HuMAbs were tested for the ability to internalize into Fucosyl-GM1-expressing cell lines using a Hum-Zap internalization assay. The Hum-Zap assay tests for internalization of a primary human antibody through binding of a secondary antibody with affinity for human IgG conjugated to the toxin saporin.

Cell lines expressing fucosyl-GM1 (H-4-II-E or DMS 79) were suspended in culture medium and dispensed into microtiter cell culture plates at 7500 cells/well. Serial dilutions of test antibodies and isotype controls are prepared in culture medium and mixed with a 2:1 molar excess of saporin conjugated secondary antibody (Hum-Zap™, Advanced Targeting Systems, San Diego, Calif., IT-22-25) for 1 hour on ice. Antibody plus saporin conjugate mixtures were then mixed with cells and incubated at 37° C., 48-72 hours. Cell viability was measured with the addition of MTS (Promega) O.D. is read after a further 4 hour incubation, with absorbance inversely proportional to internalization. The results are shown in FIG. 12. This data demonstrates that the human anti-fucosyl GM1 antibodies can internalize into cell lines expressing fucosyl-GM1.

Example 6

Complement Dependent Cytotoxicity Effect of Anti-Fucosyl GM1 Antibodies

Target cells, either "doped" or naturally expressing cell lines were suspended to $10^6$/mL in CDC buffer (RPMI1640). Human complement (HC) was diluted 1:3 in cell line growth medium. Serial dilutions of test antibodies and isotype controls were prepared. Cells, complement and antibodies were mixed in equal volumes in a microtiter assay plate and incubated at 37° C. for 2 hours. Alamar blue was added to each well and the plates were incubated for an additional 21 hrs at 37° C. The plates were read on a fluorescent plate reader using a 530 nm absorption/590 nm emission profile, with cell viability being proportional to fluorescence units. The results are shown in FIG. 13. Human and mouse control antibodies exhibit robust, dose dependant CDC activity on both DMS 79 and H-4-II-E cells. Isotype control antibodies show no significant cytotoxicity. CDC activity on fucosyl-GM1 negative cell lines, such as Ramos and ARH77 is negligible Example 7

Assessment of ADCC Activity of Anti-Fucosyl GM1 Antibodies

In this example, anti-fucosyl GM1 monoclonal antibodies were tested for the ability to kill fucosyl GM1 expressing cell lines in the presence of effector cells via antibody dependent cellular cytotoxicity (ADCC) in a fluorescence cytotoxicity assay.

ADCC activity is measured using the Delfia System (Perkin-Elmer). Briefly, effector cells are cultured from human peripheral blood mononuclear cells (PBMC) by overnight stimulation with 200 u/ml IL-2 and are resuspended to $2\times10^7$/ml. Target cells are diluted to $10^6$/ml and are loaded with a fluorescence enhancing ligand (BATDA) by incubating 20 minutes and are diluted to $2\times10^7$ cells/ml. Effector and target cells are combined at a 100:1 ratio in a microtiter assay plate and mixed with a serial dilution of test antibody and isotype control. Plates are incubated 1 hour at 37° C., centrifuged to pellet cells and 20 ul of supernate is removed and mixed with Eu solution (Perkin-Elmer). Fluorescence resulting from released ligand combined with Eu is measured on a Fusion plate reader (Perkin-Elmer) and is proportional to cell lysis. Assay wells with effector cells in the absence of antibody and with detergent control for background lysis and complete lysis respectively allowing antibody specific lysis to be calculated. The results are shown in FIG. 14. This data demonstrates that the anti-fucosyl GM1 antibodies are cytotoxic to cells expressing fucosyl-GM1 on the cell surface.

Example 8

Immunohistochemistry of Lung Carcinoma

The ability of the anti-fucosyl-GM1 HuMAb 7E4 to recognize fucosyl-GM1 by IHC was examined using clinical biopsies of small cell lung carcinoma (SCLC) and non-small cell lung carcinoma (NSCLC).

For immunohistochemistry, 5 mm frozen sections (Ardais Inc, USA) prepared from clinical biopsies of small cell lung carcinoma (SCLC) and non-small cell lung carcinoma (NSCLC). After drying for 30 minutes, sections were fixed with methanol (at room temperature for 10 minutes) and air-dried for 5 minutes. Slides were rinsed in PBS and then pre-incubated with 10% normal goat serum in PBS for 20 min and subsequently incubated with 10 mg/ml biotinylated 7E4 in PBS with 10% normal goat serum for 30 min at room temperature. Slides were washed three times with PBS and then incubated for 30 min with streptavidin-FITC (DAKO) at room temperature. Slides were washed again with PBS and incubated with Goat anti-FITC HRP conjugate (DAKO) for 30 minutes at room temperature. Slides were washed again 3× with PBS. Diaminobenzidine (Sigma) was used as an HRP substrate, resulting in brown staining of tissues positive for 7E4 binding. After washing with distilled water, slides were counter-stained with hematoxyllin for 1 min to show tissue structure. Subsequently, slides were washed for 10 seconds in running distilled water and mounted in glycergel (DAKO). Clinical biopsy immunohistochemical staining displayed positive staining in both the SCLC and NSCLC sections. Only malignant cells were positive in each case, adjacent normal lung tissue was not stained. Overall prevalence in lung carcinoma was 5/13 samples tested (2/6 SCLC and 3/7 NSCLC). IHC was negative for 7E4 binding to normal lung tissue.

Example 9

Production of Nonfucosylated HuMAbs

Antibodies with reduced amounts of fucosyl residues have been demonstrated to increase the ADCC ability of the antibody. In this example, an anti-Fucosyl GM1 HuMAb is produced that is lacking in fucosyl residues.

The CHO cell line Ms704-PF, which lacks the fucosyltransferase gene, FUT 8 (Biowa, Inc., Princeton, N.J.) is electroporated with a vector which expresses the heavy and light chains of an anti-Fucosyl GM1 HuMAb. Drug-resistant clones are selected by growth in Ex-Cell 325-PF CHO media (JRH Biosciences, Lenexa, Kans.) with 6 mM L-glutamine and 500 μl/ml G418 (Invitrogen, Carlsbad, Calif.). Clones are screened for IgG expression by standard ELISA assay.

Example 10

In Vivo Efficacy of Anti-Fucosyl-GM1 Human Monoclonal Antibodies

DMS79 small cell lung cancer cells (Fucosyl-GM1$^+$) were subcutaneously implanted in in male SCID mice ($5\times10^6$ cells/mouse) for a time sufficient (about 8 days) to permit the formation of tumors. On day 8 post-implantation, tumor measurements were taken and mice were randomized based on mean tumor volume (about 200 mm$^3$) into six groups of eight mice each for subsequent antibody therapy. On days 8 11, 15, 18, and 22 post-implantation, mice were injected intraperitoneally (i.p.) as the following groups: (A) PBS (vehicle control); (B) human IgG1 (isotype control) at 30 mg/kg per mouse; (C) anti-Fucosyl-GM1 monoclonal antibody 5B1 at 10 mg/kg per mouse; (D) anti-Fucosyl-GM1 monoclonal antibody 5B1 at 30 mg/kg per mouse; (E) anti-Fucosyl-GM1 monoclonal antibody 7E4 at 10 mg/kg per mouse; or (F) anti-Fucosyl-GM1 monoclonal antibody 7E4 at 30 mg/kg per mouse. The monoclonal antibody compositions used in these experiments had low levels of endotoxin and did not significantly aggregate. Using an electronic precision caliper, tumors were measured three dimensionally (height×width×length) and tumor volume was calculated. Tumor measurements were taken twice a week for the duration of the experiment (61 days). Mice were euthanized when the tumors reached a designated tumor end-point (a particular tumor volume such as 1500 mm$^3$ and/or when the mice showed sign of discomfort or greater than about 15% weight loss).

To examine whether the anti-Fucosyl-GM1 monoclonal antibodies delayed tumor growth, the day tumor reached a volume of 1000 mm$^3$ was monitored. Both of the 7E4 and 5B1 anti-Fucosyl-GM1 monoclonal antibodies significantly delayed tumor growth compared to vehicle and isotype controls (see Table 1). The antibody efficacy appears to be dose-dependant with the 30 mg/kg treatment groups showing a greater response in each case. Moreover, tumor volumes in mice treated with the 7E4 antibody at 30 mg/kg never reached 1000 mm$^3$ and had a mean tumor volume of 600 mm$^3$ at the termination of the study on day 61.

TABLE 1

| Treatment | Day Tumor Volume at 1000 mm$^3$ |
|---|---|
| PBS (vehicle control) | 34 |
| h-IgG1 (isotype control) | 32 |
| Anti-5B1 (10 mg/kg) | 56 |
| Anti-5B1 (30 mg/kg) | 60 |
| Anti-7E4 (10 mg/kg) | 57 |
| Anti-7E4 (30 mg/kg) | >61 |

To examine whether Fucosyl-GM1 continued to be expressed by the DMS79 cells in vivo, binding of monoclonal antibodies 7E4 and 5B1 to DMS79 cells was analyzed by FACS prior to implantation and after recovery of DMS79 cells from untreated tumors. The antibodies bound pre- and post-implantation of DMS79 cells demonstrated that Fucosyl-GM1 expression levels were maintained in vivo (FIG. 11C).

Figure 16:
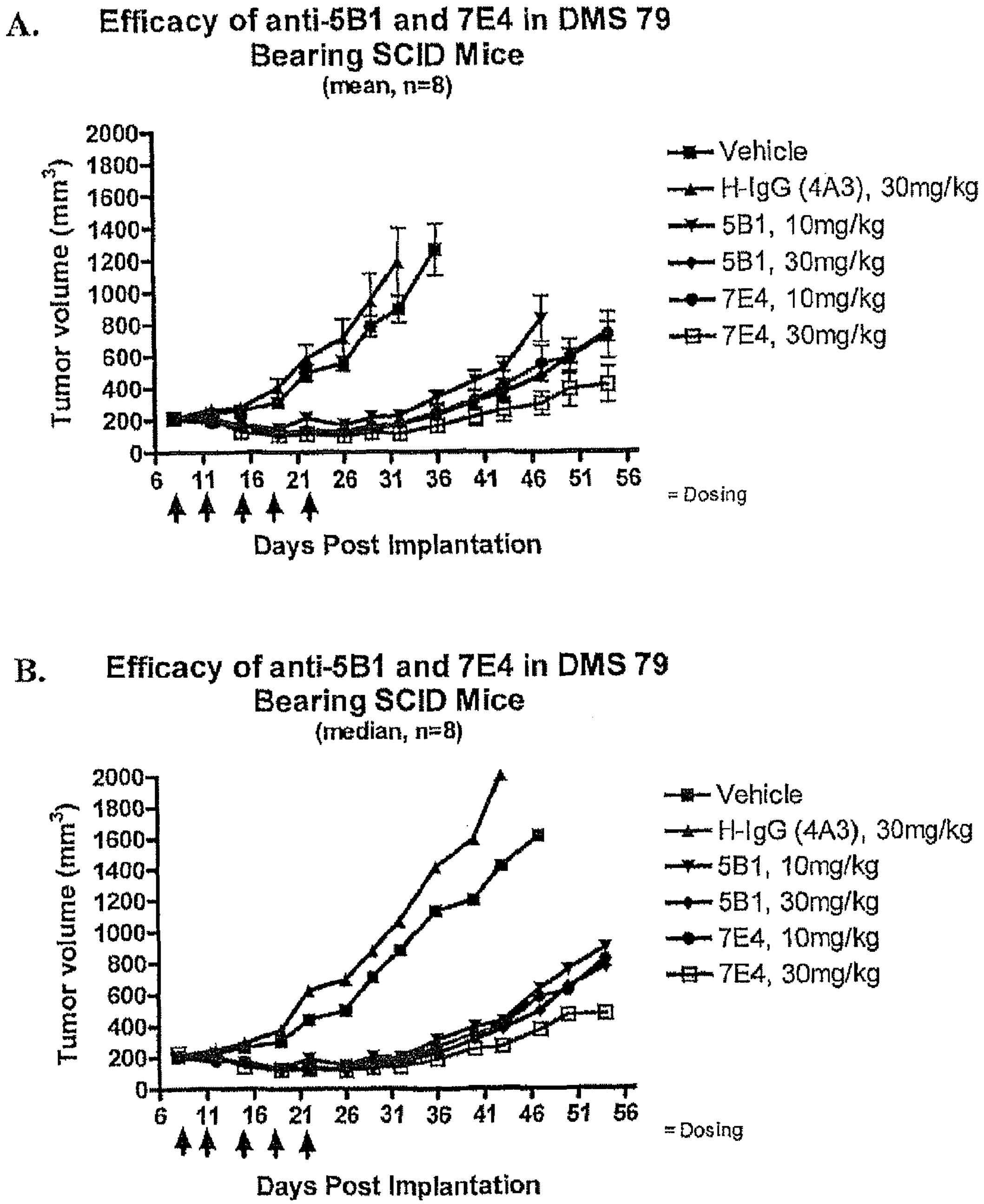

FIG. 15A shows that all control mice (Groups A and B) except one reached the tumor end-point well before day 61. FIG. 15B shows that the group treated with 10 mg/kg of anti-Fucosyl-GM1 5B1 antibody (Group C) had two mice that reached the tumor end-point and six mice with tumors having a volume ranging from about 600 mm$^3$ to 1000 mm$^3$, while none of the eight mice in the group treated with 30 mg/kg of anti-Fucosyl-GM1 5B1 antibody (Group D) reached the tumor end-point by day 61 (having a volume of 1000 mm$^3$ or less). FIG. 15C shows that none of the eight mice in the group treated with 10 mg/kg anti-Fucosyl-GM1 monoclonal antibody 7E4 (Group E) reached the tumor end-point by day 61 (having a volume of about 1200 mm$^3$ or less, and one mouse being tumor free). FIG. 15C also shows that none of the eight mice in the group treated with 30 mg/kg anti-Fucosyl-GM1 monoclonal antibody 7E4 (Group F) reached the tumor end-point by day 61 (having a volume of about 800 mm$^3$ or less, and two mice being tumor free). FIG. 16 shows the (A) mean and (B) median tumor volumes measured at day 61. The antibody efficacy appears to be dose-dependant with the 30 mg/kg treatment groups showing a greater response in each case as compared to the controls.

TABLE 2

| Group | Tumor Growth Inhibition (TGI) (Day 32) Mean Vol.* | % | MedianVol.* | % | Tumor Free, Day 40 % (#/total) |
|---|---|---|---|---|---|
| PBS | 897 | — | 882 | — | — |
| h-IgG1 | 1189 | — | 1066 | — | — |
| Anti-5B1 (10 mg/kg) | 227 | 81 | 201 | 81 | — |
| Anti-5B1 (30 mg/kg) | 174 | 85 | 172 | 84 | — |
| Anti-7E4 (10 mg/kg) | 177 | 85 | 175 | 84 | 12.5% (1/8) |
| Anti-7E4 (30 mg/kg) | 116 | 90 | 141 | 87 | 25% (2/8) |

This study indicates that, in a murine tumor model, treatment with anti-Fucosyl-GM1 antibody functions in a dose dependent manner and has a significantly greater effect on tumor growth than the vehicle and isotype controls. The anti-Fucosyl-GM1 antibody treatment also did not cause the mice to lose weight or result in any other significant side-effects, indicating that these antibodies are safe and well tolerated (FIG. 17). Indeed, the anti-Fucosyl-GM1 antibodies showed a percent tumor growth inhibition (TGI %) ranging from 81 to 90% on day 32 (Table 2). In addition, treatment with antibody 7E4 at a 30 mg/kg dose resulted in 25% of the mice being tumor free.

The present disclosure is not to be limited in scope by the specific embodiments described herein. Indeed, various modifications of this disclosure, in addition to those described herein, will become apparent to those skilled in the art from the foregoing description and the accompanying figures. Such modifications are intended to fall within the scope of the appended claims. This disclosure is, therefore, to be limited only by the terms of the appended claims along with the full scope of equivalents to which the claims are entitled.

SEQUENCE LISTING

| SEQ ID NO: | SEQUENCE |
|---|---|
| 1 | VH a.a. 5B1 |
| 2 | VH a.a. 5B1a |
| 3 | VH a.a. 7D4 |
| 4 | VH a.a. 7E4 |
| 5 | VH a.a. 13B8 |
| 6 | VH a.a. 18D5 |
| 7 | VK a.a. 5B1 |
| 8 | VK a.a. 5B1a |
| 9 | VK a.a. 7D4 |
| 10 | VK a.a. 7E4 |
| 11 | VK a.a. 13B8 |
| 12 | VK a.a. 18D5 |
| 13 | VH CDR1 a.a. 5B1 |
| 14 | VH CDR1 a.a. 5B1a |
| 15 | VH CDR1 a.a. 7D4 |
| 16 | VH CDR1 a.a. 7E4 |
| 17 | VH CDR1 a.a. 13B8 |
| 18 | VH CDR1 a.a. 18D5 |
| 19 | VH CDR2 a.a. 5B1 |
| 20 | VH CDR2 a.a. 5B1a |
| 21 | VH CDR2 a.a. 7D4 |
| 22 | VH CDR2 a.a. 7E4 |
| 23 | VH CDR2 a.a. 13B8 |
| 24 | VH CDR2 a.a. 18D5 |
| 25 | VH CDR3 a.a. 5B1 |
| 26 | VH CDR3 a.a. 5B1a |
| 27 | VH CDR3 a.a. 7D4 |
| 28 | VH CDR3 a.a. 7E4 |
| 29 | VH CDR3 a.a. 13B8 |
| 30 | VH CDR3 a.a. 18D5 |
| 31 | VK CDR1 a.a. 5B1 |
| 32 | VK CDR1 a.a. 5B1a |
| 33 | VK CDR1 a.a. 7D4 |
| 34 | VK CDR1 a.a. 7E4 |
| 35 | VK CDR1 a.a. 13B8 |
| 36 | VK CDR1 a.a. 18D5 |
| 37 | VK CDR2 a.a. 5B1 |
| 38 | VK CDR2 a.a. 5B1a |
| 39 | VK CDR2 a.a. 7D4 |
| 40 | VK CDR2 a.a. 7E4 |
| 41 | VK CDR2 a.a. 13B8 |
| 42 | VK CDR2 a.a. 18D5 |
| 43 | VK CDR3 a.a. 5B1 |
| 44 | VK CDR3 a.a. 5B1a |
| 45 | VK CDR3 a.a. 7D4 |
| 46 | VK CDR3 a.a. 7E4 |
| 47 | VK CDR3 a.a. 13B8 |
| 48 | VK CDR3 a.a. 18D5 |
| 49 | VH n.t. 5B1 |
| 50 | VH n.t. 5B1a |
| 51 | VH n.t. 7D4 |
| 52 | VH n.t. 7E4 |
| 53 | VH n.t. 13B8 |
| 54 | VH n.t. 3C4 |
| 55 | VK n.t. 5B1 |
| 56 | VK n.t. 5B1a |
| 57 | VK n.t. 7D4 |
| 58 | VK n.t. 7E4 |
| 59 | VK n.t. 13B8 |
| 60 | VK n.t. 3C4 |
| 61 | VH 3-48 germline a.a. |
| 62 | VK L15 germline a.a. |

We claim:

1. A method of treating a disease characterized by growth of tumor cells expressing Fucosyl-GM1, comprising administering to a subject a human monoclonal antibody that specifically binds to Fucosyl-GM1, or antigen-binding portion thereof, in an amount effective to treat the disease, wherein the human monoclonal antibody or antigen binding portion thereof cross-competes for binding to Fucosyl-GM1 with an antibody comprising:

(a) a heavy chain variable region comprising the amino acid sequence of SEQ ID NO: 4; and (b) a light chain variable region comprising the amino acid sequence of SEQ ID NO: 10.

2. The method of claim 1, wherein the disease is cancer.

3. The method of claim 2, wherein the cancer is lung cancer.

4. The method of claim 3, wherein the lung cancer is small cell lung cancer.

5. The method of claim 3, wherein the lung cancer is non-small cell lung cancer.

6. The method of claim 1, wherein the subject is human.

7. The method of claim 1, wherein the antibody, or antigen-binding portion thereof, comprises:

(a) a heavy chain variable region CDR1 domain comprising SEQ ID NO:16;

(b) a heavy chain variable region CDR2 domain comprising SEQ ID NO:22;

(c) a heavy chain variable region CDR3 domain comprising SEQ ID NO:28;

(d) a light chain variable region CDR1 domain comprising SEQ ID NO:34;

(e) a light chain variable region CDR2 domain comprising SEQ ID NO:40; and (f) a light chain variable region CDR3 domain comprising SEQ ID NO:46.

8. The method of claim 7, wherein the antibody, or antigen-binding portion thereof, comprises:

(a) a heavy chain variable region comprising the amino acid sequence of SEQ ID NO:4; and (b) a light chain variable region comprising the amino acid sequence of SEQ ID NO:10.

9. The method of claim 1, wherein the antibody is a human antibody.

10. The method of claim 1, wherein the antibody is a chimeric antibody or a humanized antibody.

11. The method of claim 1, wherein the antibody is a full-length antibody of an IgG1 isotype or an IgG4 isotype.

12. The method of claim 1, wherein the antibody is nonfucosylated.

13. The method of claim 1, wherein the antibody or antigen-binding portion thereof, is linked to a therapeutic agent.

14. The method of claim 13, wherein the therapeutic agent is a cytotoxin or a radioactive agent.

15. The method of claim 1, wherein the antibody is administered by a route selected from subcutaneously, intravenously, intramuscularly, intradermally, and intraperitoneally.

16. The method of claim 1, further comprising administering to the subject a second anti-neoplastic agent.

* * * * *

SEQUENCE LISTING

```
<160> NUMBER OF SEQ ID NOS: 77

<210> SEQ ID NO 1
<211> LENGTH: 122
<212> TYPE: PRT
<213> ORGANISM: Homo sapiens

<400> SEQUENCE: 1

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Thr Phe Ser Arg Tyr
            20                  25                  30

Lys Met Asn Trp Val Arg Gln Ala Pro Gly Lys Gly Leu Glu Trp Val
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Gly Thr Val Thr Thr Tyr Tyr Tyr Tyr Phe Gly Met Asp Val Trp
            100                 105                 110
```

```
Gly His Gly Thr Thr Val Thr Val Ser Ser
        115                 120


<210> SEQ ID NO 2
<211> LENGTH: 121
<212> TYPE: PRT
<213> ORGANISM: Homo sapiens

<400> SEQUENCE: 2

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Thr Phe Ser Arg Tyr
            20                  25                  30

Lys Met Asn Trp Val Arg Gln Ala Pro Gly Lys Gly Leu Glu Trp Val
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Gly Thr Val Thr Thr Tyr Tyr Tyr Phe Gly Met Asp Val Trp Gly
            100                 105                 110

His Gly Thr Thr Val Thr Val Ser Ser
        115                 120


<210> SEQ ID NO 3
<211> LENGTH: 122
<212> TYPE: PRT
<213> ORGANISM: Homo sapiens

<400> SEQUENCE: 3

Glu Val Gln Leu Val Glu Ser Gly Gly Gly Leu Val Gln Pro Gly Glu
1               5                   10                  15

Ser Leu Arg Leu Ser Cys Val Val Ser Gly Phe Thr Phe Ser Arg Tyr
            20                  25                  30

Lys Met Asn Trp Val Arg Gln Ala Pro Gly Lys Gly Leu Glu Trp Ile
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Asp Glu Asp Thr Ala Val Tyr Tyr Cys
                85                  90                  95

Ala Gly Thr Val Thr Thr Tyr Tyr Tyr Tyr Phe Gly Met Asp Val Trp
            100                 105                 110

Gly Leu Gly Thr Thr Val Thr Val Ser Ser
        115                 120


<210> SEQ ID NO 4
<211> LENGTH: 122
<212> TYPE: PRT
<213> ORGANISM: Homo sapiens

<400> SEQUENCE: 4

Glu Val Gln Leu Val Glu Ser Gly Gly Gly Ser Val Gln Pro Gly Glu
1               5                   10                  15

Ser Leu Arg Leu Ser Cys Val Ala Ser Gly Phe Thr Phe Ser Arg Tyr
```

```
            20                  25                  30

Lys Met Asn Trp Val Arg Gln Ala Pro Gly Lys Gly Leu Glu Trp Val
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Gly Thr Val Thr Thr Tyr Tyr Tyr Asp Phe Gly Met Asp Val Trp
            100                 105                 110

Gly Gln Gly Thr Thr Val Thr Val Ser Ser
        115                 120


<210> SEQ ID NO 5
<211> LENGTH: 122
<212> TYPE: PRT
<213> ORGANISM: Homo sapiens

<400> SEQUENCE: 5

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Thr Leu Ser Arg Tyr
            20                  25                  30

Lys Met Asn Trp Val Arg Gln Ala Pro Gly Lys Gly Leu Glu Trp Ile
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Ser Ala Val Tyr Tyr Cys
                85                  90                  95

Ala Gly Thr Val Thr Thr Tyr Tyr Tyr Tyr Phe Gly Met Asp Val Trp
            100                 105                 110

Gly Gln Gly Thr Thr Val Thr Val Ser Ser
        115                 120


<210> SEQ ID NO 6
<211> LENGTH: 122
<212> TYPE: PRT
<213> ORGANISM: Homo sapiens

<400> SEQUENCE: 6

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Thr Phe Ser Arg Tyr
            20                  25                  30

Lys Met Asn Trp Val Arg Gln Ala Pro Gly Lys Gly Leu Glu Trp Ile
        35                  40                  45

Ser Tyr Ile Ser Arg Ser Gly Arg Asp Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Asp Glu Asp Thr Ala Val Tyr Tyr Cys
                85                  90                  95

Ala Gly Thr Val Thr Thr Tyr Tyr Tyr Tyr Phe Gly Met Asp Val Trp
```

```
            100                 105                 110

Gly Leu Gly Thr Thr Val Thr Val Ser Ser
        115                 120


<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105


<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105


<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

-continued

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 12
<211> LENGTH: 107
<212> TYPE: PRT
<213> ORGANISM: Homo sapiens

<400> SEQUENCE: 12

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105


<210> SEQ ID NO 13
<211> LENGTH: 5
<212> TYPE: PRT
<213> ORGANISM: Homo sapiens

<400> SEQUENCE: 13

Arg Tyr Lys Met Asn
1               5


<210> SEQ ID NO 14
<211> LENGTH: 5
<212> TYPE: PRT
<213> ORGANISM: Homo sapiens

<400> SEQUENCE: 14

Arg Tyr Lys Met Asn
1               5


<210> SEQ ID NO 15
<211> LENGTH: 5
<212> TYPE: PRT
<213> ORGANISM: Homo sapiens

<400> SEQUENCE: 15

Arg Tyr Lys Met Asn
1               5


<210> SEQ ID NO 16
<211> LENGTH: 5
<212> TYPE: PRT
<213> ORGANISM: Homo sapiens

<400> SEQUENCE: 16

Arg Tyr Lys Met Asn
1               5


<210> SEQ ID NO 17
<211> LENGTH: 5
<212> TYPE: PRT
<213> ORGANISM: Homo sapiens

<400> SEQUENCE: 17

Arg Tyr Lys Met Asn
1               5


<210> SEQ ID NO 18
<211> LENGTH: 5
```

<212> TYPE: PRT
<213> ORGANISM: Homo sapiens

<400> SEQUENCE: 18

Arg Tyr Lys Met Asn
1 5

<210> SEQ ID NO 19
<211> LENGTH: 17
<212> TYPE: PRT
<213> ORGANISM: Homo sapiens

<400> SEQUENCE: 19

Tyr Ile Ser Arg Ser Gly Arg Asp Ile Tyr Tyr Ala Asp Ser Val Lys
1 5 10 15

Gly

<210> SEQ ID NO 20
<211> LENGTH: 17
<212> TYPE: PRT
<213> ORGANISM: Homo sapiens

<400> SEQUENCE: 20

Tyr Ile Ser Arg Ser Gly Arg Asp Ile Tyr Tyr Ala Asp Ser Val Lys
1 5 10 15

Gly

<210> SEQ ID NO 21
<211> LENGTH: 17
<212> TYPE: PRT
<213> ORGANISM: Homo sapiens

<400> SEQUENCE: 21

Tyr Ile Ser Arg Ser Gly Arg Asp Ile Tyr Tyr Ala Asp Ser Val Lys
1 5 10 15

Gly

<210> SEQ ID NO 22
<211> LENGTH: 17
<212> TYPE: PRT
<213> ORGANISM: Homo sapiens

<400> SEQUENCE: 22

Tyr Ile Ser Arg Ser Gly Arg Asp Ile Tyr Tyr Ala Asp Ser Val Lys
1 5 10 15

Gly

<210> SEQ ID NO 23
<211> LENGTH: 17
<212> TYPE: PRT
<213> ORGANISM: Homo sapiens

<400> SEQUENCE: 23

Tyr Ile Ser Arg Ser Gly Arg Asp Ile Tyr Tyr Ala Asp Ser Val Lys
1 5 10 15

Gly

<210> SEQ ID NO 24
<211> LENGTH: 17
<212> TYPE: PRT
<213> ORGANISM: Homo sapiens

<400> SEQUENCE: 24

Tyr Ile Ser Arg Ser Gly Arg Asp Ile Tyr Tyr Ala Asp Ser Val Lys
1 5 10 15

Gly

<210> SEQ ID NO 25
<211> LENGTH: 13
<212> TYPE: PRT
<213> ORGANISM: Homo sapiens

<400> SEQUENCE: 25

Thr Val Thr Thr Tyr Tyr Tyr Tyr Phe Gly Met Asp Val
1 5 10

<210> SEQ ID NO 26
<211> LENGTH: 12
<212> TYPE: PRT
<213> ORGANISM: Homo sapiens

<400> SEQUENCE: 26

Thr Val Thr Thr Tyr Tyr Tyr Phe Gly Met Asp Val
1 5 10

<210> SEQ ID NO 27
<211> LENGTH: 13
<212> TYPE: PRT
<213> ORGANISM: Homo sapiens

<400> SEQUENCE: 27

Thr Val Thr Thr Tyr Tyr Tyr Tyr Phe Gly Met Asp Val
1 5 10

<210> SEQ ID NO 28
<211> LENGTH: 13
<212> TYPE: PRT
<213> ORGANISM: Homo sapiens

<400> SEQUENCE: 28

Thr Val Thr Thr Tyr Tyr Tyr Asp Phe Gly Met Asp Val
1 5 10

<210> SEQ ID NO 29
<211> LENGTH: 13
<212> TYPE: PRT
<213> ORGANISM: Homo sapiens

<400> SEQUENCE: 29

Thr Val Thr Thr Tyr Tyr Tyr Tyr Phe Gly Met Asp Val
1 5 10

<210> SEQ ID NO 30
<211> LENGTH: 13
<212> TYPE: PRT
<213> ORGANISM: Homo sapiens

<400> SEQUENCE: 30

Thr Val Thr Thr Tyr Tyr Tyr Tyr Phe Gly Met Asp Val
1 5 10

<210> SEQ ID NO 31
<211> LENGTH: 11
<212> TYPE: PRT
<213> ORGANISM: Homo sapiens

<400> SEQUENCE: 31

Arg Ala Ser Gln Gly Ile Ser Ser Trp Leu Ala
1 5 10

<210> SEQ ID NO 32
<211> LENGTH: 11
<212> TYPE: PRT
<213> ORGANISM: Homo sapiens

<400> SEQUENCE: 32

Arg Ala Ser Gln Gly Ile Ser Ser Trp Leu Ala
1 5 10

<210> SEQ ID NO 33
<211> LENGTH: 11
<212> TYPE: PRT
<213> ORGANISM: Homo sapiens

<400> SEQUENCE: 33

Arg Ala Ser Gln Gly Ile Ser Ser Trp Leu Ala
1 5 10

<210> SEQ ID NO 34
<211> LENGTH: 11
<212> TYPE: PRT
<213> ORGANISM: Homo sapiens

<400> SEQUENCE: 34

Arg Ala Ser Gln Gly Ile Ser Ser Trp Leu Ala
1 5 10

<210> SEQ ID NO 35
<211> LENGTH: 11
<212> TYPE: PRT
<213> ORGANISM: Homo sapiens

<400> SEQUENCE: 35

Arg Ala Ser Gln Gly Ile Ser Ser Trp Leu Ala
1 5 10

<210> SEQ ID NO 36
<211> LENGTH: 11
<212> TYPE: PRT
<213> ORGANISM: Homo sapiens

<400> SEQUENCE: 36

Arg Ala Ser Gln Gly Ile Ser Ser Trp Leu Ala
1 5 10

<210> SEQ ID NO 37
<211> LENGTH: 7
<212> TYPE: PRT
<213> ORGANISM: Homo sapiens

<400> SEQUENCE: 37

Ala Ala Ser Ser Leu Gln Ser
1 5

<210> SEQ ID NO 38
<211> LENGTH: 7
<212> TYPE: PRT
<213> ORGANISM: Homo sapiens

<400> SEQUENCE: 38

-continued

Ala Ala Ser Ser Leu Gln Ser
1 5

<210> SEQ ID NO 39
<211> LENGTH: 7
<212> TYPE: PRT
<213> ORGANISM: Homo sapiens

<400> SEQUENCE: 39

Ala Ala Ser Ser Leu Gln Ser
1 5

<210> SEQ ID NO 40
<211> LENGTH: 7
<212> TYPE: PRT
<213> ORGANISM: Homo sapiens

<400> SEQUENCE: 40

Ala Ala Ser Ser Leu Gln Ser
1 5

<210> SEQ ID NO 41
<211> LENGTH: 7
<212> TYPE: PRT
<213> ORGANISM: Homo sapiens

<400> SEQUENCE: 41

Ala Ala Ser Ser Leu Gln Ser
1 5

<210> SEQ ID NO 42
<211> LENGTH: 7
<212> TYPE: PRT
<213> ORGANISM: Homo sapiens

<400> SEQUENCE: 42

Ala Ala Ser Ser Leu Gln Ser
1 5

<210> SEQ ID NO 43
<211> LENGTH: 9
<212> TYPE: PRT
<213> ORGANISM: Homo sapiens

<400> SEQUENCE: 43

Gln Gln Tyr Asn Ser Tyr Pro Pro Thr
1 5

<210> SEQ ID NO 44
<211> LENGTH: 9
<212> TYPE: PRT
<213> ORGANISM: Homo sapiens

<400> SEQUENCE: 44

Gln Gln Tyr Asn Ser Tyr Pro Pro Thr
1 5

<210> SEQ ID NO 45
<211> LENGTH: 9
<212> TYPE: PRT
<213> ORGANISM: Homo sapiens

<400> SEQUENCE: 45

Gln Gln Tyr Asn Ser Tyr Pro Pro Thr
1 5

<210> SEQ ID NO 46
<211> LENGTH: 9
<212> TYPE: PRT
<213> ORGANISM: Homo sapiens

<400> SEQUENCE: 46

Gln Gln Tyr Asn Ser Tyr Pro Pro Thr
1               5

<210> SEQ ID NO 47
<211> LENGTH: 9
<212> TYPE: PRT
<213> ORGANISM: Homo sapiens

<400> SEQUENCE: 47

Gln Gln Tyr Asn Ser Tyr Pro Pro Thr
1               5

<210> SEQ ID NO 48
<211> LENGTH: 9
<212> TYPE: PRT
<213> ORGANISM: Homo sapiens

<400> SEQUENCE: 48

Gln Gln Tyr Asn Ser Tyr Pro Pro Thr
1               5

<210> SEQ ID NO 49
<211> LENGTH: 366
<212> TYPE: DNA
<213> ORGANISM: Homo sapiens

<400> SEQUENCE: 49
gaggtgcagc tggtggagtc tgggggaggc ttggtacagc ctggggagtc cctgagactc 60
tcctgtgtag cctctggatt caccttcagt aggtataaga tgaactgggt ccgccaggct 120
ccagggaagg gactggaatg gatttcatac attagtcgta gtggtcgtga catatactac 180
gcagactctg tgaagggccg attcaccatc tccagagaca atgccaagaa ctcactgtat 240
ctgcaaatga gcagcctgag agacgaggac acggctgtgt attactgtgc gggaactgtc 300
acgacatatt attattactt cggtatggac gtctggggcc tagggaccac ggtcaccgtc 360
tcctca 366

<210> SEQ ID NO 50
<211> LENGTH: 366
<212> TYPE: DNA
<213> ORGANISM: Homo sapiens

<400> SEQUENCE: 50
gaggtgcagc tggtggagtc tgggggaggc ttggtgcagc ctggggagtc cctgagactc 60
tcctgtgtag cctctggatt tactttcagt agatataaga tgaactgggt tcgccaggct 120
ccagggaagg gactggaatg ggtttcatac atcagtcgta gtggccgtga catttactac 180
gcagactctg tgaagggccg attcaccatc tccagagata atgccaagaa ctcactgtat 240
ctgcaaatga acagcctgag agacgaggac acggctgtat attactgtgc gggaactgta 300
acgacatact actactactt cggtatggac gtctggggcc acgggaccac ggtcaccgtc 360
tcctca 366

<210> SEQ ID NO 51
<211> LENGTH: 363
<212> TYPE: DNA
<213> ORGANISM: Homo sapiens

<400> SEQUENCE: 51
gaggtgcagc tggtggagtc tgggggaggc ttggtgcagc ctggggagtc cctgagactc 60
tcctgtgtag cctctggatt tactttcagt agatataaga tgaactgggt tcgccaggct 120
ccagggaagg gactggaatg ggtttcatac atcagtcgta gtggccgtga catttactac 180
gcagactctg tgaagggccg attcaccatc tccagagata atgccaagaa ctcactgtat 240
ctgcaaatga acagcctgag agacgaggac acggctgtat attactgtgc gggaactgta 300
acgacatact actacttcgg tatggacgtc tggggccacg ggaccacggt caccgtctcc 360
tca 363

<210> SEQ ID NO 52
<211> LENGTH: 366
<212> TYPE: DNA
<213> ORGANISM: Homo sapiens

<400> SEQUENCE: 52
gaagtgcagc tggtggagtc tgggggaggc tcggtacagc ctggggagtc cctgagactc 60
tcctgtgtag cctctggatt caccttcagt aggtacaaga tgaactgggt ccgccaggct 120
ccagggaagg gactggaatg ggtttcatac attagtcgta gtggtcgtga catatactac 180
gcagactctg tgaagggccg attcaccatc tccagagaca atgccaagaa ctcactgtat 240
ctgcaaatga acagcctgag agacgaggac acggctgtgt attactgtgc gggaactgta 300
acgacatact actacgactt cggtatggac gtctggggcc aagggaccac ggtcaccgtc 360
tcctca 366

<210> SEQ ID NO 53
<211> LENGTH: 366
<212> TYPE: DNA
<213> ORGANISM: Homo sapiens

<400> SEQUENCE: 53
gaggtgcagc tggtggagtc tgggggaggc ttggtacagc ctggggagtc cctgagactc 60
tcgtgtgtag cctctggatt caccctcagt aggtataaga tgaactgggt ccgccaggct 120
ccagggaagg gactggaatg gatttcatac atcagtcgta gtggtcgtga catatactac 180
gcagactctg tgaagggccg attcaccatc tccagagaca atgccaagaa ctcactgtat 240
ctgcaaatga acagcctgcg agacgaggac tcggctgtgt attactgtgc gggaactgta 300
acgacatact actactactt cggtatggac gtctggggcc aagggaccac ggtcaccgtc 360
tcctca 366

<210> SEQ ID NO 54
<211> LENGTH: 366
<212> TYPE: DNA
<213> ORGANISM: Homo sapiens

<400> SEQUENCE: 54
gaggtgcagc tggtggagtc tgggggaggc ttggtacagc ctggggagtc cctgagactc 60
tcgtgtgtag cctctggatt caccctcagt aggtataaga tgaactgggt ccgccaggct 120
ccagggaagg gactggaatg gatttcatac atcagtcgta gtggtcgtga catatactac 180

-continued gcagactctg tgaagggccg attcaccatc tccagagaca atgccaagaa ctcactgtat 240
ctgcaaatga acagcctgcg agacgaggac tcggctgtgt attactgtgc gggaactgta 300
acgacatact actactactt cggtatggac gtctggggcc aagggaccac ggtcaccgtc 360
tcctca 366

<210> SEQ ID NO 55
<211> LENGTH: 321
<212> TYPE: DNA
<213> ORGANISM: Homo sapiens

<400> SEQUENCE: 55
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagctg cctgcagcct 240
gaagattttg cgacttatta ctgccaacag tataatagtt accctcccac tttcggcgga 300
gggaccaagg tggagatcaa a 321

<210> SEQ ID NO 56
<211> LENGTH: 321
<212> TYPE: DNA
<213> ORGANISM: Homo sapiens

<400> SEQUENCE: 56
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcccac tttcggcgga 300
gggaccaagg tggagatcaa a 321

<210> SEQ ID NO 57
<211> LENGTH: 321
<212> TYPE: DNA
<213> ORGANISM: Homo sapiens

<400> SEQUENCE: 57
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcccac tttcggcgga 300
gggaccaagg tggagatcaa a 321

<210> SEQ ID NO 58
<211> LENGTH: 321
<212> TYPE: DNA
<213> ORGANISM: Homo sapiens

<400> SEQUENCE: 58
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagctg cctgcagcct 240
gaagattttg cgacttatta ctgccaacag tataatagtt accctcccac tttcggcgga 300
gggaccaagg tggagatcaa a 321

<210> SEQ ID NO 59
<211> LENGTH: 321
<212> TYPE: DNA
<213> ORGANISM: Homo sapiens

<400> SEQUENCE: 59
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcccac tttcggcgga 300
gggaccaagg tggagatcaa a 321

<210> SEQ ID NO 60
<211> LENGTH: 321
<212> TYPE: DNA
<213> ORGANISM: Homo sapiens

<400> SEQUENCE: 60
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctcccac tttcggcgga 300
gggaccaagg tggagatcaa a 321

<210> SEQ ID NO 61
<211> LENGTH: 98
<212> TYPE: PRT
<213> ORGANISM: Homo sapiens

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg
```

<210> SEQ ID NO 62

<211> LENGTH: 95
<212> TYPE: PRT
<213> ORGANISM: Homo sapiens

<400> SEQUENCE: 62

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro
85 90 95

<210> SEQ ID NO 63
<211> LENGTH: 122
<212> TYPE: PRT
<213> ORGANISM: Homo sapiens

<400> SEQUENCE: 63

Glu Val Gln Leu Val Glu Ser Gly Gly Gly Leu Val Gln Pro Gly Glu
1 5 10 15

Ser Leu Arg Leu Ser Cys Val Ala Ser Gly Phe Thr Phe Ser Arg Tyr
20 25 30

Lys Met Asn Trp Val Arg Gln Ala Pro Gly Lys Gly Leu Glu Trp Ile
35 40 45

Ser Tyr Ile Ser Arg Ser Gly Arg Asp Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Ser Ser Leu Arg Asp Glu Asp Thr Ala Val Tyr Tyr Cys
85 90 95

Ala Gly Thr Val Thr Thr Tyr Tyr Tyr Tyr Phe Gly Met Asp Val Trp
100 105 110

Gly Leu Gly Thr Thr Val Thr Val Ser Ser
115 120

<210> SEQ ID NO 64
<211> LENGTH: 107
<212> TYPE: PRT
<213> ORGANISM: Homo sapiens

<400> SEQUENCE: 64

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Cys Leu Gln Pro
65 70 75 80

-continued

```
Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105


<210> SEQ ID NO 65
<211> LENGTH: 5
<212> TYPE: PRT
<213> ORGANISM: Homo sapiens

<400> SEQUENCE: 65

Arg Tyr Lys Met Asn
1               5


<210> SEQ ID NO 66
<211> LENGTH: 17
<212> TYPE: PRT
<213> ORGANISM: Homo sapiens

<400> SEQUENCE: 66

Tyr Ile Ser Arg Ser Gly Arg Asp Ile Tyr Tyr Ala Asp Ser Val Lys
1               5                   10                  15

Gly


<210> SEQ ID NO 67
<211> LENGTH: 13
<212> TYPE: PRT
<213> ORGANISM: Homo sapiens

<400> SEQUENCE: 67

Thr Val Thr Thr Tyr Tyr Tyr Tyr Phe Gly Met Asp Val
1               5                   10


<210> SEQ ID NO 68
<211> LENGTH: 11
<212> TYPE: PRT
<213> ORGANISM: Homo sapiens

<400> SEQUENCE: 68

Arg Ala Ser Gln Gly Ile Ser Ser Trp Leu Ala
1               5                   10


<210> SEQ ID NO 69
<211> LENGTH: 7
<212> TYPE: PRT
<213> ORGANISM: Homo sapiens

<400> SEQUENCE: 69

Ala Ala Ser Ser Leu Gln Ser
1               5


<210> SEQ ID NO 70
<211> LENGTH: 9
<212> TYPE: PRT
<213> ORGANISM: Homo sapiens

<400> SEQUENCE: 70

Gln Gln Tyr Asn Ser Tyr Pro Pro Thr
1               5


<210> SEQ ID NO 71
<211> LENGTH: 25
<212> TYPE: PRT
<213> ORGANISM: Homo sapiens
```

<400> SEQUENCE: 71

Gly Thr Val Thr Thr Tyr Tyr Tyr Tyr Phe Gly Met Asp Val Trp Gly
1 5 10 15

Gln Gly Thr Thr Val Thr Val Ser Ser
20 25

<210> SEQ ID NO 72
<211> LENGTH: 25
<212> TYPE: PRT
<213> ORGANISM: Homo sapiens

<400> SEQUENCE: 72

Gly Thr Val Thr Thr Tyr Tyr Tyr Tyr Phe Gly Met Asp Val Trp Gly
1 5 10 15

Leu Gly Thr Thr Val Thr Val Ser Ser
20 25

<210> SEQ ID NO 73
<211> LENGTH: 25
<212> TYPE: PRT
<213> ORGANISM: Homo sapiens

<400> SEQUENCE: 73

Gly Thr Val Thr Thr Tyr Tyr Tyr Tyr Phe Gly Met Asp Val Trp Gly
1 5 10 15

His Gly Thr Thr Val Thr Val Ser Ser
20 25

<210> SEQ ID NO 74
<211> LENGTH: 24
<212> TYPE: PRT
<213> ORGANISM: Homo sapiens

<400> SEQUENCE: 74

Gly Thr Val Thr Thr Tyr Tyr Tyr Phe Gly Met Asp Val Trp Gly His
1 5 10 15

Gly Thr Thr Val Thr Val Ser Ser
20

<210> SEQ ID NO 75
<211> LENGTH: 25
<212> TYPE: PRT
<213> ORGANISM: Homo sapiens

<400> SEQUENCE: 75

Gly Thr Val Thr Thr Tyr Tyr Tyr Tyr Phe Gly Met Asp Val Trp Gly
1 5 10 15

Leu Gly Thr Thr Val Thr Val Ser Ser
20 25

<210> SEQ ID NO 76
<211> LENGTH: 25
<212> TYPE: PRT
<213> ORGANISM: Homo sapiens

<400> SEQUENCE: 76

Gly Thr Val Thr Thr Tyr Tyr Tyr Asp Phe Gly Met Asp Val Trp Gly
1 5 10 15

Gln Gly Thr Thr Val Thr Val Ser Ser
20 25

-continued

```
<210> SEQ ID NO 77
<211> LENGTH: 12
<212> TYPE: PRT
<213> ORGANISM: Homo sapiens

<400> SEQUENCE: 77

Pro Thr Phe Gly Gly Gly Thr Lys Val Glu Ile Lys
1               5                   10
```